United States Patent
Shi et al.

(10) Patent No.: US 10,294,478 B2
(45) Date of Patent: May 21, 2019

(54) APTAMER MODULATORS OF ESTROGEN RECEPTORS

(75) Inventors: Hua Shi, Ithaca, NY (US); Daiying Xu, Quincy, MA (US); Vamsee Krishna Chatakonda, Albany, NY (US)

(73) Assignee: The Research Foundation for The State University of New York, Albany, NY (US)

( * ) Notice: Subject to any disclaimer, the term of this patent is extended or adjusted under 35 U.S.C. 154(b) by 0 days.

(21) Appl. No.: 14/239,012

(22) PCT Filed: Aug. 16, 2012

(86) PCT No.: PCT/US2012/051197
§ 371 (c)(1),
(2), (4) Date: Sep. 22, 2014

(87) PCT Pub. No.: WO2013/025930
PCT Pub. Date: Feb. 21, 2013

(65) Prior Publication Data
US 2015/0031754 A1    Jan. 29, 2015

Related U.S. Application Data
(60) Provisional application No. 61/524,150, filed on Aug. 16, 2011.

(51) Int. Cl.
| C12N 15/11 | (2006.01) |
| C12N 15/115 | (2010.01) |
| C07K 14/72 | (2006.01) |

(52) U.S. Cl.
CPC .......... *C12N 15/115* (2013.01); *C07K 14/721* (2013.01); *C12N 2310/16* (2013.01); *C12N 2310/51* (2013.01); *C12N 2330/51* (2013.01)

(58) Field of Classification Search
CPC .............. C12N 15/115; C12N 2310/16; C12N 2330/51; A01K 2207/05
See application file for complete search history.

(56) References Cited

U.S. PATENT DOCUMENTS

| 5,744,356 A * | 4/1998 | Traish ................ C07K 16/2869 435/331 |
| 6,686,351 B2 * | 2/2004 | Bhagwat .............. C07D 209/44 514/213.01 |
| 2003/0008314 A1 * | 1/2003 | Priuska .............. G01N 21/6428 435/6.11 |
| 2004/0053310 A1 | 3/2004 | Shi et al. |
| 2005/0282190 A1 | 12/2005 | Shi et al. |
| 2007/0083334 A1 | 4/2007 | Mintz et al. |
| 2007/0089189 A1 * | 4/2007 | Huang ............... C12N 15/8216 800/278 |
| 2009/0197271 A1 | 8/2009 | Kotlikoff et al. |
| 2009/0291972 A1 | 11/2009 | Shapiro et al. |
| 2010/0016352 A1 * | 1/2010 | Li ......................... A61K 31/35 514/312 |
| 2010/0035855 A1 * | 2/2010 | Hyde .................... A61K 31/00 514/182 |
| 2011/0224149 A1 * | 9/2011 | Xiao .................... C12Q 1/6886 514/19.4 |
| 2011/0311517 A1 * | 12/2011 | Li ....................... A61K 31/138 424/130.1 |
| 2012/0141382 A1 * | 6/2012 | Shi .......................... B82Y 5/00 424/9.323 |
| 2013/0129719 A1 * | 5/2013 | Giangrande ....... C12N 15/1135 424/133.1 |

FOREIGN PATENT DOCUMENTS

| IN | 1375/KOL/2013 A | * | 1/2014 |
| WO | WO2012004790 | * | 1/2012 |

OTHER PUBLICATIONS

Written Opinion of the International Search Authority PCT/US12/51197, dated Dec. 2012, pp. 1-8.*
Hartman et al. Steroids 74, 2009, 635-641.*
Sumedha Jayasena Clinical Chemisty 45:9, 1628-1650, 1999.*
Zhou et al. Chemistry & Biology, pp. 644-645 (Year: 2008).*
Li et al. Molecular and Cellular Biology, 24: 7681-7694 (Year: 2004).*
Xu et al., "Two classes of RNA aptamers as antagonists of human estrogen receptor alpha," RNA-UNY Structure, Function Application 2010—Poster Presentation (Oct. 8, 2010).
International search report and written opinion for corresponding application PCT/US/2012/051197 (dated Dec. 7, 2012).

* cited by examiner

*Primary Examiner* — Brian Whiteman
(74) *Attorney, Agent, or Firm* — Pepper Hamilton LLP

(57) ABSTRACT

The present invention relates to a nucleic acid aptamer molecule that includes a domain that binds to an estrogen receptor, molecular complexes that include the nucleic acid aptamer molecule and an estrogen receptor, and constructed DMA molecules and expression systems, as well as host cells, that the contain an RNA aptamer molecule of the invention. Use of these aptamers and encoding constructs to inhibiting estrogen receptor activity in a cell and to treat estrogen receptor-positive cancers is also described.

15 Claims, 20 Drawing Sheets
Specification includes a Sequence Listing.

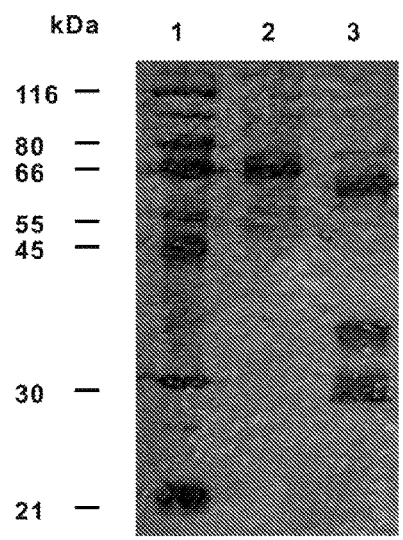
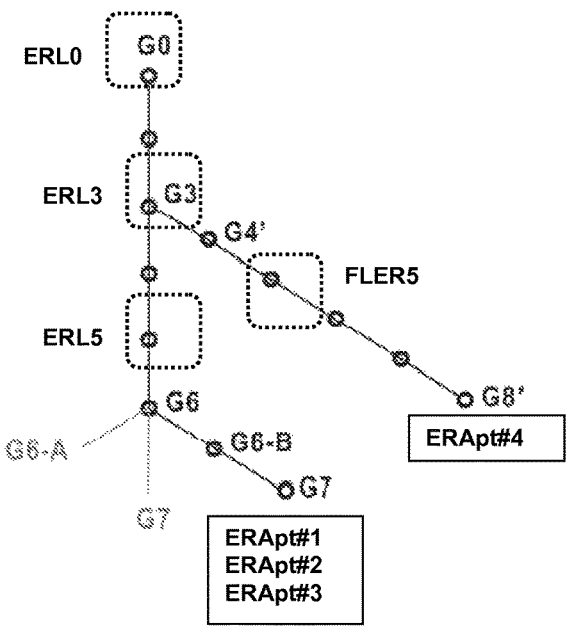
*FIG. 4A*  *FIG. 4B*
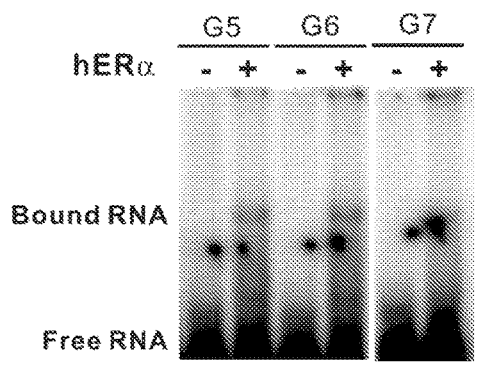
*FIG. 4C*

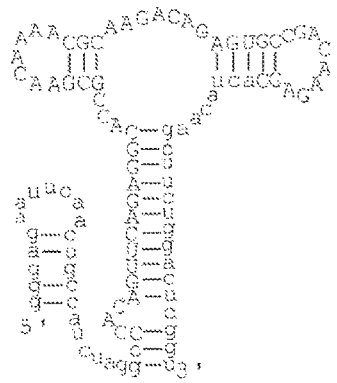
FIG. 5A (AptER-1)
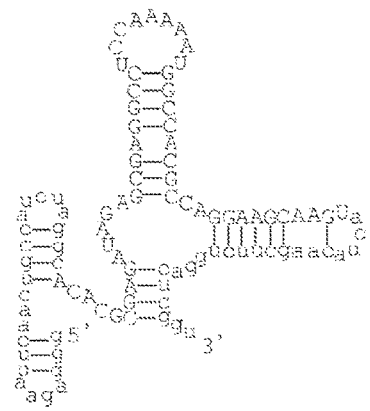
FIG. 5B (AptER-2)
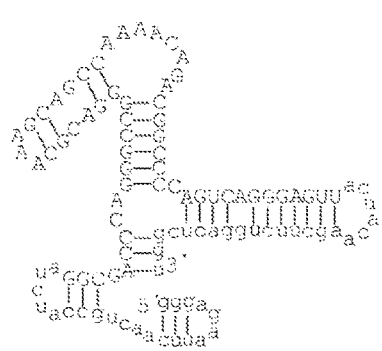
FIG. 5C (AptER-3)
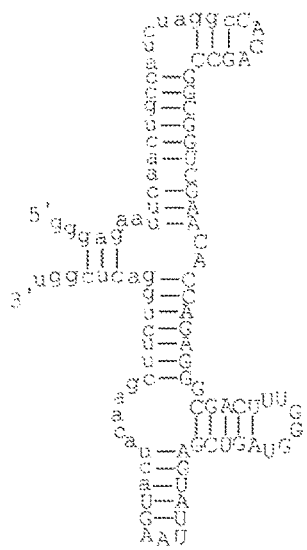
FIG. 5D (AptER-4)

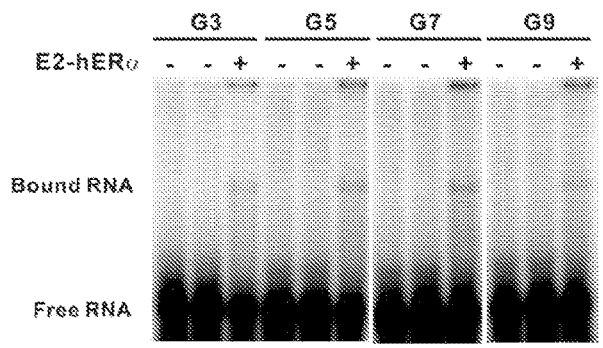 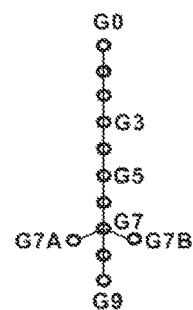
FIG. 6A                    FIG. 6B
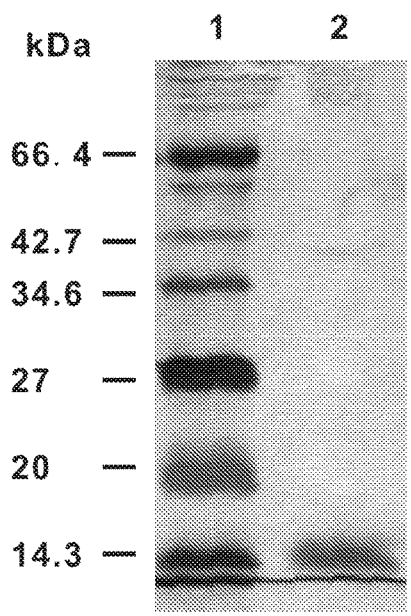 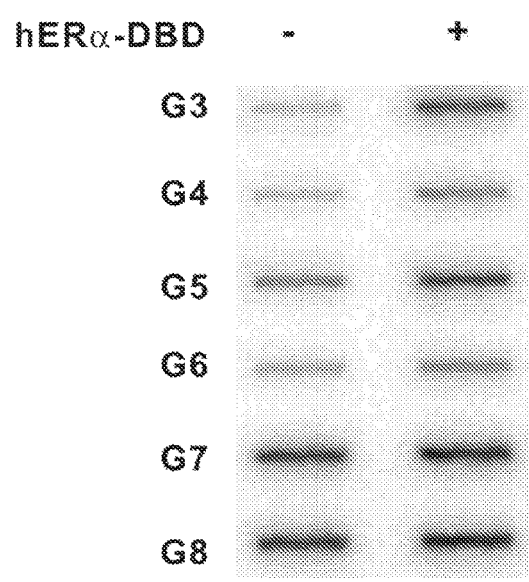
FIG. 7A                    FIG. 7B

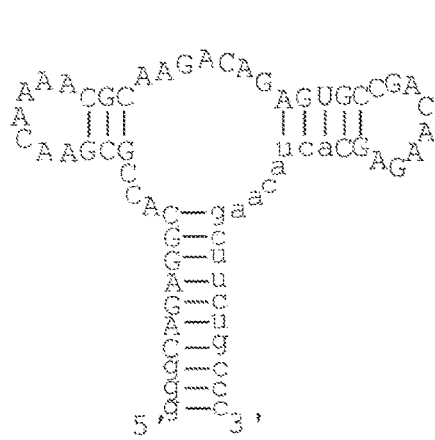
FIG. 13A
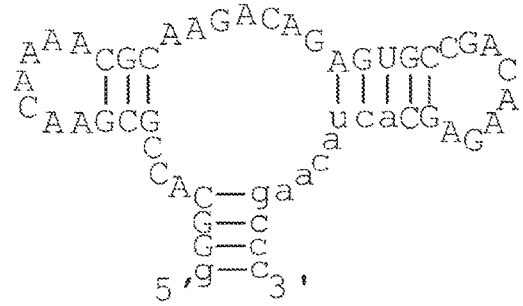
FIG. 13B
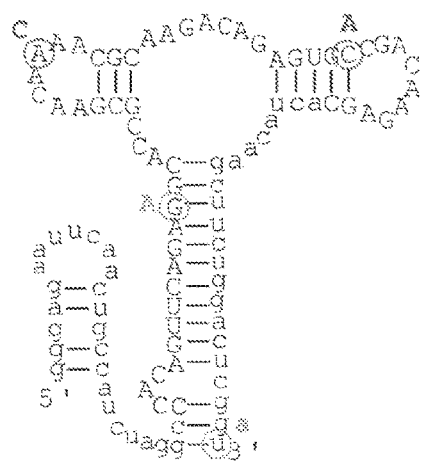
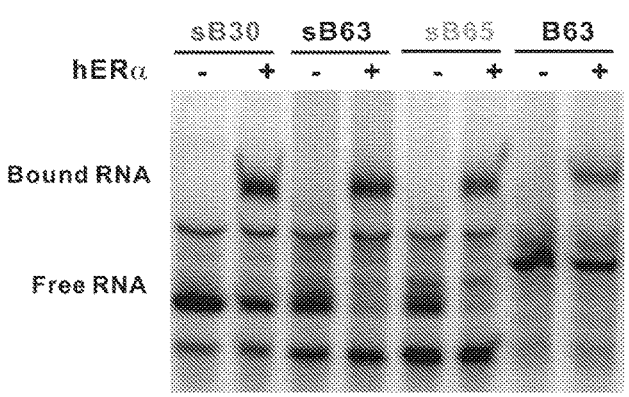
FIG. 13C

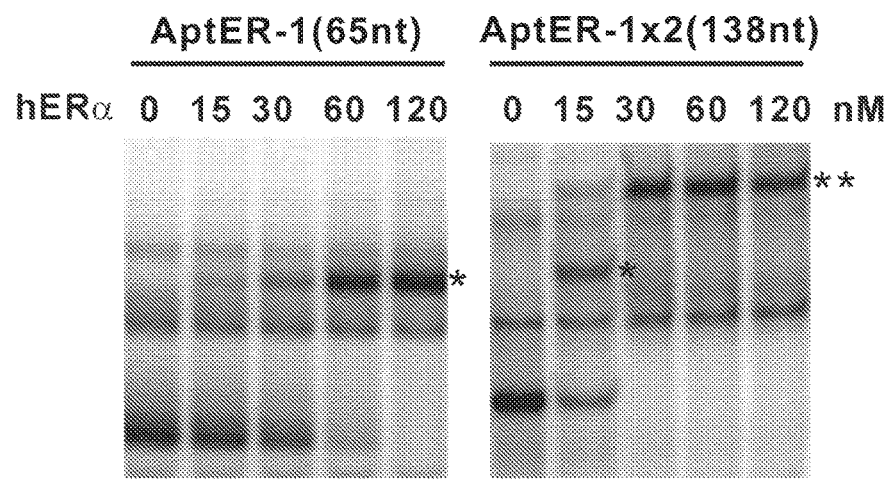
FIG. 14B
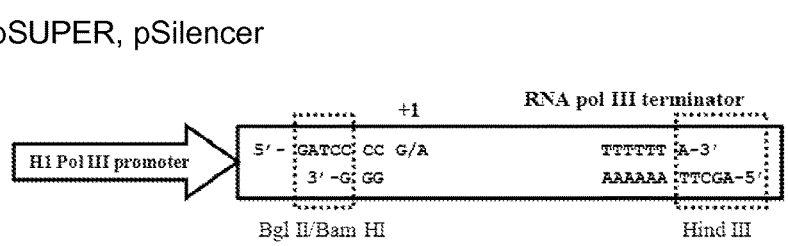
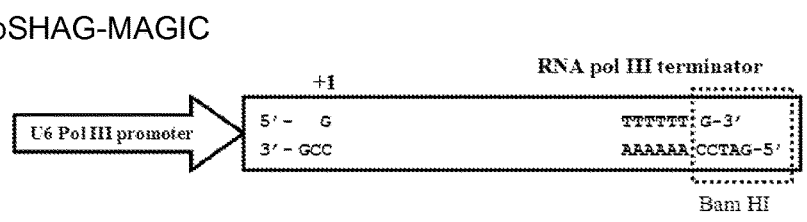
FIG. 15A

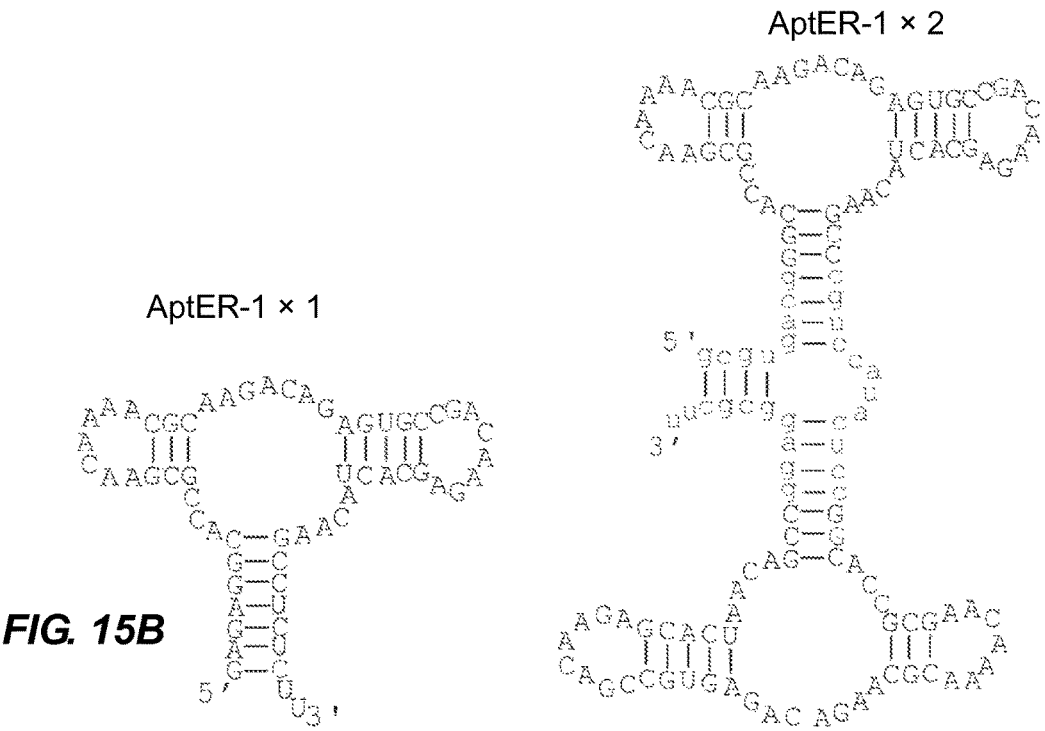
AptER-1 × 1
*FIG. 15B*
AptER-1 × 2
*FIG. 15C*
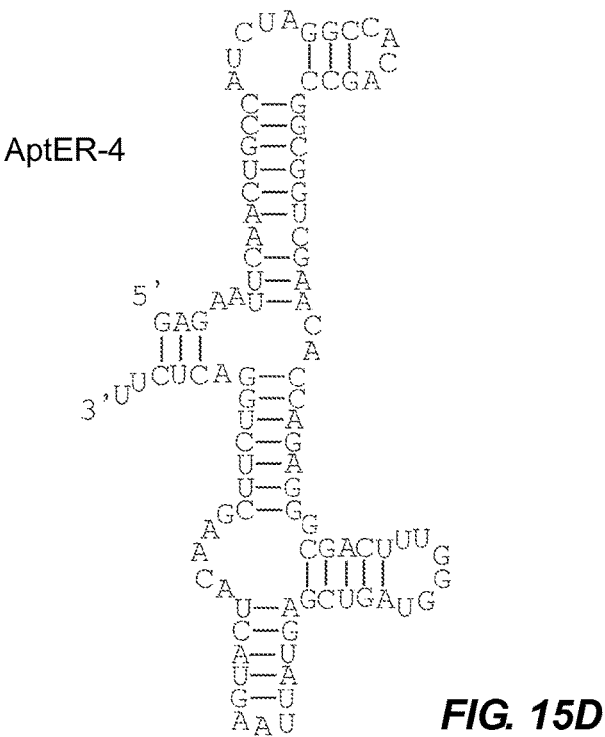
AptER-4
*FIG. 15D*

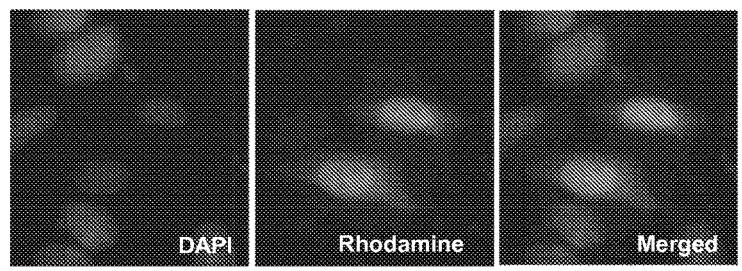
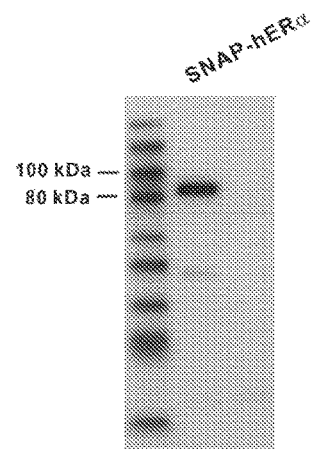
FIG. 18A
FIG. 18B
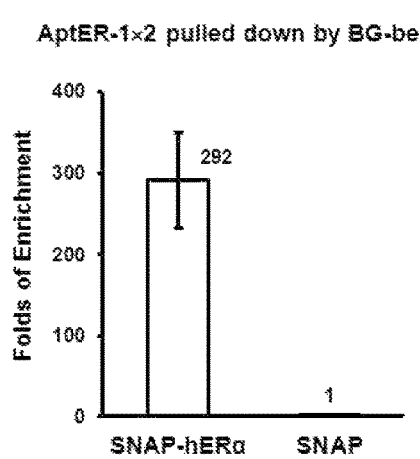
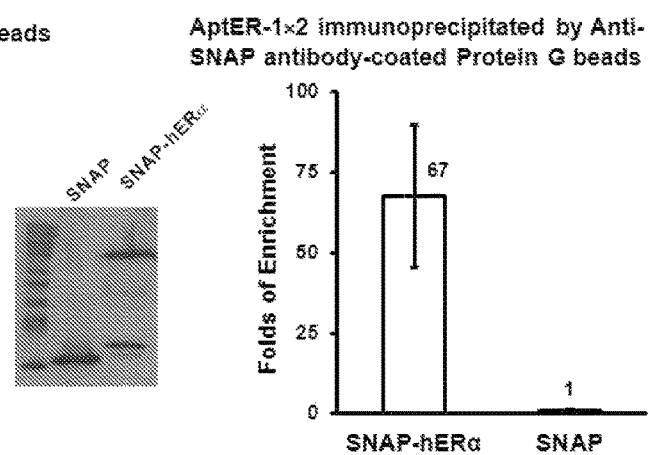
FIG. 18C

APTAMER MODULATORS OF ESTROGEN RECEPTORS

This application is a national stage application under 35 U.S.C. § 371 of PCT Application No. PCT/US2012/051197, filed Aug. 16, 2012, which claims the benefit of U.S. Provisional Patent Application Ser. No. 61/524,150, filed on Aug. 16, 2011, which is hereby incorporated by reference in its entirety.

FIELD OF THE INVENTION

The present invention relates to nucleic acid aptamer molecules that bind specifically to an estrogen receptor, and use of these aptamer molecules or DNA constructs encoding the same to inhibit estrogen receptor activity in a cell or treating a patient for an estrogen dependent cancer.

BACKGROUND OF THE INVENTION

The nuclear receptor superfamily is a group of ligand-inducible transcription factors that regulate specific target genes involved in biological processes as diverse as metabolism, development and reproduction (Mangelsdorf et al., "The Nuclear Receptor Superfamily: The Second Decade," *Cell* 83(6):835-839 (1995)). Members in this family mediate the transcriptional response to hormones such as the sex steroids, adrenal steroids, vitamin D3, thyroid and retinoid hormones, in addition to a variety of metabolic ligands. Upon association with their cognate ligands, nuclear receptors acquire increased affinity for specific chromosomal binding sites, thereby recruiting a diverse group of coregulators to either activate or repress transcription initiation from the nearby promoter.

Nuclear receptors may be classified as one of two broad types based on their localization in the absence of ligand: Type I receptors, represented by estrogen receptor (ER), progesterone receptor (PR) and androgen receptor (AR), undergo nuclear translocation upon ligand activation and usually bind as homodimers to inverted repeating DNA half sites, called hormone response elements, or HREs. Type II receptors, such as thyroid hormone receptor and retinoic acid receptor, are often retained in the target cell nucleus regardless of the presence of ligand, and usually bind as heterodimers with RXR to direct repeats (Klinge et al., "Binding of Type II Nuclear Receptors and Estrogen Receptor to Full and Half-site Estrogen Response Elements in vitro," *Nucleic Acids Res* 25(10):1903-1912 (1997)).

In addition to their normal functions, nuclear receptors have been implicated in many pathological processes, such as breast cancer, prostate cancer, ovarian cancer, diabetes and obesity (Novac and Heinzel, "Nuclear Receptors: Overview and Classification," *Curr Drug Targets Inflamm Allergy* 3(4):335-346 (2004)). Some nuclear receptors have been important pharmacological targets for decades, considering the fact that over 13% of commonly prescribed drugs target nuclear receptors, with 15 of these drugs in the top 200 prescribed medicines (Via, "Nuclear Receptors: The Pipeline Outlook Report—Overview," *Cambridge Healthtech Institute* (2010)). Among them, human estrogen receptor alpha (hERα) and progesterone receptor are most important biomarkers in breast cancer prognosis, in prediction of tumor response to hormone suppression therapy, and as drug targets in breast cancer treatments.

As members in the nuclear receptor superfamily share common structure architecture (Evans et al., "The Steroid and Thyroid Hormone Receptor Superfamily," *Science* 240 (4854):889-895 (1988); Mangelsdorf et al., "The Nuclear Receptor Superfamily: The Second Decade," *Cell* 83(6):835-839 (1995)) and similar functionalities, hERα represents a model for Type I nuclear receptors. Furthermore, hERα is an important receptor to study given its significant role in breast cancer.

Besides skin cancer, breast cancer is the most commonly diagnosed cancer (about 28%) among U.S. women. In general, breast cancer treatments may include surgery to remove cancerous tissue, chemotherapeutic agents to kill cancer cells, radiation therapy to destroy cancerous tissue and other adjuvant therapies, depending on factors such as type and stage of the cancer, menopausal status, and prognostic/predictive biomarkers. A large number of breast cancers (up to 70%) are sensitive to the hormone estrogen, which functions as a mitogen to promote breast cancer cell proliferation. Such cancers express high level of ERα, and are called ERα-positive breast cancers. In contrast to tumor cells, ERα-positive cells in the normal human breast generally do not proliferate in response to estrogen. ERα in this subset of normal breast epithelial cells acts as the sensor of circulating or local estrogen concentrations, and the non-proliferating ER-positive cell is stimulated by estrogen to secrete growth factors for the paracrine control of neighboring ERα-negative epithelial cells proliferation (Clarke et al., "Dissociation Between Steroid Receptor Expression and Cell Proliferation in the Human Breast," *Cancer Res* 57(22):4987-4991 (1997)).

Long term hormone blocking therapy is given to ERα-positive breast cancer patients. Estrogen functions are usually reduced in two ways. One way is to decrease estrogen synthesis using an aromatase inhibitor, represented by anastrozole and letrozole. Aromatase inhibitors block the final step in the conversion of androgen to estrogen. However, they are only suitable for post-menopausal patients (Buzdar, "New Generation Aromatase Inhibitors—from the Advanced to the Adjuvant Setting," *Breast Cancer Res Treat* 75(Suppl 1): S13-17 (2002)). The other approach targets ER ligand binding pocket to competitively inhibit estrogen binding to ER using selective estrogen receptor modulators (SERMs), represented by tamoxifen (TAM). TAM is metabolized in the liver into active metabolites such as 4-hydroxy-tamoxifen (4-OHT), which antagonizes estrogen receptor activation in breast tissue, resulting in inhibition of tumor growth. However, it has been reported that TAM has estrogen-like activities in uterus, bone, liver, and the cardiovascular system, which enhances bone maintenance but increases the risk of endometrial cancer and causes alterations in liver function. Furthermore, after prolonged treatment, cancers gain resistance to the anti-estrogen treatment (Normanno et al., "Mechanisms of Endocrine Resistance and Novel Therapeutic Strategies in Breast Cancer," *Endocr Relat Cancer* 12(4):721-747 (2005)), the mechanism of which remains poorly understood. This has led to the active pursuit of better ER modulators that display the optimal agonistic or antagonistic activities in various estrogen target tissues (Katzenellenbogen et al., Wouldiam L. McGuire Memorial Lecture "Antiestrogens: Mechanisms of Action and Resistance in Breast Cancer," *Breast Cancer Res Treat* 44(1): 23-38 (1997)). Therefore, understanding ER actions, validating more drug target sites on the ER, and identifying new agents as drugs for these target sites are central goals for maximizing treatment opportunities in breast cancer therapy.

The present invention is directed to overcoming these and other deficiencies in the art.

SUMMARY OF THE INVENTION

A first aspect of the present invention relates to a nucleic acid aptamer molecule that includes a domain that binds to an estrogen receptor. Exemplary aptamer molecules include those that bind to hERα and those that bind to hERβ.

A second aspect of the present invention relates to a molecular complex that includes a nucleic acid aptamer molecule according to the first aspect of the invention and an estrogen receptor.

A third aspect of the present invention relates to a constructed DNA molecule that includes a region encoding an RNA aptamer molecule according to the first aspect of the invention. Expression systems and host cells containing the constructed DNA molecule are also encompassed by this aspect of the invention.

A fourth aspect of the present invention relates to a method of inhibiting estrogen receptor activity in a cell. This method includes contacting an estrogen receptor in a cell with a nucleic acid aptamer molecule according to the first aspect of the invention, whereby the nucleic acid aptamer molecule binds to the estrogen receptor and inhibits activity thereof.

A fifth aspect of the present invention relates to a method of treating a patient for an estrogen dependent cancer. This method includes administering to the patient an agent comprising or encoding a nucleic acid aptamer molecule according to the first aspect of the invention, whereby the agent is taken up by an estrogen dependent-cancer cell and the nucleic acid aptamer molecule inhibits activity of the estrogen receptor in the cancer cell and thereby inhibits cancer cell growth.

The accompanying examples demonstrate the in vitro generation of RNA aptamer molecules that bind to discrete sites on hERα or hERβ. One class of three RNA aptamers, designated as AptER-1, -2 and -3, were isolated using hERα as the target for selection. AptER-1, -2 and -3 apparently share an overlapping binding site on hERα. To generate aptamers for other surfaces, a second in vitro selection was performed while using a truncated AptER-1 aptamer to mask the binding site of Class I aptamer on hERα. Another aptamer, designated as AptER-4, was isolated, and proven to have distinct binding features from the first class of aptamers. AptER-4 therefore belongs to a second class.

These two classes of aptamers were characterized in several aspects, including their binding affinities and specificities to hERs, the essential moiety of aptamers, and their binding sites on the target proteins. The dissociation constant ($K_d$) of the aptamers was determined using nitrocellulose filter-binding assays. AptER-1 is the tightest binder ($K_d$=16 nM) among the three Class I aptamers. AptER-4 has a $K_d$ of 40 nM to hERα, but its affinity to hERβ is very low, i.e., it is highly selective for hERα. In comparison, Class I aptamers bind to the two hER subtypes with similar affinity. Furthermore, it is demonstrated that AptER-1 and AptER-4 bind to different regions on hERα as confirmed by: a) their noncompetitive binding to hERα; and b) their differences in the mobility of their aptamer-hERα complexes. The minimal RNA region required for aptamer binding activity was determined for AptER-1 to be a 53nt stem loop construct, while the full length AptER-4 is required for binding. Both of these aptamers bind to sites on the hERα that are discrete from the DNA binding domain (DBD) and ligand binding domain (LBD).

DNA constructs and expression vectors were prepared for intracellular expression of monovalent or multivalent forms of these aptamers. RNA polymerase III promoters were employed. These vectors included those encoding AptER-1 monomer, AptER-1 dimer, and the full length AptER-4 monomer. Using these expression constructs, they were introduced into mammalian cell lines by transient transfection and the expression levels of the aptamers were assessed in a time course in both MCF7 and HEK293FT using qPCR. The ability of the expressed aptamers to inhibit hERα-dependent transcriptional activation was examined in dual-luciferase assays, with the AptER-1 dimer being most effective. The association between AptER-1 dimer and hERα (e.g., formation of a molecular complex) was verified in HeLa cells using both RNA pull-down and RNA co-immunoprecipitation assays. On this basis, these aptamers and their derivatives should prove useful as therapeutic agents either to inhibit ER-dependent cancer cell growth or destroy ER-dependent cancer cells.

BRIEF DESCRIPTION OF THE DRAWINGS

FIGS. 4A-C illustrate the in vitro selection of unliganded hERα-binding RNA aptamers. FIG. 4A is an image of a Western blot of baculovirus-expressed full-length hERα and GST/ERα-LBD, which were used as target proteins in the selections. Lane 1, protein molecular weight standards (Invitrogen, Cat#P-6649); Lane 2, hERα preparation from baculovirus-infected cells, MW=66 kDa; Lane 3, GST/ERα-LBD preparation from baculovirus-infected cells, containing amino acids 282-595, MW=62.8 kDa. The two bands between 30 kDa and 45 kDa in GST/ERα-LBD may be GST tag and its dimer. FIG. 4B illustrates the lineage structure of in vitro selection I and II for aptamers against apo-hERα. Abandoned pools are shown in grey, whereas the pools leading to the final selected pool from which aptamers were isolated are shown in black. Gx refers to generation number. Gx represents ERLx pools and Gx' represents FLERx pools. Dotted squares represents RNA pools that were sequenced using next generation sequencing in Example 9. Aptamers ERApt#1, 2 and 3 represented in solid boxes are isolated from G7 (ERL7) pool and aptamer ERApt#4 was isolated from G8' (FLER8) pool. Short form of ER Apt#1 was used to block ERα and SELEX was performed using pool G3-G8' to suppress class I aptamers. Pools in grey were abandoned due to enrichment of non-specific RNA species. FIG. 4C illustrates the enrichment of unliganded hERα-binding RNA molecules with successive rounds of selection. The affinity of different RNA pool to unliganded hERα was assayed using a gel shift assay on a 2% agarose gel. RNA probes from the selected pools were uniformly labeled and incubated with 260 nM hERα. Despite the presence of black dots that do not align with any lane, which were caused by residue signal on the contaminated storage phosphor screen, the presence of bound RNA is shown.

FIGS. 5A-D illustrate the predicted secondary structures of unliganded hERα-binding RNA sequences AptER-1 (5A, SEQ ID NO: 1), AptER-2 (5B, SEQ ID NO: 2), AptER-3 (5C, SEQ ID NO: 3), and AptER-4 (5D, SEQ ID NO: 4). Nucleotides in the variable region are represented by capital letters. Nucleotides derived from the constant flanking region are in lowercase.

FIGS. 6A-B illustrate the in vitro selection of aptamers against E2-liganded GST/hERα-LBD. FIG. 6A illustrates the affinity of different RNA pools to E2-liganded GST/hERα-LBD or BSA, which were assayed using a gel shift assay on 2% agarose gel. RNA probes from the selected pools were uniformly labeled and incubated with 260 nM GST/hERα-LBD in the presence of 1 µM E2 or the same concentration of BSA. Gx refers to the generation or round of a specific RNA pool. For example, G3 is the RNA pool generated after three rounds of selection. FIG. 6B illustrates the lineage structure of in vitro selection for aptamers against E2-liganded GST/hERα-LBD. G3, 5, 7 and 9 labeled were subjected to EMSA. G7A was selected in a gel selection based on G7 pool; G7B was the resulting pool after a RNase treatment of G7 pool to remove FBS.

FIGS. 7A-B illustrate the in vitro selection of aptamers against $His_6$-tagged hERα-DBD. FIG. 7A is a Western blot of $His_6$-tagged hERα-DBD, which was used as a target protein in the selection. Lane 1, Protein Marker, Broad Range (2-212 kDa) (New England Biolabs); Lanes 2, $His_6$-tagged hERα-DBD preparation from E. coli BL21 (DE3). It contains amino acid 180 to 268 of hERα and a hexa histidine-tag at the N-terminus. MW=11 kDa. FIG. 7B illustrates the enrichment of $His_6$-tagged hERα DBD-binding RNA molecules with successive rounds of selection. The affinity of different RNA pools to hERα-DBD was examined using a filter-binding assay. RNA probes from the selected pools were uniformly labeled and incubated with 200 nM $His_6$-tagged hERα-DBD in a 20 µl binding reaction. Gx refers to the generation or round of a specific RNA pool, as defined above.

FIGS. 8A-D illustrates the binding curves of the four apo-hERα aptamers, AptER-1 (8A), AptER-2 (8B), AptER-3 (8C), and AptER-4 (8D), to the target protein determined using filter-binding assays. Estimated $K_d$ is shown above each curve. Around 0.1 nM radiolabeled RNA aptamer was incubated with apo-hERα ranging from 5 to 150 nM. The binding activity (% binding) was the signal of RNA-protein complex at each concentration as a percentage of the saturated signal. The experiments were done three times and average % binding was determined and used to construct the binding curve. FIG. 8E illustrates EMSA showing binding affinity of the three Class I aptamers to apo-hERα. Binding reactions of 20 µl were set up with constant amount of radiolabeled RNA aptamer and increasing concentrations of apo-hERα (0, 10, 20 and 40 nM), and resolved on 4.8% polyacrylamide gel (acrylamide:bis-acrylamide=37.5:1) in ¼×TBE buffer.

FIG. 9A shows an EMSA illustrating that all three aptamers bound to hERα and hERβ, but not proteins in HeLa nuclear extract. Radiolabeled AptER-1, -2 and -3 (0.1 nM) were incubated with 20 nM hERα, 200 nM hERβ, or 200 µg/ml HeLa nuclear extract (NE). Binding reactions were resolved on a 4.8% polyacrylamide gel (acrylamide:bis-acrylamide=37.5:1) in ¼×TBE buffer. FIG. 9B shows an EMSA illustrating that each aptamer bound to the two ER subtypes with similar affinities. Radiolabeled AptER-1, -2 and -3 (0.1 nM) were incubated with 20 nM or 40 nM hERα, or hERβ. Binding reactions were resolved as described above.

FIG. 10A shows the results of a cross competition assay showing that the three Class I aptamers competed for binding to hERα. Radiolabeled AptER-1 RNA (0.1 nM) was mixed with 2000× or 8000× more concentrated nonradioactive competitors AptER-1, -2, or -3 RNA or ERE-50mer before addition of apo-hERα (20 nM) in the binding reactions. The binding reactions were resolved on 4.8% polyacrylamide gel (acrylamide:bis-acrylamide=37.5:1) in ¼× TBE buffer. The same electrophoresis conditions were applied to all the assays in 10A-D. FIG. 10B shows an EMSA (lanes 1-4) illustrating RNA-protein complexes of different mobilities formed by the full length AptER-1 and AptER-4. Aptamers were around 0.5 nM, and hERα was 50 nM in the AptER-1 binding reactions and 150 nM in the AptER-4 binding reaction because the two aptamers have different affinities. Cross competition assay (lanes 3-7) showed that AptER-1(65nt) (SEQ ID NO: 5) affected the binding between AptER-4 to hERα. Radiolabeled AptER-4 (0.5 nM) was mixed together with 3000× more concentrated cold competitors AptER-1(65nt) before addition of hERα to the binding reactions. FIG. 10C shows the cross competition between radiolabeled AptER-4 and cold AptER-1(65nt) examined using a filter-binding assay to show that AptER-1(65nt) did not disrupt the interaction between AptER-4 and hERα. AptER-4 (0.1 nM) was challenged by 15,000× or 45,000× more concentrated nonradioactive AptER-4, AptER-1(65nt) or Generation 1 RNA pool of E2-liganded GST/hERα-LBD selection (G1) for binding to hERα present at 100 nM. FIG. 10D shows a cross competition assay showing that AptER-1(65nt) and AptER-4 did not compete with each other for binding to hERα. Radiolabeled AptER-1(65nt) RNA (1 nM) was mixed together with 1500× more concentrated cold competitor AptER-4 to the binding reactions. The concentration of hERα was 50 or 150 nM as marked.

FIG. 11A is an image of a DBD-ERE binding assay showing that $His_6$-tagged hERα-DBD preparation from E. coli BL21 (DE3) could bind ERE-50mer which contains one copy of Xenopus laevis vitellogenin A2 ERE. End-labeled ERE-50mer (5 nM) was incubated with 100, 200 or 400 nM $His_6$/hERα-DBD and the binding reaction was resolved on a 4.8% polyacrylamide gel (acrylamide:bis-acrylamide=50:1) in ½ ΔTGB. FIG. 11B shows an EMSA illustrating that AptER-1 did not bind $His_6$/hERα-DBD. In the presence of 50 or 100 nM hERα, radiolabeled AptER-1 was shifted. No binding activity to RNase inhibitor (control) or DBD & RNase inhibitor was detected. The binding reactions were resolved on the same type of gel as above. FIG. 11C is a cross competition assay between radioactive ERE-50mer and the three Class I aptamers, showing that aptamers did not compete with ERE-50mer for binding to hERα. End-radiolabeled ERE-50mer at 5 nM was mixed with 100× or 400× more concentrated unlabeled competitors ERE-50mer, AptER-1, -2 and -3 RNA or an early generation pool in hERα selection G1 before addition of hERα (40 nM). Only cold ERE-50mer disrupted radioactive ERE-hERα complex. FIG. 11D is a cross competition assay between ERE-50mer and AptER-4, showing that the aptamer did not compete with ERE for binding to hERα. Left: positive control showed that end-radiolabeled ERE-50mer (5 nM) was shifted by hERα (150 nM); complex formed by hERα (150 nM) and internal-labeled AptER-4 (0.5 nM) was not disrupted in the presence of 5000× more concentrated unlabeled competitor ERE-50mer. Right: radioactive ERE-50mer was challenged by 1500× more concentrated unlabeled competitor AptER-4, but no interference with hERα association was observed.

In FIG. 12A, the ligand competition assays show that the interaction between AptER-1 and hERα was not intervened by ligand-binding. Human ERα was incubated with ligands (40 nM to 5 μM E2 or OHT) or vehicle control (EtOH) at 37° C. for 10 min before addition of RNA. Regardless of the absence or presence of the ligands, hERα formed a complex with AptER-1 in the same way. In FIG. 12B, the ligand competition assays showing that the interaction between AptER-4 and hERα was not intervened by ligand-binding. Human ERα was incubated with 1 μM E2 or vehicle control (EtOH) before addition of AptER-4. Regardless of the absence or presence of the ligands, hERα formed a complex with AptER-4 in the same way. In FIG. 12C, the EMSA shows that neither AptER-1 nor AptER-4 bound to GST/hERα-LBD. Proteins were 100 nM. In the presence of hERα, both aptamers were shifted. No binding activity to GST/hERα-LBD was detected.

FIGS. 13A-C delineate the minimal binding elements on AptER-1 (compare to FIG. 5A, showing full-length AptER-1 (SEQ ID NO: 1)). FIG. 13A illustrates the secondary structure of truncated sequence AptER-1(65nt), SEQ ID NO: 5, as predicted by mFold. FIG. 13B illustrates the secondary structure of truncated sequence AptER-1(53nt), SEQ ID NO: 6, as predicted by mFold. In FIGS. 13A-B, sequences in the variable regions are represented as capital letters, and sequences in the constant regions or additional GC pairs in the end-most stem are shown in lowercase. FIG. 13C shows the predicted structures for several derivative clones of AptER-1 (SEQ ID NO: 1) and their 65nt truncated version examined in EMSA. The secondary construct was made with the full-length clone B63, the dominant clone (7 out of 9) of AptER-1. The nucleotide substitutions in clone B30 (SEQ ID NO: 11) are shown in red, and those in clone B65 (SEQ ID NO: 12) are shown in blue. In the presence of hERα at 25 nM, the difference in their binding affinity were shown. The relative low binding activity of the full-length B63 at this protein concentration exhibited here in comparison to the previous EMSA, was probably due to the reduced protein functional activity of hERα after its 2nd frozen-thaw handling.

FIG. 14A-B illustrate the increased avidity of dimeric AptER-1. In FIG. 14A illustrates predicted secondary structure of construct AptER-1×2(138nt) (SEQ ID NO: 7) by mFold. Sequences of the three-way junction are shown in red and lowercase; sequences of the aptamer unit are represented by capital letters. FIG. 14B illustrates a comparison of AptER-1(65nt) and AptER-1×2(138nt) affinity to hERα. Left panel: shifted band was labeled with asterisk (*). Right panel: band single-astericked (*) represented protein occupying one aptamer unit; band double-astericked (**) represented protein occupying both aptamer units.

FIGS. 15A-D illustrate schematically the construction of aptamer expression vectors for mammalian cell-based assays. FIG. 15A shows the design of aptamer expression cassettes. The transcript initiates at +1 site, which is usually a purine. Upper panel: the linearized pSUPER and pSilencer vector share the same overhangs, Bgl II/Bam HI immediately downstream of HI promoter and Hind III downstream of the terminator. Lower panel: the pSHAG-MAGIC vector contains a BseRI restriction site between U6 promoter and Bam HI. The coding sequence was designed to have a BtscI site to generate a compatible end. FIGS. 15B-D show the predicted secondary structures of the three RNA aptamer constructs designated AptER-1×1 (SEQ ID NO: 8), AptER-1×2 (SEQ ID NO: 9), and AptER-4 (SEQ ID NO: 10), respectively. The sequences of three-way junction in AptER-1×2 (FIG. 15C) are shown in lowercase.

FIGS. 18A-C validate aptamer-hERα interaction in vivo by a RNA pull-down assay and an RNA co-immunoprecipitation assay. FIG. 18A shows the localization of SNAP-hERα in living HeLa cells. HeLa cells were transfected with SNAP-hERα expression vector. Twenty-four hours post-transfection, live cells were labeled with SNAP-Cell® TMR-Star and Hoechst 33342. Cells were visualized under inverted fluorescent microscopy using a 63×oil lense. FIG. 18B is an image of a Western blot analysis of SNAP-hERα expressed in HeLa cells. HeLa cells were transfected with SNAP-hERα expression vector. Forty-eight hours post-transfection, cells were harvested and subjected to western blot analysis. SNAP-tagged protein was detected by rabbit anti-SNAP polyclonal antibody. The control is a un-transfected HeLa cell sample. A biotinylated protein ladder (Cell signaling technology) was included. FIG. 18C is an image showing the quantification of AptER-1×2 pull-downed or immunoprecipitated by SNAP-hERα or SNAP. HeLa cells were co-transfected with SNAP-hERα expression vector and pSUPEP/AptER-1×2 expression vector. In the control, SNAP-hERα expression vector was replaced SNAPexpression vector. Forty-eight hours post-transfection, cells were fixed with formaldehyde, and then lyzed by sonication. Cell lysates were incubated with either BG agarose beads (left, pull-down assay) or anti-SNAP antibody coated protein G beads (right, RNA co-IP). The amount of RNA was quantified using real time RT-PCR and expressed as "folds of enrichment" over the amount of RNA isolated in the control. A aliquot of the cell samples were subjected to western blotting to ensure comparable protein expression levels.

DETAILED DESCRIPTION OF THE INVENTION

Figure 1:
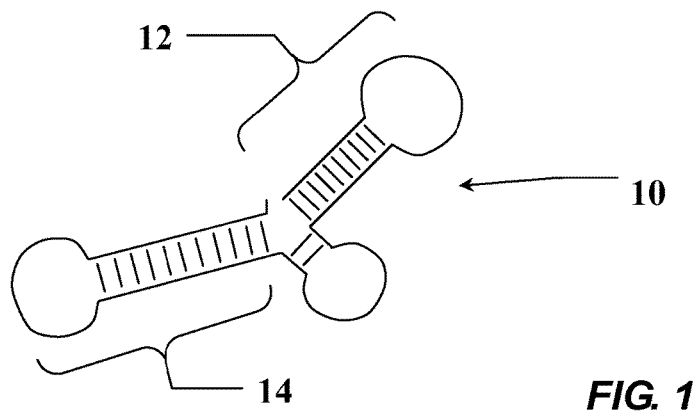
FIG. 1 is a schematic illustration of a therapeutic nucleic acid construct of the present invention, which includes a cancer cell-specific aptamer and an estrogen receptor-specific aptamer of the present invention. The shape of the aptamers is merely illustrative; the aptamer can have any secondary structure that allows it to bind specifically to its target. These therapeutic agents can be targeted to cancer cells for uptake of the construct, allowing the estrogen receptor-specific aptamer to modify estrogen receptor function in the cancer cell.

One aspect of the present invention relates to nucleic acid molecules that are known in the art as aptamers. The aptamers of the present invention possess the capability of binding to estrogen receptors.

As used herein, "estrogen receptor" or "ER" generally refers to mammalian estrogen receptors, including both the alpha-ER (ERα) and the beta-ER (ERβ), regardless of the source organism. While it is intended that the invention applies to any mammalian ER receptor, the human ERα (hERα) and human ERβ (hERβ) are particularly preferred. An exemplary hERα is identified at Genbank Accession Nos. NM_000125 and NP_000116, and an exemplary hERβ is identified at Genbank Accession Nos. NM_001040275 and NP_001035365, each of which is hereby incorporated by reference in its entirety.

Nucleic acid aptamers are characterized by a single-strand and have secondary structure that may possess one or more stems (i.e., base-paired regions) as well as one or more non base-paired regions along the length of the stem. These non base-paired regions can be in the form of a bulge or loop (e.g., internal loop) along the length of the stem(s) and/or a loop at the end of the one or more stem(s) (e.g., hairpin loop). These nucleic acid aptamers possess specificity in binding to a particular target molecule, and they noncovalently bind their target molecule through an interaction such as an ion-ion force, dipole-dipole force, hydrogen bond, van der Waals force, electrostatic interaction, stacking interaction or any combination of these interactions.

Identifying suitable nucleic acid aptamers basically involves selecting aptamers that bind a particular target molecule with sufficiently high affinity (e.g., $K_d$<500 nM) and specificity from a pool or library of nucleic acids containing a random region of varying or predetermined length. For example, identifying suitable nucleic acid aptamers of the present invention can be carried out using an established in vitro selection and amplification scheme known as SELEX. The SELEX scheme is described in detail in U.S. Pat. No. 5,270,163 to Gold et al.; Ellington and Szostak, "In Vitro Selection of RNA Molecules that Bind Specific Ligands," *Nature* 346:818-822 (1990); and Tuerk and Gold, "Systematic Evolution of Ligands by Exponential Enrichment: RNA Ligands to Bacteriophage T4 DNA Polymerase," *Science* 249:505-510 (1990), each of which is hereby incorporated by reference in their entirety. An established template-primer system (Bartel et al., "HIV-1 Rev Regulation Involves Recognition of Non-Watson-Crick Base Pairs in Viral RNA," *Cell* 67:529-536 (1991), which is hereby incorporated by reference in its entirety) can be adapted to produce RNA molecules having a stretch of about 38-40 random bases sandwiched between 5' and 3' constant regions.

The synthetic oligonucleotide templates can be amplified by polymerase chain reaction and then transcribed to generate the original RNA pool. Assuming that ten percent of the RNA molecules are free of chemical lesions that prevent second-strand synthesis and transcription, this pool would contain more than $3 \times 10^3$ different sequences. Because filter binding is applicable for most protein targets, it can be used as the partitioning device, although other suitable schemes can be used. The selected primary RNA aptamers can be cloned into any conventional subcloning vector and sequenced using any variation of the dideoxy method. Next, the secondary structure of each primary RNA aptamer can be predicted by computer programs such as MulFold or mFOLD (Jaeger et al., "Improved Predictions of Secondary Structures for RNA," *Proc. Natl. Acad. Sci. USA* 86:7706-7710 (1989); Zuker, "On Finding All Suboptimal Foldings of an RNA Molecule," *Science* 244:48-52 (1989), each of which is hereby incorporated by reference in its entirety). Mutational studies can be conducted by preparing substitutions or deletions to map both binding sites on the RNA aptamer and its target molecule, as well as to further enhance aptamer binding affinity, as described in the accompanying Examples.

Aptamers generated from SELEX experiments can be optimized to produce second generation aptamers with improved properties (Eaton et al., "Post-SELEX Combinatorial Optimization of Aptamers," *Bioorg. Med Chem.* 5:1087-1096 (1997), which is hereby incorporated by reference in its entirety). Through successive rounds of affinity maturation of a primary SELEX clone, it is possible to obtain aptamers that possess improved affinity for their target as compared to the original clone. Therefore, prior to using aptamers in cell-based experiments, each aptamer can be optimized using the following considerations:

Find the minimal aptamer sequence within the SELEX clone to identify the domain to subject to affinity maturation. This will lead to more desirable, smaller aptamers, which should be better for fusing with alternative functional domains and for in vivo delivery;

It is important to know if the aptamers are selective for their intended estrogen receptor or if they bind indiscriminantly to all estrogen receptors, or even to other nuclear receptors; and Additionally, forming targeted delivery vehicles includes fusing the aptamer sequence with one or more nucleic acid or non-nucleic acid based delivery molecules, optionally with one or more additional estrogen receptor aptamers. This will enhance internal delivery of the estrogen receptor aptamers to cell targets of interest and decrease their off-rate from the estrogen receptor of interest. The formation of these fusion molecules should be possible without impacting the aptamer ability to bind specifically to a particular estrogen receptor of interest.

If any cross-reactivity is observed, then a doped library can be prepared and subjected to "negative selection," also called "counter-SELEX." There is considerable precedent that documents the ability of negative selection to generate aptamers with high degrees of selectivity, even among closely related molecules (Tuerk et al., "Using the SELEX Combinatorial Chemistry Process to Find High Affinity Nucleic Acid Ligands to Target Molecules," *Methods Mol Biol.* 67:219-230 (1997); Rink et al., "Creation of RNA Molecules that Recognize the Oxidative Lesion 7,8-dihydro-8-hydroxy-2'-deoxyguanosine (8-oxodG) in DNA," *Proc Natl Acad Sci USA* 95:11619-11624 (1998); Haller et al., "In vitro Selection of a 7-Methyl-guanosine Binding RNA that Inhibits Translation of Capped mRNA Molecules," *Proc Natl Acad Sci USA* 94:8521-8526 (1997); Edwards et al., "DNA-oligonucleotide Encapsulating Liposomes as a Secondary Signal Amplification Means," *Anal Chem.* 79:1806-1815 (1997), each of which is hereby incorporated by reference in its entirety). To perform negative selection, RNAs bound to receptor-agarose are subjected to a washing step in which the buffer contains other receptor molecules or peptides that replicate one or more binding domains thereof. This results in the elution of aptamers that have undesirable cross-reactivity. The RNAs that remain bound to the agarose beads are then eluted with the estrogen receptor of interest, and amplified as in the classic SELEX procedure. This process is can be repeated until highly selective clones are generated.

Optimization of aptamers can also be achieved during re-selection by using rigorous washing conditions in all steps, including the use of high temperature (37° C. or 45° C.) washing buffers, mild denaturants, and low salt and high salt washes, etc. The proposed stringent washing conditions are intended to select for aptamers that bind more tightly to the estrogen receptor, and thereby improve the over affinity. An additional benefit of generating RNA aptamers that bind with higher affinity to the estrogen receptor is that lower concentrations of therapeutic agents of the present invention will be needed for therapeutic in vivo applications.

Another method to use during optimization is the use of a smaller bias during doping. For example, the library can be doped with a 2:1:1:1 ratio instead of 5:1:1:1. This will result in more library members being substantially different from the parent aptamer.

The SELEX procedure can also be modified so that an entire pool of aptamers with binding affinity can be identified by selectively partitioning the pool of aptamers. This procedure is described in U.S. Patent Application Publication No. 2004/0053310 to Shi et al., which is hereby incorporated by reference in its entirety.

Single stranded DNA aptamers have advantages for in vitro settings due to their ease of synthesis and greater stability. Recent studies have argued that proper buffer conditions and certain RNA sugar modifications can lead to highly stable RNAs (Osborne et al., "Aptamers as Therapeutic and Diagnostic Reagents: Problems and Prospects," *Curr Opin Chem Biol.* 1:5-9 (1997); Faria et al., "Sugar Boost: When Ribose Modifications Improve Oligonucleotide Performance," *Current Opinion in Molecular Therapeutics* 10:168-175 (2008), each of which is hereby incorporated by reference in its entirety). Moreover, as part of the optimization and stabilization process, stabilizing hairpins can be added which markedly enhance aptamer levels in cells (Blind et al., "Cytoplasmic RNA Modulators of an Inside-out Signal-transduction Cascade," *Proc Natl Acad Sci USA* 96:3606-3610 (1999), which is hereby incorporated by reference in its entirety). Regardless, DNA aptamer sequences that bind selectively to estrogen receptors would be inexpensive to synthesize and provide additional assurance of sensor stability in solution phase or microarray-based assays.

SELEX can be performed as readily with DNA as with RNA (Breaker, "DNA Aptamers and DNA Enzymes," *Curr Opin Chem Biol.* 1:26-31 (1997), which is hereby incorporated by reference in its entirety). The absence of a 2'-OH does not substantially impair the ability of DNA to fold or adopt structures. Indeed, SELEX has been used to identify DNAs that bind both small molecules and proteins, with structures that are reminiscent of RNA aptamers. Thus, DNA aptamers can be developed and subjected to analogous mutagenesis and truncation studies to identify suitable estrogen receptor-binding DNA molecules.

As used herein, "nucleic acid" includes both DNA and RNA, in both D and L enantiomeric forms, as well as derivatives thereof (including, but not limited to, 2'-fluoro-, 2'-amino, 2'O-methyl, 5'iodo-, and 5'-bromo-modified polynucleotides). Nucleic acids containing modified nucleotides (Kubik et al., "Isolation and Characterization of 2'fluoro-, 2'amino-, and 2'fluoro-amino-modified RNA Ligands or Human IFN-gamma that Inhibit Receptor Binding," *J. Immunol.* 159:259-267 (1997); Pagratis et al., "Potent 2'-amino, and 2'-fluoro-2'-deoxy-ribonucleotide RNA Inhibitors of Keratinocyte Growth Factor," *Nat. Biotechnol.* 15:68-73 (1997), each which is hereby incorporated by reference in its entirety) and the L-nucleic acids (sometimes termed Spiegelmers®), enantiomeric to natural D-nucleic acids (Klussmann et al., "Mirror-image RNA that Binds D-adenosine," *Nat. Biotechnol.* 14:1112-1115 (1996) and Williams et al., "Bioactive and nuclease-resistant L-DNA Ligand of Vasopressin," *Proc. Natl. Acad. Sci. USA* 94:11285-11290 (1997), each which is hereby incorporated by reference in its entirety), and non-natural bases are used to enhance biostability. In addition, the sugar-phosphate backbone can be replaced with a peptide backbone, forming a peptide nucleic acid (PNA), other natural or non-natural sugars can be used (e.g., 2'-deoxyribose sugars), or phosphothioate or phosphodithioate can be used instead of phosphodiester bonds. The use of locked nucleic acids (LNA) is also contemplated.

One class of aptamer molecules of the present invention (designated as Class I) includes, without limitation, the following aptamers:

```
AptER-1
                                  (SEQ ID NO: 1, see FIG. 5A)
GGGAGAAUUC AACUGCCAUC UAGGCCCACA GUUCAGAGGC
ACCGCGAACA AAACGCAAGA CAGAGUGCCG ACAAGAGCAC
UACAAGCUUC UGGACUCGGU
```

-continued

Figure 13D:
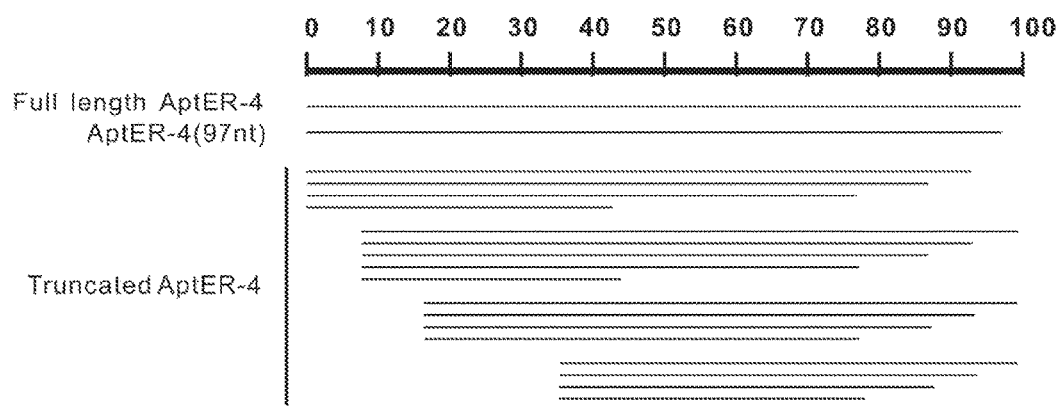
FIG. 13D illustrates the systematic truncation of AptER-4. AptER-4 was truncated from both ends by 8 to 30 nucleotides at a time, yielding a total of seventeen AptER-4 deletion mutants between 42nt and 92nt in length. Primers were designed and the templates were lifted by PCR using the full length AptER-4 as the template. Individual DNA templates were analyzed on 8% native polyacrylamide gel to verify the length. Templates with the same 5' end were grouped and the mixture was used as DNA templates for a RNA transcription reaction. The RNA transcripts in a group were assayed for binding activity using filter-binding assay. None of the truncated AptER-4 shown retained the binding activity.

AptER-2
                    (SEQ ID NO: 2, see FIG. 5B)
GGGAGAAUUC AACUGCCAUC UAGGCACACG CGAGAUAGAG
CGAGGCCUCC AAAAAUGGCC ACGCCAGGAA GCAAGUACUA
CAAGCUUCUG GACUCGGU AptER-3
                    (SEQ ID NO: 3, see FIG. 5C)
GGGAGAAUUC AACUGCCAUC UAGGCGACCC AGGGCCGGGA
CGCAAAGCAG CCAAAACAGA CGGCCCCAGU CAGGGAGUUA
CUACAAGCUU CUGGACUCGG U AptER-1(65nt), or clone sB63,
                    (SEQ ID NO: 5, see FIG. 13A)
GGGCAGAGGC ACCGCGAACA AAACGCAAGA CAGAGUGCCG
ACAAGAGCAC UACAAGCUUC UGCCC AptER-1(53nt)
                    (SEQ ID NO: 6, see FIG. 13B)
GGGCACCGCG AACAAAACGC AAGACAGAGU GCCGACAAGA
GCACUACAAG CCC Clone B30
                    (SEQ ID NO: 11, see FIG. 13C)
GGGAGAAUUC AACUGCCAUC UAGGCCCACA GUUCAGAGGC
ACCGCGAACA CAACGCAAGA CAGAGUGACG ACAAGAGCAC
UACAAGCUUC UGGACUCGGU Clone B65
                    (SEQ ID NO: 12, see FIG. 13C)
GGGAGAAUUC AACUGCCAUC UAGGCCCACA GUUCAGAAGC
ACCGCGAACA AAACGCAAGA CAGAGUGCCG ACAAGAGCAC
UACAAGCUUC UGGACUCGGA Clone sB30
                    (SEQ ID NO: 13, see FIG. 13C)
GGGCAGAGGC ACCGCGAACA CAACGCAAGA CAGAGUGACG
ACAAGAGCAC UACAAGCUUC UGCCC Clone sB65
                    (SEQ ID NO: 14, see FIG. 13C)
GGGCAGAAGC ACCGCGAACA AAACGCAAGA CAGAGUGCCG
ACAAGAGCAC UACAAGCUUC UGCCC ERL5-1
                    (SEQ ID NO: 15)
GGGAGAAUUC AACUGCCAUC UACAAGCCAA GCAAGCGAGC
AAAAAACGCG AGCAUCCGAG CUCCAAGACG UACUACAAGC
UUCUGGACUC GGU ERL5-4
                    (SEQ ID NO: 16)
GGGAGAAUUC AACUGCCAUC UAACAGCCAA GUAAGCGACA
ACGACAAUCA AUGACGCGAA CAAUCCGAAA GAACUACAAG
CUUCUGGACU CGGU ERL5-5
                    (SEQ ID NO: 17)
GGGAGAAUUC AACUGCCAUC UACAGAAGGA CCGCGAGGGU
AAAAACCACG CACGACAGAG UAUAACAAAA GAACUACAAG
CUUCUGGACU CGGU ERL5-6
                    (SEQ ID NO: 18)
GGGAGAAUUC AACUGCCAUC UAAAUGAAAG GACGCACACU
ACGUGCCUA CAAACACAGA AACAAAAACC GAACUACAAG
CUUCUGGACU CGGU The aptamers of Class I are characterized by an ability to bind to both hERα and hERβ, and as evidenced by the activity of AptER-1 and its derivatives this class of aptamers is capable of inhibiting ER transcriptional activity in vivo. Without being bound by belief, it is believed that this inhibition of ER function is the result of preventing ER from recruiting other transcription factors.

Another class of aptamer molecules of the present invention (designated as Class II) includes, without limitation, the following aptamer:

AptER-4
                    (SEQ ID NO: 4, see FIG. 5D)
GGGAGAAUUC AACUGCCAUC UAGGCCACAG CCGGCGGUCG

AACACCAGAG GGCGACUUUG GGUAGUCGAG UAUUAAGUAC

UACAAGCUUC UGGACUCGGU

Unlike Class I aptamer molecules which bind to both hERα and hERβ, this class binds to a distinct site on hERα and exhibits selectivity in binding hERα with negligible binding to hERβ. As evidenced by the activity of AptER-4, this class of aptamers is capable of inhibiting ER transcriptional activity in vivo. Without being bound by belief, it is believed that this inhibition of ER function is the result of preventing ER from recruiting other transcription factors.

In certain embodiments of the present invention, the estrogen receptor-binding aptamer is selective for one estrogen receptor over another. Thus, aptamers can be designed for selectivity to ER-α over the ER-β and other nuclear receptors, or for selectivity to ER-β over the ER-α and other nuclear receptors. AptER-4 (FIG. 5D, SEQ ID NO: 4) represents one such example of this selectivity, because it has selectivity for hER-α over hER-β (see FIG. 8D).

In certain embodiments of the present invention, the estrogen receptor-binding aptamer reversibly binds to the estrogen receptor with a dissociation constant ($K_d$) of less than about 50 nM, preferably less than about 40 nM or 30 nM, more preferably less than about 25 nM or 20 nM. Optimization of the aptamer sequences should afford enhanced binding affinity, and dissociation constants of less than about 15 nM or 10 nM, or even 5 nM.

Increasing the number of aptamer domains in a single molecule, i.e., a multivalent aptamer, also is shown to decrease the dissociation of the aptamer from its target. Therefore, the present invention also contemplates aptamer constructs that include a series of estrogen receptor-binding aptamers that are joined together by linking nucleotides sequences that do not adversely affect the secondary structure of the individual aptamer domains. Multivalent aptamers of this type can be constructed as described in Shi et al., "RNA Aptamers as Effective Protein Antagonists in a Multicellular Organism," *Proc Natl Acad Sci USA* 96(18): 10033-10038 (1999) (describing pentavalent aptamer constructs); Xu and Shi, "Composite RNA Aptamers as Functional Mimics of Proteins," *Nucl Acids Res* 37(9): 1-9 (2009) (describing di-dimeric aptamer construct with three-way junction); U.S. Patent Application Publ. No. 20050282190 to Shi et al. (describing multimeric aptamer constructs containing three-way junctions), each of which is hereby incorporated by reference in its entirety. Before joining two functional RNA molecules, it is often beneficial to first predict the 15 secondary structures of the chimeric nucleic acid molecule to ensure that their combination is unlikely to disrupt their secondary structures. Secondary structure predictions can be performed using a variety of software including, without limitation, RNA Structure Program (Dr. David Mathews, University of Rochester) and MFold (Dr. Michael Zuker, The RNA Institute, SUNY at Albany), among others. In certain embodiments, the aptamer domains can bind to the same binding site on the estrogen receptor. In alternative embodiments, the aptamer domains can bind to more than one distinct site on the estrogen receptor.

According to another aspect of the present invention, the nucleic acid aptamer molecules of the present invention can include one or more additional functional domains that are distinct of the estrogen receptor-binding domains. In one embodiment, the additional functional domain can be directed to a cell surface antigen (or marker) that will allow for uptake of the aptamer construct into a particular target cell where estrogen receptor activity can be modulated.

A number of high affinity cancer cell-targeting aptamers have been identified including, without limitation, the following:

(1) Aptamer A30 (UAAUACGACUCAC-UAUAGGGAAUUCCGCGUGUGCCA GCGAAAGUUGCGUAUGGGUCACAUCGCAG-GCACAUGUCAUCUGGGC GGUC-CGUUCGGGAUCCUC, SEQ ID NO: 19), which binds specifically to the oligomeric state of the extracellular domain of human epidermal growth factor receptor-3 (HER3) which is overexpressed in breast cancer cells (Chen et al., "Inhibition of Heregulin Signaling by an Aptamer that Preferentially Binds to the Oligomeric Form of Human Epidermal Growth Factor Receptor-3," *Proc. Natl. Acad. Sci. USA* 100(16):9226-9231 (2003), which is hereby incorporated by reference in its entirety);

(2) Aptamer to Her-2 (AGCCGC-GAGGGGAGGGAUAGGGUAGGGCGCGGCU, SEQ ID NO: 20), which binds specifically to the extracellular domain human epidermal growth factor receptor-2 (HER2) which is overexpressed in breast cancer cells (Kim et al., "In vitro Selection of RNA Aptamer and Specific Targeting of ErbB2 in Breast Cancer Cells," *Nucleic Acid Ther.* 21(3): 173-178 (2011), which is hereby incorporated by reference in its entirety);

(3) Aptamer S6 (GGGAGAUACCAGCUUAUU-CAAUUUGGAUGGGGAGAUC CGUUGA-GUAAGCGGGCGUGUCUCUCUGCCGCCUUGC-UAUGGGGAGA UAGUAAGUGCAAUCU, SEQ ID NO: 21), which binds specifically to HER-2 overexpressing breast cancer cells (Kang et al., "Isolation of RNA Aptamers Targeting HER-2-overexpressing Breast Cancer Cells Using Cell-SELEX," *Bull. Korean Chem. Soc.* 30(8): 1827-1831 (2009), which is hereby incorporated by reference in its entirety); and (4) Aptamer aptTOV 1 (UCCAGAGUGACGCAGCA-GAUCUGUGUAGGAUCG CAGUGUAGUGGA-CAUUUGAUACGACUGGCUCGACACGGUGGC-UUA, SEQ ID NO: 22), which binds with high affinity to the ovarian clear cell carcinoma cell line TOV-21G (Van Simaeys et al., "Study of the Molecular Recognition of Aptamers Selected through Ovarian Cancer Cell-SELEX," *Plos One* 5(11):e13770 (2010), which is hereby incorporated by reference in its entirety).

In accordance with other embodiments, the additional functional domain can be directed to a location/localization element that directs the specific aptamer construct to a particular specific subcellular compartment; and stabilization sequences that stabilize the aptamer construct and/or resist its degradation.

For aptamer constructs expressed in vivo in an ER-positive cancer cell, in one embodiment the aptamer can be retained within the nucleus. In alternative embodiments, the aptamer can be targeted explicitly for nuclear export (i.e., to allow the aptamer to interact with estrogen receptors outside the nucleus). For the latter approach, specific nucleic acid sequence or structure, such as the Constitutive Transport Element of the type D retrovirus (Bray et al., "A Small Element from the Mason-Pfizer Monkey Virus Genome Makes Human Immunodeficiency Virus Type I Expression and Replication Rev-Independent," *Proc. Natl. Acad. Sci. USA* 91:1256-1260 (1994): Ernst et al., "A Structured Retroviral RNA Element that Mediates Nucleocytoplasmic Export of Intron-Containing RNA," *Mol. Cell. Biol.* 17:135-144(1997), which are hereby incorporated by reference in their entirety) can be appended to the aptamer molecule as a nucleic acid element.

One example of a stabilization sequence is an exonuclease-blocking sequence linked to an aptamer sequence. In particular, a stable tetra-loop near the 3' end of the aptamer can be engineered. Because of its highly stacked and relatively inaccessible structure, the UUCG tetra-loop (Cheong et al., "Solution Structure of an Unusually Stable RNA Hairpin . . . ," *Nature* 346:680-682 (1990), which is hereby incorporated by reference in its entirety) can be used to stabilize nucleic acid molecules against degradation by 3' exonucleases and to serve as a nucleation site for folding (Varani, "Exceptionally Stable Nucleic Acid Hairpins," *Annu. Rev. Biophys. Biomol. Struct.* 24:379-404 (1995), which is hereby incorporated by reference in its entirety). Structurally, this type of loop is also used as a "U-turn" to close a stem region to make the strand continuous as a single molecular entity. Suitable U-turns for RNA include, without limitation, members of the UNCG and GNRA tetraloop families (Varani, "Exceptionally Stable Nucleic Acid Hairpins," *Annu. Rev. Biophys. Biomol. Struct.* 24:379-404 (1995), which is hereby incorporated by reference in its entirety). Suitable U-turns for DNA include, without limitation, members of the GNRA tetraloop family (Varani, "Exceptionally Stable Nucleic Acid Hairpins," *Annu. Rev. Biophys. Biomol. Struct.* 24:379-404 (1995), which is hereby incorporated by reference in its entirety).

Another example of a stabilization sequence is an "S35 motif" which yields a virtually closed structure resistant to nucleolytic degradation. The S35 motif, constructed by creating complementary 5' and 3' ends, has been shown to cause an over 100-fold increase in accumulation of a tRNA-ribozyme chimerical transcript in stably transduced cell lines (Thompson et al., "Improved Accumulation and Activity of Ribozymes Expressed from a tRNA-Based RNA Polymerase III Promoter," *Nucleic Acids Res.* 23:2259-2268 (1995), which is hereby incorporated by reference in its entirety). Its use with in vivo aptamer expression has been demonstrated previously. See Shi et al., "A Specific RNA Hairpin Loop Structure Binds the RNA Recognition Motifs of the *Drosophila* SR Protein B52," *Mol Cell Biol* 17(5): 2649-2657 (1997); U.S. Pat. No. 6,458,559 to Shi et al., each of which is hereby incorporated by reference in its entirety.

Another type of functional nucleic acid element is a catalytic element, such as a ribozyme, including a cis-acting ribozyme. In forming a transcriptional product that is a multimer, the transcript in its immature form contains multiple aptamer constructs joined together, and the aptamer constructs include a cis-acting ribozyme that can self-cleave the transcript to release each mature aptamer construct. Each of the mature aptamer constructs contains at least one of the aptamer molecules of the present invention. This use of the cis-acting ribozymes is described and illustrated in Shi et al., "A Specific RNA Hairpin Loop Structure Binds the RNA Recognition Motifs of the *Drosophila* SR Protein B52," *Mol Cell Biol* 17(5):2649-2657 (1997); and U.S. Pat. No. 6,458, 559 to Shi et al., each of which is hereby incorporated by reference in its entirety.

Before joining two functional RNA molecules, it is often beneficial to first predict the secondary structures of the chimeric nucleic acid molecule to ensure that their combination is unlikely to disrupt their secondary structures. Secondary structure predictions can be performed using a variety of software including, without limitation, RNA Structure Program (Dr. David Mathews, University of Rochester) and MFold (Dr. Michael Zuker, The RNA Institute, SUNY at Albany), among others. If the secondary structure predictions suggest no problems, then the chimeric nucleic acid molecules can be generated. Double-stranded DNA templates can be prepared by cloning their PCR products into a cloning vector and using the clones as templates for PCR with the appropriate primers (e.g., 5' primer for one aptamer portion and 3' primer for the other aptamer portion). These same primers can be used to generate the chimeric DNA template for transcription, and in vitro transcription can be carried out using standard procedures to obtain the RNA chimeras, which can then be gel purified prior to use.

While the RNA aptamer molecules of the present invention can be synthesized from chemical precursor, they also can be prepared either in vitro or in vivo using recombinant templates or constructs, including transgenes, that encode the RNA aptamer molecules of the present invention. Whether using in vitro transcription or transgenes suitable for expression in vivo, these genetic constructs can be prepared using well known recombinant techniques. Thus, a further aspect of the present invention relates to a constructed DNA molecule that includes a first region encoding an RNA aptamer molecule of the invention.

According to one embodiment, the constructed DNA molecule encodes an RNA fusion product. Such a product is formed by joining together one piece of DNA encoding an RNA aptamer molecule of the present invention and a second piece of DNA encoding an additional functional domain of the type described above. As described above, the RNA aptamer molecule can be in the form of a multivalent construct containing two or more aptamers that bind to the estrogen receptor, or a concatamer containing multiple repeats of the entire functional molecule.

Preparation of the DNA molecule can be carried out by well-known methods of DNA ligation. DNA ligation utilizes DNA ligase enzymes to covalently link or ligate fragments of DNA together by catalyzing formation of a phosphodiester bond between the 5' phosphate of one strand of DNA and the 3' hydroxyl of another. Typically, ligation reactions require a strong reducing environment and ATP. The commonly used T4 DNA ligase is an exemplary DNA ligase in preparing the DNA molecule of the present invention. Once the DNA molecule of the present invention has been constructed, it can be transcribed in vitro or incorporated into host cells as described infra.

Transcription of the DNA molecule of the present invention is often dependent upon the presence of a promoter, which is a DNA sequence that directs the binding of RNA polymerase and thereby promotes RNA synthesis. Accordingly, the DNA molecule of the present invention may include a promoter operably coupled to the first region to control expression of the RNA aptamer. Because not all polymerases require promoters, particularly during in vitro transcription, the promoter sequence is optional.

The DNA sequences of eukaryotic promoters differ from those of prokaryotic promoters. Furthermore, eukaryotic promoters and accompanying genetic signals may not be recognized in or may not function in a prokaryotic system and, further, prokaryotic promoters are not recognized and do not function in eukaryotic cells.

Promoters vary in their "strength" (i.e., their ability to promote transcription). Depending on the application, it may be desirable to use strong promoters in order to obtain a high level of transcription.

Depending upon the host cell system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promoter unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

As described above, one type of regulatory sequence is a promoter located upstream or 5' to the coding sequence of the DNA molecule. Depending upon the desired activity, it is possible to select the promoter for not only in vitro production of the RNA aptamer, but also in vivo production in cultured cells or whole organisms, as described below. Because in vivo production can be regulated genetically, another suitable class of promoters is an inducible promoter which induces transcription of the DNA molecule in response to specific conditions, thereby enabling expression of the RNA aptamer as desired (i.e., expression within specific tissues, or at specific temporal and/or developmental stages). The various promoter types can be driven by RNA polymerases I, II, or III.

Suitable promoters for use with the constructed DNA molecule of the present invention include, without limitation, a T7 promoter, a SUP4 tRNA promoter, an RPR1 promoter, a GPD promoter, a GAL1 promoter, an hsp70 or hic promoter, an Mtn promoter, a UAShs promoter, SV40 promoter, MMTV promoter, metallothionine-1 promoter, adenovirus E1a promoter, CMV immediate early, tRNA promoter, 5S rRNA promoter, U6 promoter, and H1 promoter (Shi et al., "RNA Aptamers as Effective Protein Antagonists in a Multicellular Organism," *Proc Natl Acad Sci USA* 96(18):10033-10038 (1999); Wang et al., "Knocking Down Gene Function with an RNA Aptamer Expressed as Part of an Intron," *Nucleic Acids Res* 38(15):e154 (2010); Que-Gewirth and Sullenger, "Gene Therapy Progress and Prospects: RNA Aptamers," *Gene Ther* 14(4):283-291 (2007), which is hereby incorporated by reference in its entirety), and functional fragments thereof The T7 promoter is a well-defined, short DNA sequence that can be recognized and utilized by T7 RNA polymerase of the bacteriophage T7. The T7 RNA polymerase can be purified in large scale and is commercially available. The transcription reaction with T7 promoter can be conducted in vitro to produce a large amount of the molecular complex of the present invention (Milligan et al., "Oligoribonucleotide Synthesis Using T7 RNA Polymerase and Synthetic DNA Templates," *Nucleic Acids Res.* 15(21):8783-8798 (1987), which is hereby incorporated by reference in its entirety). The T7 RNA polymerase can also be used in mammalian and bacterial cells to produce very high levels of RNA. The SUP4 tRNA promoter and RPR1 promoter are driven by RNA polymerase III of the yeast *Saccharomyces cerevisiae*, and suitable for high level expression of RNA less than 400 nucleotides in length (Kurjan et al., Mutation at the Yeast SUP4 tRNA$^{tyr}$ Locus: DNA Sequence Changes in Mutants Lacking Suppressor Activity," *Cell* 20:701-709 (1980); Lee et al., "Expression of RNase P RNA in *Saccharomyces*

*cerevisiae* is Controlled by an Unusual RNA Polymerase III Promoter," *Proc. Natl. Acad. Sci. USA* 88:6986-6990 (1991), each of which is hereby incorporated by reference in its entirety). The glyceraldehyde-3-phosphate dehydrogenase (GPD) promoter in yeast is a strong constitutive promoter driven by RNA polymerase II (Bitter et al., "Expression of Heterologous Genes in *Saccharomyces cerevisiae* from Vectors Utilizing the Glyceraldehyde-3-phosphate Dehydrogenase Gene Promoter," *Gene* 32:263-274 (1984), which is hereby incorporated by reference in its entirety). The galactokinase (GAL1) promoter in yeast is a highly inducible promoter driven by RNA polymerase II (Johnston and Davis, "Sequences that Regulate the Divergent GAL1-GAL10 Promoter in *Saccharomyces cerevisiae,*" *Mol. Cell. Biol.* 4:1440-1448 (1984), which is hereby incorporated by reference in its entirety). The heat shock promoters are heat inducible promoters driven by the RNA polymerase II in eukaryotes. The frequency with which RNA polymerase II transcribes the major heat shock genes can be increased rapidly in minutes over 100-fold upon heat shock. Another inducible promoter driven by RNA polymerase II that can be used in the present invention is a metallothionine (Mtn) promoter, which is inducible to the similar degree as the heat shock promoter in a time course of hours (Stuart et al., "A 12-Base-Pair Motif that is Repeated Several Times in Metallothionine Gene Promoters Confers Metal Regulation to a Heterologous Gene," *Proc. Natl. Acad. Sci. USA* 81:7318-7322 (1984), which is hereby incorporated by reference in its entirety).

Spatial control of an RNA molecule can be achieved by tissue-specific promoters, which have to be driven by the RNA polymerase II. The many types of cells in animals are created largely through mechanisms that cause different genes to be transcribed in different cells, and many specialized animal cells can maintain their unique character when grown in culture. The tissue-specific promoters involved in such special gene switching mechanisms, which are driven by RNA polymerase II, can be used to drive the transcription templates that code for the molecular complex of the present invention, providing a means to restrict the expression of the molecular complex in particular tissues. Any of a variety of tissue-specific promoters can be selected as desired. For example, promoters selective for expression in breast cancer include the α-lactalbumin, cyclo-oxygenase 2, telomerase, and multidrug resistance (Bauerschmitz et al., "Tissue-Specific Promoters Active in CD44$^+$CD24$^-$/flow Breast Cancer Cells," *Cancer Res* 68(14):5533-9 (2008), which is hereby incorporated by reference in its entirety).

Another type of regulatory sequence is known as an enhancer. Enhancer elements do not need to be located immediately upstream of the promoter or the sequence which encodes the transcript that will be made. Enhancers can, in fact, be located very far away. Nevertheless, they can also serve as regulatory elements, and could potentially be regulated by signaling molecules and thereby influence the expression of a target RNA inside a cell. Exemplary enhancer elements include, without limitation, the well-known SV40 enhancer region and the 35S enhancer element.

Termination of transcription in eukaryotic genes involves cleavage at a specific site in the RNA which may precede termination of transcription. Also, eukaryotic termination varies depending on the RNA polymerase that transcribes the gene. However, selection of suitable 3' transcription termination regions is well known in the art and can be performed with routine skill.

Once the DNA molecule of the present invention has been constructed, it can be incorporated into cells using conventional recombinant DNA technology. Generally, this involves inserting the DNA molecule into an expression system to which the DNA molecule is heterologous (i.e., not normally present). The heterologous DNA molecule is inserted into the expression system or vector in proper sense orientation. The vector contains the necessary elements for their persistent existence inside cells and for the transcription of an RNA molecule of the present invention.

U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. See also Maniatis et al., *Molecular Cloning: A Laboratory Manual*, Cold Springs Laboratory, Cold Springs Harbor, New York (1982), which is hereby incorporated by reference in its entirety. These recombinant plasmids are then introduced by means of transformation and transfection, and replicated in cultures including prokaryotic organisms and eukaryotic cells grown in tissue culture.

Recombinant viruses can be generated by transfection of plasmids into cells infected with virus. Suitable vectors include, but are not limited to, the following viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK+/- or KS+/- (see "Stratagene Cloning Systems" Catalog (1993) from Stratagene, La Jolla, Calif, which is hereby incorporated by reference in its entirety), pQE, pIH821, pGEX, pET series (see Studier et al., "Use of T7 RNA Polymerase to Direct Expression of Cloned Genes," *Gene Expression Technology*, vol. 185 (1990), which is hereby incorporated by reference in its entirety), pIIIEx426 RPR, pIIIEx426 tRNA (see Good and Engelke, "Yeast Expression Vectors Using RNA Polymerase III Promoters," *Gene* 151:209-214 (1994), which is hereby incorporated by reference in its entirety), p426GPD (see Mumberg et al., "Yeast Vectors for the Controlled Expression of Heterologous Proteins in Different Genetic Background," *Gene* 156:119-122 (1995), which is hereby incorporated by reference in its entirety), p426GAL1 (see Mumberg et al., "Regulatable Promoters of *Saccharomyces cerevisiae*: Comparison of Transcriptional Activity and Their Use for Heterologous Expression," *Nucl. Acids Res.* 22:5767-5768 (1994), which is hereby incorporated by reference in its entirety), pUAST (see Brand and Perrimon, "Targeted Gene Expression as a Means of Altering Cell Fates and Generating Dominant Phenotypes," *Development* 118:401-415 (1993), which is hereby incorporated by reference in its entirety), and any derivatives thereof. Suitable vectors are continually being developed and identified.

A variety of host-vector systems may be utilized to express the DNA molecule. Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, adeno-associated virus, retroviral vectors, etc.); insect cell systems infected with virus (e.g., baculovirus). The expression elements of these vectors vary in their strength and specificities. Depending upon the host-vector system utilized, any one of a number of suitable transcription elements can be used. The host cell is preferably present either in a cell culture (ex vivo) or in a whole living organism (in vivo).

Incorporation of the DNA construct into a host cell can be carried out by various forms of transformation, depending upon the vector/host cell system such as transformation, transduction, conjugation, mobilization, electroporation, microinjection, or infective transformation.

Mammalian cells suitable for carrying out the present invention include, without limitation, COS (e.g., ATCC No. CRL 1650 or 1651), BHK (e.g., ATCC No. CRL 6281), CHO (ATCC No. CCL 61), HeLa (e.g., ATCC No. CCL 2), 293 (ATCC No. 1573), CHOP, NS-1 cells, embryonic stem cells, induced pluripotent stem cells, and primary cells recovered directly from a mammalian organism. With regard to primary cells recovered from a mammalian organism, these cells can optionally be reintroduced into the mammal from which they were harvested or into other animals. For in vivo therapeutic approaches discussed below, estrogen receptor-dependent cancer cells are particularly desired.

The expression of high levels of functional RNA aptamers within cells can be complicated by several factors including RNA stability, short half-life, and difficulties in cellular targeting. Nonetheless, substantial progress has been achieved over the last several years. The first demonstration of aptamer function in live cells involved nuclear targets (Klug et al., "In Vitro and In Vivo Characterization of Novel mRNA Motifs that Bind Special Elongation Factor SelB," *Proc. Natl. Acad. Sci. USA* 94:6676-6681 (1997); Shi et al., "RNA Aptamers as Effective Protein Antagonists In a Multicellular Organism," *Proc. Natl. Acad. Sci. USA* 96:10033-10038 (1999); Thomas et al., "Selective Targeting and Inhibition of Yeast RNA Polymerase II by RNA Aptamers," *J. Biol. Chem.* 272: 27980-27986 (1997), which are hereby incorporated by reference in their entirety). Aptamer function within the nucleus of mammalian cells has also been demonstrated (Symensma et al., "Polyvalent Rev Decoys Act as Artificial Rev-Responsive Elements," *J. Virol.* 73:4341-4349 (1999), which is hereby incorporated by reference in its entirety). More recently, effective strategies for cytoplasmic targeting of aptamer have also been developed. For example, the human tRNA initiator sequence, which mediates highly efficient nuclear export to deliver functional chimeric RNA aptamers to the cytosol has been used (Chaloin et al., "Endogenous Expression of a High-Affinity Pseudoknot RNA Aptamer Suppresses Replication of HIV-1," *Nucl. Acids Res.* 30:4001-4008 (2002), which is hereby incorporated by reference in its entirety). Functional RNA aptamers have also been directly delivered to the cytoplasm by lipofection (Theis et al., "Discriminatory Aptamer Reveals Serum Response Element Transcription Regulated by Cytohesin-2," *Proc. Natl. Acad. Sci. USA* 101:11221-11226 (2004), which is hereby incorporated by reference in its entirety). Finally, very high levels of aptamer expression ($1 \times 10^7$ molecules per cell) have been achieved by fusion with a highly stable transcript (Choi et al., "Intracellular Expression of the T-cell Factor-1 RNA Aptamer as an Intramer," *Mol. Cancer Ther* 5:2428-2434 (2006), which is hereby incorporated by reference in its entirety).

Infective transformation systems can also be utilized to express the RNA molecule in mammalian cells in vivo.

To produce an intramer directly in the relevant cellular compartment, e.g., for cytoplasmic delivery of an RNA aptamer, Blind et al. developed a vaccinia virus-based RNA expression system based on double infection with two recombinant vaccinia viruses encoding T7 polymerase and aptamer, respectively, to achieve high-level cytoplasmic expression of RNA aptamers directed against the intracellular domain of the human $\alpha_L\beta_2$-integrin (Famulok et al., "Intramers as Promising New Tools in Functional Proteomics," *Chem Biol* 8(10):931-939 (2001), which is hereby incorporated by reference in its entirety). For intra-nucleus targeting, RNA expression vectors with Pol III U6 or H1 have been successfully used to express short-hairpin (shRNA) (Paddison et al., "A Resource for Large-scale RNA-interference-based Screens in Mammals," *Nature* 428 (6981):427-431 (2004), which is hereby incorporated by reference in its entirety) and RNA aptamers (Mi et al., "HI RNA Polymerase III Promoter-driven Expression of an RNA Aptamer Leads to High-level Inhibition of Intracellular Protein Activity," *Nucleic Acids Res* 34(12):3577-3584 (2006), which is hereby incorporated by reference in its entirety) in mammalian cells. There are several advantages of using these two RNA pol III systems, such as high transcription level, nuclear distribution of expressed RNA and uniform RNA molecules containing defined 5' and 3' ends. Intracellular expressed aptamer can also be transported through the nuclear pore complex to a specific cellular compartment by fusing to nucleic acid-based exportin or importin (Grimm et al., "In vivo Selection of RNAs that Localize in the Nucleus," *EMBO J* 16(4):793-806 (1997); Hamm and Fornerod, "Anti-idiotype RNAs that Mimic the Leucine-rich Nuclear Export Signal and Specifically Bind to CRM1/exportin 1," *Chem Biol* 7(5):345-354 (2000), each of which is hereby incorporated by reference in its entirety.

Adenovirus gene delivery vehicles can be readily prepared and utilized given the disclosure provided in Berkner, "Development of Adenovirus Vectors for the Expression of Heterologous Genes," *Biotechniques* 6:616-29 (1988); Rosenfeld et al., "Adenovirus-mediated Transfer of a Recombinant α1-Antitrypsin Gene to the Lung Epithelium in vivo," *Science* 252:431-434 (1991), WO 1993/007283 to Curiel et al., WO 1993/006223 to Perricaudet et al., and WO 1993/007282 to Curiel et al., which are hereby incorporated by reference in their entirety. Additional types of adenovirus vectors are described in U.S. Pat. No. 6,057,155 to Wickham et al., U.S. Pat. No. 6,033,908 to Bout & Hoeben, U.S. Pat. No. 6,001,557 to Wilson et al., U.S. Pat. No. 5,994,132 to Chamberlain & Kumar-Singh, U.S. Pat. No. 5,981,225 to Kochanek & Schniedner, U.S. Pat. No. 5,885,808 to Spooner & Epenetos, and U.S. Pat. No. 5,871,727 to Curiel, which are hereby incorporated by reference in their entirety.

Adeno-associated viral gene delivery vehicles can be constructed and used to deliver into cells a recombinant gene encoding a desired nucleic acid aptamer construct. The use of adeno-associated viral gene delivery vehicles in vitro is described in Chatterjee et al., "Dual-Target Inhibition of HIV-1 in vitro by Means of an Adeno-associated Virus Antisense Vector," *Science* 258:1485-8 (1992), Walsh et al., "Regulated High Level Expression of a Human γ-Globin Gene Introduced into Erythroid Cells by an Adeno-Associated Virus Vector," *Proc Nat'l Acad Sci USA* 89:7257-61 (1992), Walsh et al., "Phenotypic Correction of Fanconi Anemia in Human Hematopoietic Cells with a Recombinant Adeno-Associated Virus Vector," *J Clin Invest* 94:1440-8 (1994), Flotte et al., "Expression of the Cystic Fibrosis Transmembrane Conductance Regulator from a Novel Adeno-Associated Virus Promoter,"*J Biol Chem* 268:3781-90 (1993), Ponnazhagan et al., "Suppression of Human α-Globin Gene Expression Mediated by the Recombinant Adeno-Associated Virus 2-based Antisense Vectors," *J Exp Med* 179:733-8 (1994), Miller et al., "Recombinant Adeno-Associated Virus (rAAV)-Mediated Expression of a Human γ-Globin Gene in Human Progenitor-Derived Erythroid Cells," *Proc Nat'l Acad Sci USA* 91:10183-7 (1994), Einerhand et al., "Regulated High-Level Human β-Globin Gene Expression in Erythroid Cells Following Recombinant Adeno-Associated Virus-Mediated Gene Transfer," *Gene Ther* 2:336-43 (1995), Luo et al., "Adeno-Associated Virus 2-Mediated Gene Transfer and Functional Expression of the Human Granulocyte-Macrophage Colony-Stimulating Factor," *Exp Hematol* 23:1261-7 (1995), and Zhou et al., "Adeno-Associated Virus 2-Mediated Transduction and Erythroid Cell-Specific Expression of a Human β-Globin Gene," *Gene Ther* 3:223-9 (1996), which are hereby incorporated by reference in their entirety. In vivo use of these vehicles is described in Flotte et al., "Stable in vivo Expression of the Cystic Fibrosis Transmembrane Conductance Regulator with an Adeno-Associated Virus Vector," *Proc Nat'l Acad Sci USA* 90:10613-7 (1993), and Kaplitt et al., "Long-Term Gene Expression and Phenotypic Correction Using Adeno-Associated Virus Vectors in the Mammalian Brain," *Nat Genet* 8:148-54 (1994), which are hereby incorporated by reference in their entirety.

Retroviral vectors which have been modified to form infective transformation systems can also be used to deliver a recombinant gene encoding a desired nucleic acid aptamer construct into a target cell. One such type of retroviral vector is disclosed in U.S. Pat. No. 5,849,586 to Kriegler & Perez, which is hereby incorporated by reference in its entirety. Lentivirus vectors can also be utilized, including those described in U.S. Pat. No. 6,790,657 to Arya, U.S. Patent Application Publication No. 2004/0170962 to Kafri et al., and U.S. Patent Application Publication No. 2004/0147026 to Arya, which are hereby incorporated by reference in their entirety.

A further aspect of the invention relates to molecular complexes that are formed using the nucleic acid aptamers of the present invention, which are specifically bound to the estrogen receptor, i.e., either the ERα or ERβ as described herein. Specific examples of these types of molecular complexes, formed in vitro and in vivo, are disclosed in the accompanying Examples. Although in vitro host cells are described in the accompanying Examples, it should be appreciated to those of skilled in the art that the host cells can be present in an individual, particularly an individual being treated in a manner whereby estrogen receptor activity is modulated for therapeutic purposes.

Yet another aspect of the present invention relates to a method of inhibiting estrogen receptor activity in a cell. This is carried out by contacting an estrogen receptor in a cell with a nucleic acid aptamer molecule according to the present invention, whereby the nucleic acid aptamer molecule binds to the estrogen receptor and inhibits activity thereof. The estrogen receptor activity that is inhibited can be transcriptional activation, nuclear signaling, or both. As demonstrated in the accompanying examples, transcriptional activation levels of the estrogen receptor can be inhibited by at least about 30 to about 50 percent in the cell. It is believed that enhanced aptamer expression should be able to inhibit estrogen receptor transcriptional activation levels by greater than about 50 or about 60 percent, preferably greater than about 70 or about 80 percent, most preferably greater than about 90 or about 95 percent.

In this aspect of the invention, the cell can be any mammalian cell, but preferably the cell is a cancer cell that is estrogen receptor positive. Exemplary estrogen receptor positive cancer cells include, without limitation, breast cancer cells, ovarian cancer cells, uterine cancer cells, endometrial cancer cells, or any combination thereof.

In certain embodiments, the nucleic acid aptamer molecule is prepared in vitro and delivered into the cell prior to contacting the estrogen receptor. A number of different approaches are available to deliver the aptamer into the cell. According to one approach, the aptamer is contained within a delivery vehicle in the form of a cationic polymer, modified cationic polymer, peptide molecular transporter, lipid, liposome and/or non-cationic polymer. The delivery vehicle is preferably targeted to the cell type of interest where estrogen receptor activity is to be modulated.

According to another approach, the nucleic acid aptamer molecule is one component of a molecular delivery agent that also includes a cell targeting component that is covalently or non-covalently linked to the nucleic acid aptamer molecule. The cell targeting component can be another aptamer, an antibody or binding fragment thereof, or an antibody mimic that is specific for a cell surface molecule that is present on the target cell type. According to this approach, the cell targeting component binds to a cell surface molecule on the target cell type, and the molecular delivery agent is taken up by the cell and the nucleic acid aptamer molecule is internalized into the cell where it can bind to the estrogen receptor and inhibit its activity.

One example of the molecular delivery agent is a multifunctional domain aptamer molecule, which is illustrated in FIG. 1. According to one embodiment of the agent of FIG. 1 includes a HER2 or HER3 breast cancer cell-specific aptamer 12 and an estrogen receptor-specific aptamer 14 of the present invention, which is targeted to breast cancer cells expressing HER2. Upon binding of the aptamer to the HER2- or HER3-expressing breast cancer cell, the cancer cell will take up the molecule and the estrogen receptor-specific aptamer 14 will interfere with estrogen receptor signaling. The disruption of estrogen receptor signaling will diminish both proliferation and survival of the targeted breast cancer cell. This type of molecule can optionally be modified with stability enhancing elements of the type described above.

A further embodiment of the molecular delivery agent of FIG. 1 includes an aptamer that targets ovarian clear cell carcinoma cells and an estrogen receptor-specific aptamer, which is targeted to ovarian clear cell carcinomas. Upon binding of the aptamer to the ovarian clear cell carcinoma, the cancer cell will take up the molecule and the estrogen receptor-specific aptamer 14 will interfere with estrogen receptor signaling. Disruption of estrogen receptor signaling will diminish both proliferation and survival of the targeted ovarian cancer cell. This type of molecule can optionally be modified with stability enhancing elements of the type described above.

Figure 2:
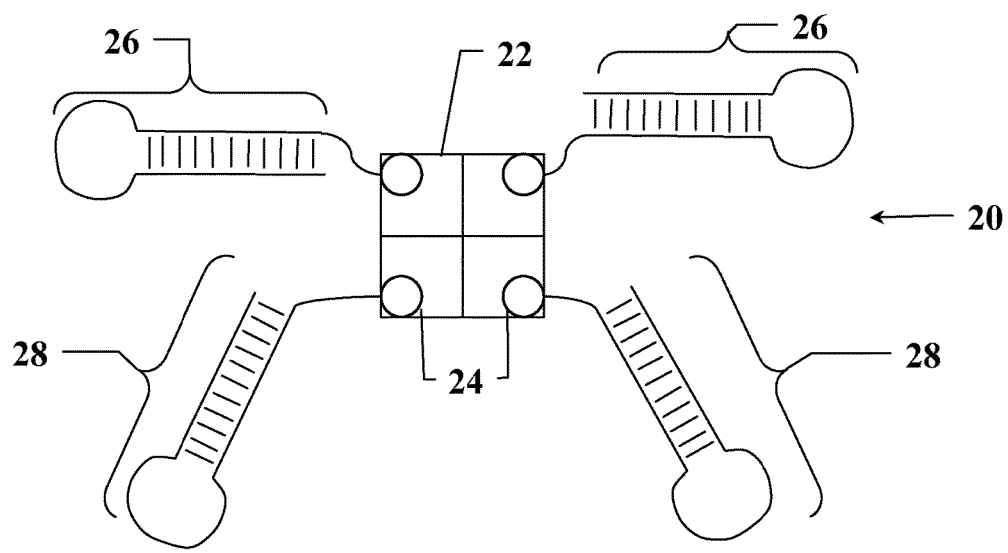
FIG. 2 is a schematic illustration of a therapeutic nucleic acid construct of the present invention, which includes one or more estrogen receptor-specific aptamers and one or more cancer cell-specific binding aptamers (two of each are present in the embodiment shown). The shape of the aptamers is merely illustrative; the aptamer can have any secondary structure that allows it to bind specifically to its target. These therapeutic agents can be targeted to cancer cells for uptake of the construct, allowing the estrogen receptor-specific aptamer to modify estrogen receptor function in the cancer cell.

Another example of the molecular delivery agent is a conjugated aptamer molecule 20 of the type illustrated in FIG. 2. According to one embodiment, one or more estrogen receptor-specific aptamers 26 and one or more cancer cell-specific binding aptamers 28 form the functional components of the conjugate 20. (In FIG. 2, two of each are shown; however, 3:1 or 1:3 variations can also be employed.) All four of these molecules are biotinylated 24, and the conjugate is formed upon incubation of the biotinylated aptamers with streptavidin 22. Biotinylation of the aptamers at their 3' ends is known not to interfere with the activity of these RNA molecules (see Chu et al., "Aptamer Mediated siRNA Delivery," *Nucl Acids Res.* 34(10):e73 (2006), which is hereby incorporated by reference in its entirety).

When the conjugate of FIG. 2 includes one or more biotinylated aptamers specific for a HER2- or HER3-breast cancer cell and one or more biotinylated estrogen receptor-specific aptamers, the conjugate will deliver the estrogen receptor-specific aptamers to breast cancer cells expressing HER2 or HER3. Upon binding of the aptamer 28 to the HER2- or HER3-expressing breast cancer cell, the cancer cell will take up the conjugate, the biotinylated aptamers 26, 28 will dissociate from streptavidin, and the estrogen receptor-specific aptamers 26 will interfere with estrogen receptor signaling. Disruption of estrogen receptor signaling will diminish both proliferation and survival of the targeted breast cancer cell.

According to another embodiment of the conjugate of FIG. 2, the conjugate includes one or more biotinylated aptamers that target ovarian clear cell carcinoma cells and one or more biotinylated estrogen receptor-specific aptamers, whereby the conjugate is targeted to ovarian clear cell carcinoma cells. Upon binding of the aptamer 28 to the ovarian clear cell carcinoma, the cancer cell will take up the conjugate, the biotinylated aptamers 26, 28 will dissociate from streptavidin, and the estrogen receptor-specific aptamers 26 will interfere with estrogen receptor signaling. Disruption of estrogen receptor signaling will diminish both proliferation and survival of the targeted ovarian clear cell carcinoma.

Figure 3:
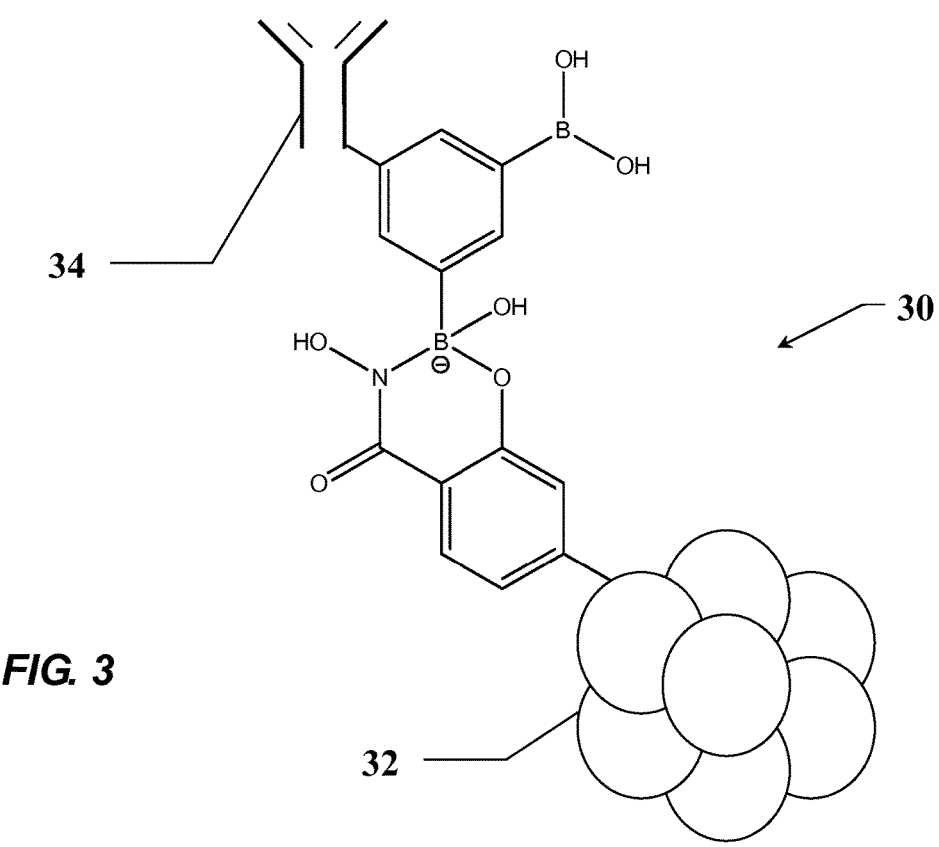
FIG. 3 is a schematic illustration of a therapeutic conjugate of the present invention, which includes a polycation-aptamer vector linked via phenyl(di)boronic acid-salicylhydroxamic acid assembly to an antibody that is specific for a cancer cell surface marker. These conjugates can be targeted to cancer cells for uptake of the construct, allowing the estrogen receptor-specific aptamer to modify estrogen receptor function in the cancer cell.

Another example of the molecular delivery agent is a conjugated aptamer molecule 30 of the type illustrated in FIG. 3. Conjugate 30 includes a polycation-aptamer vector 32 linked via phenyl(di)boronic acid-salicylhydroxamic acid assembly to an antibody 34 that is specific for a cancer cell surface marker. In this embodiment, the phenyl(di)boronic acid is first coupled to the antibody via a PEG linker using the methodology of Moffatt et al., "Successful in vivo Tumor Targeting of Prostate-specific Membrane Antigen with a Highly Efficient J591/PEI/DNA Molecular Conjugate,"*Gene Therapy* 13:761-772 (2006), which is hereby incorporated by reference in its entirety. The salicylhydroxamic acid is coupled to polyethyleneimine (PEI), a polycation, using the procedures of Moffatt et al. ("Successful in vivo Tumor Targeting of Prostate-specific Membrane Antigen with a Highly Efficient J591/PEI/DNA Molecular Conjugate," *Gene Therapy* 13:761-772 (2006), which is hereby incorporated by reference in its entirety), and thereafter the aptamer or aptamer-encoding vector (e.g., plasmid) can be introduced to the SHA-PEI solution to form the self-assembled conjugate 30.

According to one embodiment, the antibody illustrated in FIG. 3 is a HER2-specific monoclonal antibody (e.g., Trastuzumab (Herceptin®, Genentech)) and one or more estrogen receptor-specific aptamers in the PEI matrix are used to form the conjugate. This conjugate is targeted to breast cancer cells expressing HER2. Upon binding of the HER2-specific antibody to the HER2-expressing breast cancer cell, the cancer cell will take up the conjugate and the estrogen receptor-specific aptamers will interfere with estrogen receptor activity. Disruption of estrogen receptor signaling will diminish both proliferation and survival of the targeted breast cancer cell.

As an alternative to use of the aptamer construct per se, an infective transformation vector or other DNA expression system can be loaded into the PEI matrix. In this manner, the DNA expression system or transformation vector can be taken up by the targeted cancer cell, and the transformed cancer cell will express the encoded aptamer construct.

Another aspect of the invention relates to a method of treating a patient for an estrogen dependent cancer. This method includes administering to a cancer patient an agent that includes or encodes a nucleic acid aptamer molecule of the present invention, whereby the agent is taken up by an estrogen dependent-cancer cell and the nucleic acid aptamer molecule inhibits activity of the estrogen receptor in the cancer cell to inhibit cancer cell growth. The agents to be administered can be any of the agents described above. In certain embodiments, inhibition of estrogen receptor activity is lethal to the cancer cell or inhibits the rate of cancer cell growth or proliferation.

Exemplary cancers that can be treated according to this aspect of the invention are estrogen receptor-positive cancers. These include, without limitation, breast cancer, ovarian cancer, uterine cancer, and endometrial cancer.

The agents to be administered can be injected directly into a solid tumor mass. This is particularly desired where the delivery vehicle is not targeted to the cancer cells per se. Alternatively, the agents can be delivered systemically, which is suitable where the delivery vehicle is targeted to the cancer cell using a cancer cell-specific surface marker to ensure that the agent is taken up by cancer cells. Exemplary modes of administration include, without limitation, parenterally, subcutaneously, intravenously, intramuscularly, intraperitoneally, by intranasal instillation, by intracavitary or intravesical instillation, intraocularly, intraarterially, intralesionally, by application to mucous membranes, such as, that of the nose, throat, and bronchial tubes, or by transdermal delivery. For most therapeutic purposes, nucleic acids or the conjugates can be administered intravenously or parenterally.

EXAMPLES

The following examples are intended to illustrate practice of the invention, and are not intended to limit the scope of the claimed invention.

Materials and Methods for Examples 1-9

Plasmids:

Plasmids acquired are listed in Table 1. Plasmids constructed in this work are listed in Table 2. Construction of aptamer mammalian expression vectors is described below.

Human ERα coding gene was lifted from pJ3-FLAG-hERα (Walters et al., "KF-82958 is a Subtype-selective Estrogen Receptor-alpha (ERα) Agonist that Induces Functional Interactions between ERα and AP-1," *J Biol Chem* 277(3): 1669-1679 (2002), which is hereby incorporated by reference in its entirety) and cloned into pSNAP-tag®(m) vector (a gift from New England Biolabs), which contains a SNAP coding sequence immediately upstream of the insertion site. A pair of primers were designed to introduce Sbf I (5' end) and Xoh 1 (3' end) sites flanking ERα sequence for cloning. The sequences of the primers are: Forward (5'-GGC GGA CCT GCA GGA TGA CCA TGA CCC TCC ACA CCA-3', SEQ ID NO: 23); Reverse (5'-GGC GGA CTC GAG TCA GAC CGT GGC AGG GAA ACC-3', SEQ ID NO: 24). A 50 µl PCR reaction containing 5 ng of pJ3-FLAG-hERα as template, 0.2 mM dNTP, 0.8 µM primers and 5 U Phusion DNA polymerase in 1×Phusion high fidelity PCR buffer was performed according to the following PCR program: 98° C., 30 sec; (98° C., 10 sec; 72° C., 40 sec)×25 cycles; 72° C., 5 min. pSNAP-tag®(m) vector and 0.4 µg of PCR products were digested in a 50 µl reaction with 20 U Xho I and Sbf I in 1×NEBuffer 4 at 37° C. for 2 hours. Linearized vector (about 6 kb) and hERα coding sequence (about 1.8 kb) were gel-purified and extracted using QIAgen gel extraction kit. A ligation reaction was set up and a fraction was transformed into 10β competent cells (New England Biolabs). Plasmid DNA were prepared and verified by restriction digestion.

TABLE 1

Plasmids acquired

| Plasmid Name | Backbone | Gene | Sources/Ref |
|---|---|---|---|
| pET/6His- ERα-DBD (aa180-268) | pET | 6His/hERα-DBD | Kim, M/Kraus, W. L. |
| pGEX/ERα-LBD WT (aa282-595) | pGEX | GST/hERα-LBD wild type (aa282-595) | Katzenellenbogen, B. S. |
| pGEX/ERα-LBD L540Q (aa282-595) | pGEX | GST/hERα-LBD L540Q (aa282-595) | Katzenellenbogen, B. S. |
| MSCV-puro EGFP | | EGFP | Conklin, D. S. |
| 3X ERE TATA luc | pGL2-TATA-Inr | Firefly luciferase | McDonnell, D. P. |
| Renilla luc | | Renilla luciferase | Conklin, D. S. |
| pSHAG-MAGIC vector | | | Conklin, D. S. |
| pSUPER.retro.puro vector with stuffer | | | Kraus, W. L. |
| pSilencer 3.1-H1.puro | | | Applied Biosystems |

TABLE 2

Plasmids constructed in this work

| Name | Backbone | Gene |
|---|---|---|
| pSNAP-tag ®(m)/SNAP-hERα | pSNAP-tag ®(m) | SNAP-hERα |
| pSUPER-Neg Ctrl | pSUPER.retro.puro | Neg Ctrl |
| pSUPER/AptER-1 × 1 | pSUPER.retro.puro | AptER-1 × 1 |
| pSUPER/AptER-1 × 2 | pSUPER.retro.puro | AptER-1 × 2 |
| pSUPER/AptER-4 | pSUPER.retro.puro | AptER-4 |
| pSHAG-MAGIC-Neg Ctrl | pSHAG-MAGIC | Neg Ctrl |
| pSHAG-MAGIC-AptER-1 × 1 | pSHAG-MAGIC | AptER-1 × 1 |
| pSHAG-MAGIC-AptER-1 × 2 | pSHAG-MAGIC | AptER-1 × 2 |
| pSHAG-MAGIC-AptER-4 | pSHAG-MAGIC | AptER-4 |
| pSilencer-Neg Ctrl | pSilencer 3.1-H1.puro | Neg Ctrl |
| pSilencer-AptER-1 × 1 | pSilencer 3.1-H1.puro | AptER-1 × 1 |
| pSilencer-AptER-1 × 2 | pSilencer 3.1-H1.puro | AptER-1 × 2 |
| pSilencer-AptER-4 | pSilencer 3.1-H1.puro | AptER-4 |

Proteins, Protein Expression and Purification:

The recombinant hERα was purchased from Invitrogen (Cat#P2187) and EMD4 Biosciences (Cat#330655). It is 66 kDa and was isolated from recombinant baculovirus-infected insect cells. According to the specification sheet, it bound [$^3$H]-estradiol with sub-nM affinity in hydroxyapatite assays and bound specifically to estrogen response element (ERE) sequences.

The recombinant human estrogen receptor-beta (hERβ) was purchased from EMD4Biosciences (Cat#330657). It is 54 kDa and was purified from recombinant baculovirus-infected insect cells and was tested for both binding to [$^3$H]-estradiol and fluorescent estrogen (Fluormone™ ES2), according to the specification sheet.

Human ERα Ligand Binding Domain (ERα-LBD) used in the selection was purchase from Invitrogen (Cat#PV4543). It is a 62.80 kDa recombinant human protein (amino acids 282-595) expressed as a GST-tagged fusion protein in baculovirus-infected insect cells. According to the specification sheet, the concentration of functional receptor was determined by quantification of estrodial, [6, 7-$^3$H9(N)] receptor complexes using a hydroxyapatite (HAP) assay.

The His$_6$-tagged hERα DNA Binding Domain (ERα-DBD) expression construct pET/6His-ERα-DBD was made the W.L. Kraus Lab (Cornell University). It contains amino acid 180 to 268 of hERα and a hexa histidine-tag at its N-terminus. The protein was expressed in E. coli BL21 (DE3) strain. Protein expression was induced with 1 mM IPTG, and then the cell culture was incubated at 37° C. for 4-5 hours. Recombinant proteins were purified using Pro-Bond™ Resin (Invitrogen), and then dialyzed to remove imidazole, passed through Amicon Ultra 50 kD centrifugal filter devices (Millipore) to concentrate the protein and finally stored in a buffer of 50% glycerol, 500 mM NaCl, 50 mM Tris, 1 mM PMSF, 0.5 mM EDTA, 2 mM DTT. The concentration of protein was estimated by comparing with a BSA standard on a 12% protein-SDS PAGE (acrylamide:bis-acrylamide=37.5:1).

RNA Library—SELEX:

The sequences of the template-primer system have been described by Shi et al., "A Specific RNA Hairpin Loop Structure Binds the RNA Recognition Motifs of the Drosophila SR Protein B52," Mol Cell Biol 17(5):2649-2657 (1997), which is hereby incorporated by reference in its entirety. A fraction of the RNA pool of around 100 μg containing≈1.8×10$^{15}$ different sequences was used as the initial library for the first cycle of in vitro selection.

In Vitro RNA Transcription:

RNA was synthesized using the T7-MEGAshortScript™ in vitro transcription kit (Applied Biosystems) according to the manufacturer's instructions. A typical transcription reaction mixture contains 0.75 μM of DNA template, 10 mM of dNTP and 2 μl of enzyme mix in 20 μl 1×transcription buffer. The reaction was incubated at 37° C. for 4 hours to overnight. The DNA template was removed by incubation at 37° C. for 40 min with 2 μl of Turbo DNase (2 U/μl) supplemented with the kit.

To the reaction, 140 μl of DEPC-treated water was added to increase the volume to around 160 μl. RNA was extracted with equal volume of phenol, followed by an extraction using equal volume of chloroform, and then precipitated with 1/10 volume of 5M ammonium acetate, equal volume of isopropanol for at least 20 min at −70° C. RNA was spun down in a bench top Eppendof centrifuge at the maximum speed at 4° C. for 30 min. A small sampling of each RNA preparation was subjected to electrophoresis in an 8% polyacrylamide, 7M urea gel in 1×Tris-Borate-EDTA (TBE) buffer and shown to be of the expected size.

Positive Selection Using Nitrocellulose Filter:

Target proteins were prepared within 250 μl of 1×binding buffer (12 mM HEPES/pH 7.6, 150 mM NaCl, 10 mM MgCl$_2$,) containing 1 μl of SUPERase In (Applied Biosystems). Ten microgram of pool RNA (0.3 nmole) in 0.25 ml 1×binding buffer (12 mM HEPES/pH 7.6, 150 mM NaCl, 10 mM MgCl$_2$) was incubated at 65° C. for 10 minute, and then cooled at room temperature (25° C.) for 10 more minutes. Three microliters of SUPERase In was added to the RNA. RNA was mixed with the target protein, and 1×binding buffer was added to adjust the reaction to 0.5 to 1 ml. The binding reaction was kept in a water bath at 37° C. for 30 min. When a post-amplification negative selection was performed immediately before a positive selection, retrieved RNA in 1×binding buffer was directly used for binding reaction.

A piece of nitrocellulose filter was placed onto a filtration device and pre-wet with 500 μl of 1×binding buffer. Buffer was sucked out of the filter by vacuum. The binding reaction was applied onto the filter and filtered through slowly and gently. Then the filter was washed with 5 to 16 ml of 1×binding buffer. The filter paper was put into a 2 ml tube containing 0.3 ml of eluting buffer (89 mM Trisbase, 89 mM borate, 2 mM EDTA, 8 M urea), and incubated at 95° C. for 3 min, then vortexed vigorously for 1 min. 0.3 ml of acid phenol was added to the elution, which was then incubated for 2 more minutes and vortexed again. 0.1 ml chloroform was added before spinning the elution at 4° C. at maximum speed for 16 min. The aqueous phase was saved and kept on ice. 0.25 ml $H_2O$ was added to the organic phase, followed by incubation at 95° C. for 5 min. The elution was vortexed and spinned again for 12 min. The aqueous phase was pooled with the first elution and extracted with equal volume of chloroform. RNA in the elution was precipitated as described above in the Materials and Methods except the addition of 1 μg of linear acrylamide carrier.

Post-Amplification Negative Selection:

Ten micrograms of pool RNA (0.3 nmole) in 0.25 ml 1×binding buffer (12 mM HEPES/pH 7.6, 150 mM NaCl, 10 mM $MgCl_2$) was incubated at 65° C. for 10 minute, and then cooled at room temperature (25° C.) for 10 more minutes. Three microliters of SUPERase In (Applied Biosystems) was added to the RNA.

Two pieces of nitrocellulose filter (0.45 μm, Millipore) were placed in a sterile petri dish and pre-wet with 100 μl 1×binding buffer. With the aid of two flamed forceps, they were folded into a funnel-like shape, overlapped and put into a 0.6 ml tube. A hole was made at the bottom of the tube, which was then put into a 2 ml tube. Buffer was removed from the filters by spinning the tube briefly. RNA was added to the center of the filter, and the device was incubated at 37° C. for 20-30 min, followed by a spin at 4° C. for 1 min to collect RNA from the filter. This flowthrough was used in the following positive selection.

Pre-Amplification Negative Selection Against Filter:

RNA retrieved from the positive selection after Ethanol (EtOH) precipitation was reconstituted in 100 μl of 1×binding buffer, and 1 μl of SUPERase In was added to the RNA. The procedure was the same as a post-amplification negative selection described above, except that in the last step the flowthrough was extracted with phenole/chloroform and then precipitated as described above with 1 μg of linear acrylamide carrier.

Hybridase Restriction Treatment:

In a reaction of 100 μl, around 100 ng of pool RNA (150 nM) and 1.5 μM of each marking oligo, anti-FBS1 (5'-GGC CTC ACG CCT CCT AAC TC-3', SEQ ID NO: 25) and anti-FBS2 (5'-GAC CGG AGG CGC TAA GTT TC-3', SEQ ID NO: 26), were mixed in 1×Hybridase buffer (50 mM Tris-Cl/pH 7.4, 100 mM NaCl, 10 mM $MgCl_2$). The reaction mix was incubated at 95° C. for 5 min, and left at room temperature for 10 min before adding 5 units of thermostable Hybridase (Epicentre Corp.), and transferring to 53° C. for 1 hour. After the incubation, the reaction was extracted with phenol/chloroform and precipitated with 1 μg of linear acrylamide.

Gel Selection:

A selection done on a native polyacrylamide gel or an agarose gel was performed in the same way as Electrophoretic Mobility Shift Assay (EMSA), except the different composition of a binding reaction and an additional step to retrieve RNA from the shifted bands. Both radiolabeled and non-radialabeled RNAs were prepared for a pool. A radioactive reaction was set up as a binding reaction for regular EMSA with excessive protein (200 nM vs 0.1 nM RNA) for visualizing the shifted band, while the "cold" reaction included excessive RNA (1.5 μM vs. 200 nM protein) to allow competition for the target protein and selection for tight binder.

After the shifted band of the radioactive reaction was located with the aid of a storage phosphor screen and Typhoon™ phosphoimager (GE healthcare), the invisible non-radioactive shifted band was sliced out. RNA was extracted from an agarose gel using QIAgen gel extraction kit or from a polyacrylamide gel by elution. RNA was then extracted with phenol/chloroform and precipitated with 1 μg of linear acrylamide.

Positive Selection Using Profinity IMAC Resins:

Five microliters of Profinity IMAC resins (Bio-rad) in 10 μl of slurry was taken and washed 3 times with 500 μl of 1×protein binding buffer (300 mM NaCl; 30 mM HEPES/pH 7.6), and centrifuged at 1000×g at room temperature for 1 min. One microgram of $His_6$-tagged hERα DBD at 10 ng/μl was added to the resins, together with 400 μl of 1×protein binding buffer, and incubated at 4° C. for 15 min with rotational mixing. The resins were washed once with 500 μl of 1×RNA binding buffer (12 mM HEPES/pH 7.6, 150 mM NaCl, 10 mM $MgCl_2$), and then 200 μg of yeast RNA (Applied biosystems) at 5 mg/ml was added, together with 10 μl of water and 50 μl of 2×RNA binding buffer. The slurry was incubated at 4° C. for 15 min with rotational mixing.

A candidate RNA pool of 10 μg was reconstituted in 1×RNA binding buffer as previously described, and then added together with 2 μl of SUPERase into the resins above. The slurry was incubated with rotation at room temperature for 30 min, before being transferred to a Handee Centrifuge column (0.8 ml; 30 μm pore size; Pierce, Cat #89868). The resins were washed with 500 μl of 1×RNA binding buffer 5 times. RNA bound proteins were eluted with 300 μl Elution Buffer (300 mM NaCl; 30 mM HEPES/pH 7.6; 0.5 M imidazole) twice, with 2 min of incubation before centrifuging. The two fractions were pooled together and subjected to the following negative selection using "bead and filter".

Negative Selection Against Bead & Filter:

Five microliters of Profinity IMAC resins (Bio-rad) in 10 μl of slurry was taken and washed 3 times with 600 μl of 1×RNA binding buffer in a 0.6 ml tube. RNA retrieved from positive selections (600 μl), together with a piece of filter and 2 μl of SUPERase was added to the resins, followed by incubation at room temperature for 15 min with rotation. A hole was made at the bottom of the tube, which was then put into a 2 ml tube. After a spin at 1000×g for 1 min at 4° C., the passthrough was collected and transferred to a Handee Centrifuge column to filter out resins by centrifuging at 1000×g for 1 min at 4° C. Flowthrough was extracted with phenol and chloroform, and then precipitated with EtOH and 1 μg of linear acrylamide.

Reverse Transcription (RT) and Polymerase Chain Reaction (PCR)—RT:

If the amount of retrieved RNA is unknown, it would be prudent to perform a Pilot RT and PCR first with 1/10-1/5 RNA. The RT was carried out using SuperScript III reverse transcriptase kit (Invitrogen). RNA in 6.5 μl of 10 mM Tris/pH 7.5 together with 2 μl of 20 μM reverse primer was incubated at 70° C. for 10 min, and then incubated at 42° C.

for 5 min. To the mixture above, 4 μl of 5×1$^{st}$ strand synthesis buffer, 3 μl of 2.5 mM dNTP mix, 2 μl of 0.1M DTT, 1 μl of SUPERase•In and 1 μl of SuperScript III RT were added. The reaction mixture was incubated at 37° C. for 20 min, then at 48° C. for 20 min. A non-RT control contains all the components except SuperScript III RT.

When performing a pilot PCR, ¹/₄₀ of a RT reaction was taken as the template for a 100 μl PCR reaction. A typical PCR reaction contains 1.5 M betaine, 10 mM Tris pH 8.3, 50 mM KC, 1.5 mM MgCl$_2$, template, 0.5 M primers, 200 μM dNTP, and 5 U Taq polymerase. Standard PCR cycles were used: 98° C., 4 min; (98° C., 1 min; 60° C., 2 min; 72° C.; 3 min)×n cycles; 72° C., 2 min. Four such reactions covering a range of 8 cycles were set up. The primer pair used for amplification of the library is as follows. Forward primer P40 (5'-GTA ATA CGA CTC ACT ATA GGG AGA ATT CAA CTG CCA TCT A-3', SEQ ID NO: 27); Reverse primer P22 (5'-ACC GAG TCC AGA AGC TTG TAG T-3', SEQ ID NO: 28).

Product DNA was analyzed using an 8% polyacrylamide gel (acrylamide:bis-acrylamide=37.5:1). Appropriate cycle number was determined based on the band pattern and intensity. The main RT reaction used the template for a 200-400 μl PCR reaction to amplify the selected pool. The PCR products were checked on an 8% polyacrylamide gel. The DNA was extracted with phenol/chloroform and precipitated.

Cloning a Selected Library:

A selected library in the form of DNA was cloned into pSTBlue-1 blunt vector (Introductory pSTBlue-1 Perfectly Blunt® Cloning Kit, EMD4Bioscienses) following the instruction of the manufacturer. In brief, 5 ng of DNA was subjected to end-conversion in a 10 μl reaction with 5 μl of end conversion mix. After incubation at 22° C. for 15 min, the enzyme was inactivated by heating at 75° C. for 5 min. One microliter (50 ng) Blunt Vector and 1 μl (4U) T4 DNA Ligase were added directly to the end-conversion reaction. The ligation reaction was incubated at room temperature for 2 hours to overnight. For a transformation reaction, a tube of NovaBlue Singles Competent Cells was used and 5 μl of ligation reaction was added to the cells. After an incubation on ice for 5 min with the DNA, cells were heat-shocked at 42° C. for 45 sec. Appropriate amount of LB media at room temperature was added to the reaction, which was then incubated at 37° C. for 45 min with shaking. Appropriate amount of culture was plated on LB plates with 100 mg/L ampicillin as a selective agent. After an overnight incubation at 37° C., single colonies growing on the plates were picked out for analysis.

RNA-Protein Binding Assay:

Two assays were usually used to examine RNA-protein interaction, i.e., Electrophoretic Mobility Shift Assay (EMSA) and nitrocellulose filter-binding assay. In both, a binding reaction was set up with internally radiolabeled RNA and proteins, and then it was either electrophorized on a gel or filtered through a nitrocellulose membrane to separate bound RNA from free RNA. RNA was transcribed from a double-stranded DNA template. The template was usually synthesized by bidirectional primer extension if it was between 60-100 bp in length, or by typical PCR amplification from a template using a specific primer pair if it was longer than 100 bp. To investigate whether a third party (RNA, DNA or small molecule ligand) interferes with known RNA-protein interaction, competition assay were carried out by adding competitors in excess (hundreds or thousands folds) to the RNA-protein binding reaction and observe the change in RNA-protein complex formation.

Primer Extension:

A primer extension reaction was similar to a typical PCR reaction described above with some modifications. Two primers with a complimentary region of around 30nt at their 3' portion were designed so they can anneal to each other. The conventional template was omitted in the components, and two amplification cycles were run. The PCR products were checked on a 8% polyacrylamide gel (acrylamide:bis-acrylamide=29:1).

Radioactive RNA Transcription:

The [α-$^{32}$P] CTP-incorporated RNA was prepared using the MAXIscript™ in vitro transcription kit (Applied Biosystems) according to the manufacturer's instructions. Prior to their use, a small sample of each RNA preparation was subjected to electrophoresis on an 8% polyacrylamide (acrylamide:bis-acrylamide=29:1), 7M urea gel and shown to be of the expected size.

RNA Aptamer-Protein Binding Reaction:

All binding reactions were performed in 20 μl in 1×binding buffer containing 12 mM HEPES/pH 7.6, 150 mM NaCl, 10 mM MgCl$_2$, 50 mg/L BSA and 50 mg/L yeast RNA. A typical binding reaction using labeled RNA contained approximately 0.1-1 nM $^{32}$P-labeled RNA probe and 2.5-250 nM protein.

Initially, RNA was denatured in 1×binding buffer at 70° C. for 10 minutes and then incubated at room temperature (25° C.) for 10 minutes before the addition of protein and other components. The reactions were allowed to equilibrate for 45 minutes at 37° C. before being subjected to EMSA or filter-binding assays. When a ligand was added, such as 17β-estradiol (E2) or 4-hydroxytamoxifen (OHT), 40 nM-5αM of ligand was pre-incubated with the human ER protein at 37° C. for 10 minutes before adding the RNA aptamer. When non-radioactive RNA aptamer competitors or estrogen response element (ERE) were added in a competition assay, they were first reconstituted in 1×binding buffer, mixed with $^{32}$P-labeled RNA aptamer before the addition of hER protein.

Electrophoretic Mobility Shift Assay (EMSA):

RNA-protein binding reaction were separated on 4.8-7.5% polyacrylamide gel (acrylamide:bis-acrylamide=37.5-70:1) or 2% agarose gel made with ¼×TBE buffer. A polyacrylamide gel was first subjected to 300 volts for 30 minutes at 4° C. Wells were rinsed with running buffer (¼×TBE buffer) 2-3 times before loading samples. An agarose gel in running buffer (¼×TBE buffer) was chilled at 4° C. for 30 min before loading. The binding reaction was mixed gently with 4 μl of 50% glycerol, and then loaded onto the gel and electrophoresed at 300V for 3 hours in a polyacrylamide gel or at 135V for 2 h in an agarose gel at 4° C. Polyacrylamide gels were dried at 85° C. in a gel dryer (Bio-rad) for 30 min, while agarose gels were dried at 50° C. in a gel dryer for 2 hours. Gels were exposed to storage phosphor screen (GE healthcare) for appropriate time. The image was scanned using a Typhoon™ phosphoimager with ImageQuant software (GE healthcare) and data was analyzed.

Nitrocellulose Filter-Binding Assay:

The reaction mixture was immobilized on a nitrocellulose membrane (Schleicher and Schuell, pore size 0.45 μm) using Bio-Dot and Bio-Dot SF Microfiltration Apparatus (Bio-rad). The nitrocellulose membrane and two pieces of 3M Whatmann filter paper were first soaked in 1×binding buffer, and then assembled in the manifold as per company recommendations. Each well was pre-washed with 0.5 ml of binding buffer. Samples were loaded in the wells and vacuum was applied to drive filtration, and then each well was washed with 1 ml of 1×binding buffer. The nitrocellulose membrane was then air dried and exposed to a storage phosphor screen (GE Healthcare) for appropriate time. The image was scanned using a Typhoon™ imager and ImageQuant software (GE Healthcare) and the data was analyzed. An average background binding value from three independent areas was subtracted from every data point.

When making the aptamer binding curves, data were imported into Sigma Plot 9.0.1 (Systat Software Inc.) with columns of average signal intensity vs. protein concentration (nM). Binding activity (% binding) at each protein concentration was determined as the percentage of the saturated RNA-protein complex signal. % binding was plotted as a function of the protein concentration (nM). The data points were fitted using sigmoidal curves with Hill equation (y=a*x^b/(c^b+x^b), 3 parameters). In this equation, b represents Hill coefficient, and c represents dissociation constant $K_d$. Thus, $K_d$ was calculated based on the data using the software.

Electrophretic Mobility Shift Assay (EMSA) with DNA Probes:

ERE-50mer (5'-AGT CAG GTC ACA GTG ACC TGA TCG AAA GAT CAG GTC ACT GTG ACC TGA CT-3', SEQ ID NO: 29) contains 1 copy of the ERE identified in the *Xenopus laevis* vitellogenin A2 promoter (5'-GGT CAC AGT GAC C-3', SEQ ID NO: 30). A GAAA tetra loop enforces the oligo to form a hairpin, and the ERE sequence was located in the double-stranded region of the hairpin. ERE-50mer was 5'-radiolabeled by transfer of the γ-$^{32}$P from [γ-$^{32}$P]ATP in a reaction catalyzed by bacteriophage T4 polynucleotide kinase, and then incubated with hERα proteins. The binding reaction was electrophoresed for 90 min at 4° C. and visualized with the aid of a storage phosphor screen and Typhoon™ phosphoimager system.

Phosphorylating the 5' Termini of Oligonucleotides:

A 15 μl reaction mixture was set up with 20 pmole ERE, 20 pmole [γ-$^{32}$P]ATP, 10U T4 Polynucleotide Kinase in 1×Reaction Buffer A (500 mM Tris-HCl (pH 7.6 at 25° C.), 100 mM MgCl$_2$, 50 mM DTI, 1 mM spermidine), and incubated at 37° C. for 1 hour.

ERE-hER Binding Reaction:

ERE was reconstituted in DBD binding buffer (20 mM Tris/pH 7.4, 60 mM NaCl, 1 mM DTT, 50 ng/μl salmon sperm testis DNA, 250 ng/μl BSA, 10% glycerol) by a 5 min incubation at 95° C., and slow cooling down to room temperature. An ERE-hER binding reaction was set up with 5 μM ERE, 50-150 nM hER protein in DBD binding buffer, and incubated on ice for 30 min, before loading into 4.8% polyacrylamide gel (acrylamide:bis-acrylamide=27.5:1) made with ½×TGB (12.5 mM Tris base, 100 mM glycine) and 10% glycerol. The gel was run for 2½ hours at 4° C. The gel was dried at 85° C. in gel dryer for 30 min and exposed to storage phosphor screen for appropriate amount of time. The image was scanned using a Typhoon™ phosphoimager with ImageQuant software (GE healthcare) and data was analyzed. In competition assay, non-radioactive ERE or RNA aptamers were reconstituted as described before, and then mixed with radioactive ERE before adding protein.

Minimization and Augmentation of AptER-1:

A series of primers were designed for generating truncated AptER-1 double stranded DNA template and a dimeric AptER-1. All forward primers contain a T7 promoter, recognized by T7 transcriptase. The primers (forward and reverse) are list as follows. AptER-1-53nt: sB63(53nt)-f (5'-GTA ATA CGA CTC ACT ATA GGG CAC CGC GAA C-3', SEQ ID NO: 31); sB63(53nt)-r (5'-GGG CTT GTA GTG CTC TG TCG G-3', SEQ ID NO: 32). AptER-1-65nt: 6B1-B63f (5'-GTA ATA CGA CTC ACT ATA GGG CAG AGG CAC CGC GAA C-3', SEQ ID NO: 33); 6B1-B63r (5'-GGG CAG AAG CIT GTA GTG C-3', SEQ ID NO: 34). AptER-1×2(138nt): sB63×2(138nt)-F1 (5'-GTA ATA CGA CTC ACT ATA GGA TCC GTG ACG GGC ACC GCG AAC AAA ACG CAA GAC AGA GTG CCG ACA AGA GCA CTA CAA GCC CGT CCA TAC-3', SEQ ID NO: 35); sB63×2(138nt)-R1 (5'-GGA TCC GCC TCC GGC TG TAG TGC TCT TGT CGG CAC TCT GTC TTG CGT TTT GTT CGC GGT GCC GGA GTA TGG ACG GGC TTG TAG TGC TCT-3', SEQ ID NO: 36). Other primers used and mentioned in Example 5 are listed as below. ERApt-1f (5'-GTA ATA CGA CTC ACT ATA GGG CAC CGC GAA CAA AAC GC-3', SEQ ID NO: 37); ERApt-1r (5'-GGG CAC TCT GTC TTG CG-3', SEQ ID NO: 38); ERApt-1r-24nt (5'-CAA GAC AGA GTG CCG ACA AGA GCA CTA CAA GCC CGT CCA TAC-3', SEQ ID NO: 39).

Construction of Aptamer Expression Vectors for Mammalian Systems:

The pSUPER.retro.puro vector was prepared by a double digestion using two restriction enzymes, Bgl II and Hind III, followed by gel-purification of the DNA fragment of expected size using QIAgen gel extraction kit. In a 50 μl restriction reaction, 10 μg pSUPER.retro.puro (with stuffer) plasmid, 25 U Bgl II and 50 U HindIII were mixed in 1×NEBuffer 3(New England Biolabs). The reaction was incubated at 37° C. for 4 hours and then electrophorized on 1% agarose gel made with 1×TBE buffer for 1½ hours. A DNA fragment of 6-8 kDa was sliced out and extracted with QIAgen gel extraction kit to purify the DNA.

pSHAG-MAGIC vector was digested sequentially with BseRI and BamHI, followed by gel-purification of the DNA fragment of expected size using QIAgen gel purification kit. In a 40 μl restriction reaction, 4.5 μg pSHAG-MAGIC plasmid DNA and 8 U BseRI were mixed in 1×NEBuffer 4(New England Biolabs). The reaction was incubated at 37° C. for 2 hours. As a second step, 100 U Bam HI and 100 μg/ml Bovine Serum Albumin were added and the reaction was incubated 37° C. for another 2 hours. To ensure complete separation of uncut pSHAG-MAGIC plasmid and linear pSHAG-MAGIC vector, the restriction reaction was first electrophorized on 0.8% agarose gel made with 1×TBE buffer for 1½ hours at 140V, and the band of around 3 kDa was sliced out and insert into a second 0.8% agarose gel for further electrophoresis of 1.5 hours at 140V. A DNA fragment of 3 kDa was sliced out and extracted with QIAgen gel extraction kit to purify the DNA.

pSilencer 3.1-H1.puro vector was purchased from Applied Biosystems in the linear form and was ready for ligation.

Designing Aptamer Coding Genes:

Three aptamer coding genes were designed, i.e., minimized AptER-1 monomer (AptER-1×1), minimized AptER-1 dimer (AptER-1×2) and full length AptER-4 (AptER-4). The coding gene for AptER-1×1 was lifted from the full length AptER-1; for AptER-1×2, it was lifted from a dimeric AptER-1 construct, AptER-1(138nt); for AptER-4, it was lifted from the full-length AptER-4. To generate DNA templates of these constructs, sets of primers carrying the endonuclease restriction sites compatible with those on the linearized vectors are synthesized for each template. DNA products from the PCR reactions were subjected to restriction digestions. As a negative control, a short hairpin RNA coding gene (Applied Biosystems), with no known target in either human or mouse genome, was also cloned into the vectors. To generate the coding gene for the negative control, a pair of DNA oligonmers was synthesized and annealing to form dsDNA ready for vector ligation.

The two restriction sites on coding genes for pSUPER and pSilencer vectors were Bam HI (5' end) and Hind III (3' end). Thus, only one set of DNA inserts was required. The sequences of the primer pairs (forward and reverse) designed to amplify the coding genes are listed below. AptER-1×1: Forward (5'-AGA TAT CGG ATC CGA GAG GCA CCG CGA ACA AAA CG-3', SEQ ID NO: 40); Reverse (5'-AGA TAT CAA GCT TTT CCA AAA AAG AGA GGC TTG TAG TGC TC-3', SEQ ID NO: 41). AptER-1×2: Forward (5'-AGA TAT CGG ATC CGC GTG ACG GGC ACC GCG-3', SEQ ID NO: 42); Reverse (5'-AGA TAT CAA GCT TTT CCA AAA AAG CGC CTC CGG CTT GTA G-3', SEQ ID NO: 43). AptER-4: Forward (5'-AGA TAT CGG ATC CGA GAA TC AAC TGC CAT C-3', SEQ ID NO: 44); Reverse (5'-AGA TAT CAA GCT ITT CCA AAA AAG AGT CCA GAA GCT TGT AG-3', SEQ ID NO: 45). There is a Hind III restriction site within AptER-4 coding gene. A second set of oligos were annealing to form dsDNA, and included as a second insert in the vector ligation reaction without any necessity of restriction. The sequences are Forward (5'-AGC TTC TGG ACT CTT TT TGG AAA-3', SEQ ID NO: 46) and Reverse (5'-AGC TTT TCC AAA AAA GAG TCC AGA-3', SEQ ID NO: 47). Negative control: Forward (5'-GAT CCA CTA CCG TG TTA TAG GTG TTC AAG AGA CAC CTA TAA CAA CGG TAG TTT TTT GGA AA-3', SEQ ID NO: 48); Reverse (5'-CAC TAC CGT TGT TAT AGG TGT TCA AGA GAC ACC TAT AAC AAC GGT AGT TTT TTG GAA AAG CT-3', SEQ ID NO: 49).

The primer pairs for pSHAG-MAGIC carried different restriction sites, BtsCI at the 5' end to generate a compatible site with BseRI, and BamHI at the 3' end. The sequences of these primer pairs (forward and reverse) are listed below. AptER-1×1: Forward (5'-AGA TAT CGG ATG CGA GAG GCA CCG CGA ACA AAA CG-3', SEQ ID NO: 50); Reverse (5'-AGA TAT CGG ATC CAA AAA AGA GAG GCT TGT AGT GCT C-3', SEQ ID NO: 51). AptER-1×2: Forward (5'-AGA TAT CGG ATG CGC GTG ACG GGC ACC GCG-3', SEQ ID NO: 52); Reverse (5'-AGA TAT CGG ATC CAA AAA AGC GCC TCC GGC TTG TAG-3', SEQ ID NO: 53). AptER-4: Forward (5'-AGA TAT CGG ATG CGA GAA TTC AAC TGC CAT C-3', SEQ ID NO: 54); Reverse (5'-AGA TAT CGG ATC CAA AAA AGA GTC CAG AAG CTT GTA G-3', SEQ ID NO: 55). Negative control: Forward (5'-ACT ACC GT GTT ATA GGT GTT CAA GAG ACA CCT ATA ACA ACG GTA GTn TTT TG-3', SEQ ID NO: 56); Reverse (5'-CGA CTA CCG G TTA TAG GTG TTC AAG AGA CAC CTA TAA CAA CGG TAG TTT TTT GGA TC-3', SEQ ID NO: 57).

Preparation of DNA Inserts:

Two 100 μl typical PCR reactions were set up as described in the Materials and Methods except that around 3 nM DNA template was included in each reaction. The regular PCR program was used with 11 cycles of amplification. After the sizes of amplified fragments were confirmed to be correct, the PCR products were extracted using QIAgen extraction kit.

The amplified DNA inserts for pSUPER and pSilencer vectors were sequentially digested with Hind III and Bam HI. In a 50 pt restriction reaction, around 1.25 μg DNA and 100 U Hind III were mixed in 1×NEBuffer 2 and incubated for 2 hours. As a second step, 500 U Bam HI and 100 μg/ml Bovine Serum Albumin (BSA) were added and the reaction was adjusted to 100 μl in 1×NEBuffer 2 and incubated 37° C. for another 2 hours. The DNA was purified either by gel-purification [8% polyacrylamide gel (acrylamide:bis-acrylamide=27.5:1)] or using QIAgen PCR product extraction kit.

The amplified DNA inserts for pSHAG-MAGIC vectors were sequentially digested with Btsc I and Bam HI. In a 40 μl restriction reaction, around 1 μg DNA and 20 U Btsc I were mixed in 1×NEBuffer 4 and incubated 50° C. for 2 hours, followed by further incubation at 4° C. overnight. As a second step, 100 U Bam HI and 100 μg/ml BSA were added and the reaction was adjusted to 50 μl and incubated 37° C. for 2 hours. The DNA was purified using QIAgen gel extraction kit.

Ligation, Transformation and Sequence Verification:

The digested DNA insert and vector were ligated and transformed into MM294 competent cells. Plasmid DNAs from single colonies were purified and sequenced to confirm the sequence fidelity.

A ligation reaction usually contained 100-200 ng of linear vector, 5 ng of digested DNA insert and 10 U of T4 DNA ligase (Novagen) in 1×T4 DNA ligase buffer. The reaction was incubated at room temperature for 2 h to overnight.

A fraction of a ligation reaction (usually 1/10 volume of competent cells used) was added to MM294 competent cells and the transformation reaction was incubated on ice for 5 min before a heat-shock at 42° C. for 45 sec. LB media was added to the transformation reaction, and cells were incubated at 37° C. for 30 min before being plated on LB plates containing antibiotics.

Single colonies were randomly picked out and plasmids were prepared using QIAgen plasmid DNA miniprep kit. The inserts were sequenced to confirm fidelity using a vector primer. The vector primers used are listed below. pSilencer: M13F(-40) (5'-GTT TTC CCA GTC ACG AC-3', SEQ ID NO: 58); 3.0rev (5'-GAG TTA GCT CAC TCA TTA GGC-3', SEQ ID NO: 59). pSUPER: Sequencing primer 1(5'-GGA AGC CIT GGC TTT TG-3', SEQ ID NO: 60); Sequencing primer 2 (5'-GAT GAC GTC AGC GT CG-3', SEQ ID NO: 61). pSHAG-MAGIC: M13F(-40) (5'-GTT TTC CCA GTC ACG AC-3', SEQ ID NO: 62); M13 reverse (5'-CAG GAAACA GCT ATG AC-3', SEQ ID NO: 63).

Cell Culture and Transfections:

All cell culture reagents were purchased from Fisher scientific unless stated otherwise. MCF7, HeLa and HEK293FT cells were generous gifts from Dr. Douglas Conklin. They were maintained in DMEM High (Hyclone), supplemented with 10% fetal bovine serum (FBS) (Hyclone), 100 U/ml penicillin, 100 mg/ml streptomycin (Cellgro). MCF7 was also cultured in estrogen-free media, which contained DMEM high/phenol red free media (Hyclone), supplemented with 10% dextran-coated charcoal-treated FBS (Hyclone), 1 mM sodium pyruvate (Sigma) and 100 U/ml penicillin, 100 mg/ml streptomycin.

HeLa cells were transfected using FuGENE 6, while all other cell lines were transfected using FuGENE HD. Cells were split and seeded on a plate one day before transfection. The condition of a transfection reaction were suggested by the manufacturer, according to the surface area of a plate. The ratio of FuGENE reagents (volume, μl) to DNA (mass, μg) was always 3:1. Transfection reagents were vortexed for 2 seconds and warmed up to room temperature, before being added to serum-free media and incubated at room temperature for 5 min. DNA was added to the reagent mixture, and the mixture was incubated at room temperature for 40 min before being dispended evenly into cell culture. Transfection efficiency was monitored by co-transfecting MSCV-Puro/EGFP vector expressing green fluorescent protein (EGFP) equal to 20% of total DNA.

Total RNA Extraction:

Total RNA was prepared using TRIzol reagent (Invitrogen) according to the manufacturer's instructions. One well of cells in a 6-well plate was washed once with 2 ml of 1×PBS (room temperature) after the removal of growth media. To each well, 0.5 ml of TRIzol was added to the cells and used to rinse off all cells. After incubating for 5 min, cell lysate was transferred to an eppendorf tube. RNA was extracted and further purified using RNeasy Plus Mini Kit (Qiagen), following the manufacturer's instructions.

Real Time RT-PCR:

Real time RT-PCR is carried out in two successive steps: RT and qPCR. One microgram of total RNA was reverse transcribed in a total volume of 20 µl. A 9 µl mixture of RNA, 0.5 µg oligo dT (18 or 20mer, Promega) and 1 µM aptamer specific reverse primers was incubated at 65° C. for 5 minutes, followed by an incubation at 4° C. for 1 minutes. Then, 4 µl of 5×1$^{st}$ strand synthesis buffer, 2 µl 0.1 M DTT, 3 µl 2.5 mM dNTP mix, 1 µl RNase inhibitor, and 200 U Reverse transcriptase (Invitrogen) was added and incubated at 53° C. for 1 hour, followed by an incubation at 75° C. for 5 minutes. RNA was omitted in a non-template control to detect any primer dimer product, and the reverse transcriptase was omitted in a non-RT control to detect any DNA contamination.

The resulting cDNA was then diluted to a total volume of 40 µl with sterile $H_2O$. Each real-time PCR reaction consisted of 2 µl diluted RT product, 1×SYBR Green PCR Master Mix (New England Biolabs), and 500 nm forward and reverse primers. Triplicates were always included for each sample. Reactions were carried out on an ABI PRISM 7900HT Sequence Detection System (Applied Biosystems) for 40 cycles (95 C for 15 sec, 60 C for 1 min) after initial 10-min incubation at 95° C. Aptamer levels were normalized against beta-actin mRNA control and expressed as folds of beta-actin mRNA levels. The fold change in expression of each gene was calculated using the ΔΔCt method, with beta-actin mRNA as an internal control.

The aptamer specific primers used were listed below. AptER-1×1: sB63×1 qPCR F (5'-GAG AGG CAC CGC GAA CAA AAC-3', SEQ ID NO: 64); sB63×1 qPCR R (5'-AAG AGA GGC TTG TAG TGC TCT TGT CG-3', SEQ ID NO: 65). AptER-1×2: sB63×2 qPCR F1 (5'-GCG TGA CGG GCA CCG C-3', SEQ ID NO: 66); sB63×2 qPCR R1 (5'-AAG CGC CTC CGG CTT GTA GTG-3', SEQ ID NO: 67). AptER-4: #17×1 qPCR F (5'-GAG AAT TCA ACT GCC ATC TAG GCC AC-3', SEQ ID NO: 68); #17×1 qPCR R (5'-AAG AGT CCA GAA GCT TGT AGT ACT TAA TAC TC-3', SEQ ID NO: 69); beta actin qPCR F (5'-CTG TCC ACC TTC CAG CAG ATG T-3', SEQ ID NO: 70); beta actin qPCR R (5'-CGC AAC TAA GTC ATA GTC GCC C-3', SEQ ID NO: 71).

Dual Luciferase Assay:

An ER cis-reporting plasmid 3×ERE TATA luc contains a firefly (*Photinus pyralis*) luciferase gene driven by a promoter with three copies of *Xenopus vitellogenin* A2 estrogen response element (ERE). MCF7 cells in one well of 96-well plate were co-transfected with a total of 150 ng DNA, consisting of 75 ng of aptamer expression construct, 60 ng of 3×ERE TATA luc and 15 ng of *Renilla* luciferase expression plasmid (pRL). As a negtive control, a short hairpin RNA expression plasmid (Neg) was used to replace the aptamer expression plasmid. The transfection reactions were carried out in triplicates, and each individual reaction was subsequently subjected to a luciferase activity analysis.

Seventy-two hours after transfection, the firefly and *renilla* luciferase activities were measured using the Dual-Luciferase Reporter Assay kit (Promega), with minor adjustment to the manufacturer's protocol. Growth media containing transfection mixture were removed, and cells were washed gently three times in the well using 1×PBS (room temperature). Cells were lysed by adding 30 µl 1×Passive Lysis Buffer (PLB) (room temperature), followed by incubation at room temperature for 30 min with rocking. The PLB lysate was transferred to an opaque, round bottom 96-well plate (Costar), and then the firefly and *renilla* luciferase activities were measured on BioTek HT Synergy plate reader (BioTek). With automated dispensers, 30 µl Luciferase Assay Reagent II (LAR II) was added to the PLB lysate at 225 µl/sec, and after an incubation of 2 seconds, the firefly luciferase was measured in a kinetic reading type (500 readings in 10 seconds); and then, 30 µl 1×Stop&Glo reagent was added to the same well at 225 µl/sec, and after an incubation of 2 seconds, the *Renilla* luciferase was measured in a kinetic reading type (500 readings in 10 seconds). Firefly luciferase activity was normalized against *Renilla* luciferase activity, and the resulting value was compared with the control to determine the percentage of normalized luciferase activity of the control. Data are presented as mean±SD calculated from triplicate wells.

Western Blotting:

HeLa cells were transfected with SNAP-hERα expression vector at 0.5-3 µg/well in 6-well plates and harvested 24 h post-transfection in 60 µl 1×SDS loading buffer (New England Biolabs)/well. The samples were boiled for 5 min and then 18 µl of sample was analyzed on a precast 12% Tris-Glycine gel (Invitrogen). Proteins were transferred to a 0.45 µM nitrocellulose membrane (Millipore) and probed with rabbit anti-SNAP polyclonal antibody according to a standard protocol (Harlow, *Using Antibodies: A Laboratory Manual*, Cold Spring Harbor Laboratory Press, Cold Spring Harbor, N.Y. (1999), which is hereby incorporated by reference in its entirety). In brief, transfers were performed at 75 volts for 50 minutes in 1×transfer buffer (0.192 M glycine, 0.025 M Tris base, 20% methanol) onto an Immobilon-P membrane (Millipore). Blots were blocked in 1×TBST (150 mM NaCl, 20 mM Tris pH 8, 0.05% Tween 20) with 5% W/V dry milk for 1 hour on a shaker at room temperature. The primary antibody, polyclonal anti-SNAP antibody produced in rabbit (New England Biolabs) was added to the blocking solution and incubated on a shaker overnight at 4° C. Blots washed three times for 10 minutes with 1×TBST. The membrane was then immersed in 1×TBST with 2.5% W/V dry milk. The secondary antibody, anti-rabbit IgG from mouse conjugated to alkaline phosphatase (Cell signaling Technology) was added to this solution and incubated on a shaker for one hour at 4° C. Blots were washed three times for 10 minutes with 1×TBST. Blots were removed from the wash and developed with 10 ml LumiGLO containing 0.5 ml of 20×LumiGLO and 0.5 ml of 20×Peroxide (Cell Signaling Technology). The light emitted by destabilized LumiGLO® reagent is subsequently captured on X-ray film.

Fluorescent Microscopy:

HeLa cells were seeded in an 8-well chamber slide (Lab-Tek™) the day before transfection. Cells were transciently transfected with SNAP-hERα expression vector at 150 or 300 ng/well using FuGENE 6 as described above. Around 16 h post-transfection, the transfection complex media were removed and cells in each well were washed three times with 600 µl of complete DMEM media without disrupting the attachment of the cells. TMR-Star substrate at 5 µM in 200 µl of DMEM media was added to each well, followed by incubation at 37° C., 5% $CO_2$ for 1 hour.

Hoechst 33342 at 16.2 μM in 600 μl of complete DMEM was used to substituted for the dye above and incubated with cell at 37° C., 5% $CO_2$ for 5 min. Cells were washed in situ gently three times with 600 μl of complete DMEM media, followed by another incubation for 30 min to allow unincorporated substrate to diffuse out of cells. Media was changed once more and cells were imaged under an inverted fluorescent microscope under 63×oil lense (Zeiss).

RNA-Coimmunoprecipitation:

One 150 mm dish of HeLa cells at about 30-50% confluency were co-transfected with 7 μg of SNAP/hERα expression plasmids, 7 μg of pSUPER/AptER-1×2 vector and 1 μg of EGFP expression vector using 54 μl of FuGENE 6 as described above. In the control, the protein expression vector was substituted with a SNAP protein expression vector. Two days after transfection, cells were trypsinized and washed with 10 ml of complete DMEM media, followed by another two washing using 10 ml of ice cold 1×PBS buffer each time. Cells were fixed in 10 ml of 1% formaldehyde prepared in 1×PBS buffer with an incubation at room temperature for 10 min. Cells were washed twice using 10 ml of 1×PBS buffer each time.

Cell pellet was resuspended in 750 μl of lysis buffer, which is the immobilization buffer (50 mM Tris, 100 mM NaCl, 1 mM DTT, 0.1% NP-40) supplemented with 1×Protease inhibitor (Roche) and 100 U/ml of SUPERase In (Applied Biosystems). Cells were incubated on ice for 30 min, before being subjected to sonication. Cells samples were kept on ice throughout the sonication and 10 μl of cells were examined under microscope to ensure that the sonicate was devoid of any intact cells. Insoluble material is removed by microcentrifugation at 14,000 rpm (16,000 g) for 10 min at 4° C. For quantification of expressed aptamer, 20 μl of the supernatant was saved for total RNA extraction as described before, without the RNeasy cleanup step.

For two pull-down reactions (control+experiment), 160 μl of SNAP-Capture Pull Down Resin (New England Biolabs) was taken. Beads were washed three times with 1 ml of immobilization buffer each time, and then pre-incubated with 400 μl of lysis buffer containing 100 μg/ml yeast RNA for 2 hours at 4° C. Slurry was divided into two. Three hundred microliter of cell lysate, either the SNAP sample or the SNAP-hERα sample, was added to the beads, followed by incubation at room temperature for 2 hours. Beads were washed five times with 1 ml of high-stringency washing buffer containing 1×RIPA (Cell signaling technology), 1 M NaCl, 1M urea and 0.1% SDS.

For each RNA co-immunoprecipitation assay including a control and an experiment, 100 μl of protein G beads slurry (Cell signaling technology) was taken and mixed with 100 μl of 100 ng/μl rabbit anti-SNAP antibody. NT-2 buffer (20 mM EDTA, 50 mM NaCl, 1 mM DTT, 100 U/ml of SUPERase) was added to obtain 1 ml of binding reaction, which was incubated with gentle rotation at 4° C. overnight. Beads were washed with NT-2 buffer three times with 1 ml each time to remove unbound antibody. Beads were resuspended in 400 μl of NT-2 buffer and the slurry was divided into two equivalent portions, one for control (SNAP) and the other for experiment (SNAP-hERα). Three hundred microliter of cell lysate (same batch as described above), either the SNAP sample or the SNAP-hERα sample, was added to the beads. Appropriate amount of buffer was adjusted to become 20 mM EDTA (pH 8.0), 1 mM DTT, 100 U/ml SUPERase In. The binding reaction was incubated for 3 hours at 4° C. Beads were washed with NT-2 buffer 1 ml each time for 4 times.

Beads from both assays were resuspended in 500 μl of proteinase K buffer (20% glycerol, 100 mM KC, 0.2 mM EDTA, 0.5 mM DTT) containing 200 μg/ml of proteinase K, and incubated at 42° C. for 1 hour. The supernatant was extracted with phenol and chloroform and RNA was precipitated with linear acrylamide as described before.

RNA pulled down or immunoprecipitated and the total RNA extracted from cell lysate were aliquoted. Half was used to set up a 20 μl RT reaction, and the other half was used to set up a 20 μl Non-RT reaction. AptER-1×2 RNA was reverse transcribed using specific AptER-1×2 reverse primer described before, and then quantified using real time qPCR. The RNA pulled down or immunoprecipitated from the control (SNAP cell sample) or experiment (SNAP-hERα cell sample) was normalized against its expression level detected in the total RNA. The level of RNA pulled down in the experiment was expressed as "folds of enrichment" of the RNA level in the control.

AlamarBlue Assay:

The alamarBlue (Biosource) assay was performed 24 to 96 hours post-transfection. MCF7 cells were plated in four 96-well plates one day before transfection using an automated liquid-handling robot (Eppendof), and cell seeded in the wells were considered to be uniform. Cells in each well were co-transfected with 75 ng of the aptamer expression plasmids or control RNA expression plasmids, and 75 ng of the MSCV-puro EGFP expression vector (Clontech). Cell growth studies were performed in triplicate and relative cell viability (% of control) was expressed as the mean+/− standard deviation of the three experiments. One plate was taken for assays on each day from 24 h to 96 h post-transfection. To each well in a 96-well plate, 15 μl of alamarBlue (warmed to room temperature) was added aseptically to the cells. Cells were incubated at 37° C., 5% $CO_2$ for 4 hours. Quantification of alamarBlue was done in BioTek HT Synergy plate reader (BioTek). Fluorescence was measured every hour for four hours and the highest reading within a linear range was chosen to represent a time point (day) in the assay. The difference in alamarBlue readout between aptamer-expressing cells and the control cells were normalized against the percentage of the GFP-expressing cell (transfected cells) in each cell population, to estimate the change upon 100% transfection efficiency.

Cell Viability Assay:

After an alamarBlue reading was done for a time point (day), cells grown on a 96-well plate were fixed using 2.5% formaldehyde with incubation at room temperature for 30 min. After three washes using 200 μl of 1×PBS buffer each time, cells were stained with 5 μg/ml Hoechst 33342 (Invitrogen) for 30 min at room temperature in dark. For statistical analysis of cells, in a well of 96-well plate, 25 fields were photographed in a GE Healthcare IN Cell Analyzer 1000 with a 20×objective at 2 different wavelengths, one for detecting stained cell nuclei, and the other for GFP. Cell counts and statistics (numbers of nuclei and GFP-expressing cells) were then performed using the In Cell Investigator 3.4 high-content image analysis software (GE Healthcare). The percentage of the GFP-expressing cell in the total cells was used to normalize the cell viability data from the alamarBlue assay. Meanwhile, the data spanning a time course was used to monitor whether the aptamer-expressing cells die from the inhibiting effects of aptamers on ERα functions.

DNA Content Measurement:

About 1 million cells ($10^6$) growing on a 10 cm dish was detached using 2 ml of 0.05% trypsin, and 10 ml of DMEM High media was added to inactivate trypsin. Cells were spun down at 200×g at room temperature for 5 min, and then washed with 1% BSA/1×PBS. Cells were then resuspended in 400 µl of DAPI solution. DNA contents measurement in a BD LSR II flow cytometer and data analysis were operated by Dr. Chang-Uk Lim in the Flow Cytometry Core at Ordway Research Institute.

Example 1—In Vitro Selection for Aptamers Targeting Human Estrogen Receptor Alpha (ER-α)

It was expected that multiple target sites for RNA aptamers exist on the molecular surface of hERα, including the A/B domain, the DNA-binding domain (DBD), and the ligand-binding domain (LBD). Aptamers targeting these disparate sites would enable sub-molecular modulation of the ER function. Aptamers discriminating among different ligand-binding states (e.g., apo-, E2-, TAM-liganded) of hERα are of particular interest, as ER-cofactor interactions dependent on ligand-binding are potential points of intervention in mechanistic studies of hERα. Some critical differences between ERα and ERβ can be attributed to the A/B domain where the AF-1 resides. An aptamer against the A/B domain in hERα will help elucidate A/B domain activities either on its own or through synergistic interaction with AF-2. Apo-hERα was chosen to be the first target for two reasons: first, it ensured that all epitopes on the protein surface were available for interaction with the RNA pool; second, a uniform state of the ligand binding domain would be presented. Antagonists of apo-hERα will be valuable therapeutic leads. Selections were also carried out using single structural domains of hERα, such as DBD and E2-liganded LBD.

Initial in vitro selection was started with an RNA pool estimated to contain $1.8 \times 10^{15}$ individuals. All RNA sequences in the library share two constant regions at the 5' and 3' ends, and have a 50 nucleotide randomized region in the center. A pair of primers complementary to the constant regions, P40 (forward primer) and P22 (reverse primer), were used to amplify the RNA sequences as described in the Materials and Methods. This pool was carried through 7 cycles of selection and amplification with unliganded recombinant human ERα (Invitrogen) (FIG. 4B) as the protein target. Several parameters were changed in the seven rounds of selection, as described in Table 3. In general, as the selection proceeded, the RNA to target protein ratio and the washing stringency in the positive selection were increased to exert increasing selection pressure. The input of RNA and the amplification scale of selected pools were lowered, as the diversity of RNA species decreased. One or two negative selection steps against the nitrocellulose filter (i.e., collecting candidates unbound to the filter) were included in every cycle since the second, because the filter was used to immobilize the target protein and appeared as a potential target. To monitor the convergence of the selection process, semi-quantitative RT-PCR was used to estimate the amount of RNA molecules retrieved after each round, and these were visualized by gel electrophoresis and the recovery ratio (retrieved RNA over protein input) calculated from the intensity of bands. Afterwards, the major fractions of these RNA samples were amplified through an optimized RT-PCR.

After 7 cycles of selection and amplification (FIG. 4B), EMSA was carried out for three pools, Generations 5 to 7, to monitor the progress of selection. The binding reactions were set up with 260 nM full-length hERα, and electrophoresed in a 2% agarose gel in ¼×TBE buffer (22.25 mM Tris base, 22.25 mM borate, 0.5 mM EDTA) at 135V for 2.5 hours at 4° C. As shown in FIG. 4C, all three pools exhibited target protein-dependent shifted bands, which confirmed that some aptamers had been selected and enriched. The signal of shifted bands peaked at Generation 6 (G6, FIG. 4C). Thus, G6 was selected for gel selection to enrich the shifted RNA species, carried out as described in the Materials and Methods, and a fraction of the selected pool (G6-A) was cloned into pSTBlue-1 blunt vector and sequenced. A filter-binding sequence, named FBS (5'-GGG AGA AUU CAA CUG CCA UCU AGG CUU GAA ACU UAG CGC CUC CGG UCA CGU GGA GUU AGG AGG CGU GAG GCC AAG UAC UAC AAG CUU CUG GAC UCG GU-3', SEQ ID NO: 72), dominated the pool with a percentage of around 67%. To remove the filter binding sequence, G6 pool was subjected to a hybridase restriction treatment as described in the Materials and Methods, using antiFBS1 and antiFBS2 as guiding oligos. Quantification of residue RNA using semi-quantitative RT-PCR showed that around 60-70% of RNA was removed. Remaining RNAs in the pool (G6-B) was subjected to another round of selection ($7^{th}$ cycle in Table 3) to generate G7 pool.

To screen the last selected RNA pool for target-binding sequences, a fraction of Generation 7 was cloned. Fifty-four individuals from this library were screened for binding activity to the target protein, using either a filter-binding assay or EMSA. In general, three to five individuals were grouped and their RNA coding sequences were used as a template mixture in a 10 µl radioactive RNA transcription reaction, as described in the Materials and Methods. In a typical binding reaction, the target protein concentration was 100-200 nM. Individuals in groups showing binding capability were sequenced. There were three sequences showing specific binding to the target. The most abundant sequence, named AptER-1 (SEQ ID NO: 1), occurred 9 times within the 54 individuals examined, and two sequences occurred just once, named AptER-2 (SEQ ID NO: 2) and AptER-3 (SEQ ID NO: 3). These aptamers have the nucleotide sequences shown above. Predicted secondary structures using mFold (Zuker, "On Finding All Suboptimal Foldings of an RNA Molecule," *Science* 244(4900):48-52 (1989), which is hereby incorporated by reference in its entirety) based on energy minimization algorithms are shown in FIGS. 5A-C, respectively.

To divert aptamers to other surfaces on apo-hERα, a second in vitro selection against apo-hERα was performed beginning with Generation 3 of selection I as the starting point (FIG. 4B). Three typical cycles of selection were performed as described in the Materials and Methods, except that 300 pmole of a truncated version of AptER-1(65nt) (SEQ ID NO: 5), the same amount as a candidate RNA pool, was pre-incubated with hERα at 37° C. for 10 min to block its binding site before the addition of the candidate RNA library. AptER-1(65nt) does not contain the constant regions required for primer annealing in reverse transcription and PCR, thus although it would be selected and retrieved, it was not amplified as the full length RNA sequences were. After these three cycles using nitrocellulose filters as the partitioning matrix, another two rounds of selection were done in 4.8% polyacrylamide gel (acrylamide: bis-acrylamide=50:1) in ¼×TBE buffer, using the method described above. Several parameters were changed in the selection process, as described in Table 4.

The final selected pool (G8', FIG. 4B) in the form of DNA was cloned, as described previously. Twenty-four individuals in the library were examined for binding activity to the target protein, using either filter-binding assay or EMSA. Individuals showing binding capability were sequenced. Only one sequence occurred more than once (2 out of 24).

It was also the only sequence showing binding capability to the target protein, and it was named AptER-4 (SEQ ID NO: 4). The secondary structure of AptER-4 was predicted by mFold and is shown in FIG. 5D.

The LBD of hERα functions as a protein hub by interacting with ligands and diverse coregulators. The selectivity of cofactor recruitment is partially determined by the receptor-coregulator interface on LBD. Crystal structures of unli-

TABLE 3

In vitro selection I against unliganded hERα

| Cycle | RNA | Pre-neg selection | Positive selection hERα | R:P | RNaseIn | Vol. | Time | Washing | Post-neg selection | RT-PCR | Rec. ratio | Trscpt |
|---|---|---|---|---|---|---|---|---|---|---|---|---|
| 1 | 3 nmole 100 μg | — | 150 pmol | 20:1 | Y | 1 ml | 1 hr | 5 ml | — | 2*20 μl RT 400 μl PCR | 200 ng 4% | 40 μl 160 μg |
| 2 | 1.5 nmole 50 μg | — | 75 pmole | 20:1 | Y | 0.5 ml | 0.5 hr | 8 ml | NaCl/MgCl$_2$ | 20 μl RT 200 μl PCR | 50 ng 2% | 20 μl 40 μg |
| 3 | 0.6 nmole 20 μg | NaCl/MgCl$_2$ | 30 pmole | 20:1 | Y | 0.5 ml | 1 hr | 13 ml | NaCl/MgCl$_2$ | 20 μl RT 200 μl PCR | 20 ng 2% | 20 μl 80 μg |
| 4 | 0.3 nmole 10 μg | NaCl/MgCl$_2$ | 15 pmole | 20:1 | N | 0.5 ml | 0.5 hr | 13 ml | NaCl/MgCl$_2$ | 20 μl RT 200 μl PCR | 8 ng 1.6% | 20 μl 40 μg |
| 5 | 0.3 nmole 10 μg | — | 6 pmole | 50:1 | N | 0.5 ml | 0.5 hr | 16 ml | NaCl/MgCl$_2$; KCl/MgCl$_2$ | 20 μl RT 200 μl PCR | 80 ng 40% | 20 μl 80 μg |
| 6 | 0.3 nmole 10 μg | — | 6 pmole | 50:1 | N | 0.5 ml | 0.5 hr | 16 ml | NaCl/MgCl$_2$; KCl/MgCl$_2$ | 20 μl RT 200 μl PCR | 88 ng 44% | 20 μl 80 μg |
| 7 | 0.3 nmole 10 μg | — | 6 pmole | 50:1 | N | 0.5 ml | 0.5 hr | 16 ml | NaCl/MgCl$_2$; KCl/MgCl$_2$ | 40 μl RT 400 μl PCR | 176 ng 80% | |

Cycle = cycle number; RNA = amount of pool RNA; hERα = protein target used, purchased from Invitrogen, 2.6 μM; R:P = pool RNA to target protein ratio; RNaseIn = whether RNase inhibitor was added in the binding reaction, Y = yes, N = no; Vol. = volume of the binding reaction; Time = incubation time for the binding reaction; Washing = volume of the washing buffer used; RT-PCR = volume of RT-PCR; Rec. ratio = amount of RNA retrieved at the end of each cycle and the fraction of bound protein; Trscpt = volume of RNA transcription reaction and estimated yield. Pre-neg selection and Post-neg selection = if a negative selection was carried out before or after the positive selection, the ions in binding buffer used were indicated. NaCl/MgCl$_2$ represent 1xbuffer containing 150 mM NaCl, 10 mM MgCl$_2$ and 12 mM HEPES/pH 7.6; KCl/MgCl$_2$ represent 1x buffer containing 150 mM KCl, 10 mM MgCl$_2$ and 12 mM HEPES/pH 7.6. The method was the typical negative selection using filter papers to attract filter-binding RNAs, as described in the Materials and Methods.

TABLE 4

In vitro selection II against unliganded hERα*

| Cycle | RNA | Positive selection hERα | R:P | Vol. | Time | Washing | Post-neg selection | RT-PCR | Rec. ratio | Trscpt |
|---|---|---|---|---|---|---|---|---|---|---|
| 4' | 0.3 nmole 10 μg | 15 pmole | 20:1 | 0.5 ml | 0.5 hr | 15 ml | Filter | 20 μl RT 200 μl PCR | 16 ng 3.2% | 20 μl 80 μg |
| 5' | 0.3 nmole 10 μg | 10 pmole | 30:1 | 0.5 ml | 0.5 hr | 15 ml | Filter; Hybridase treatment** | 20 μl RT 200 μl PCR gel-purified | 64 ng 20% | 20 μl 80 μg |
| 6' | 0.3 nmole 10 μg | 6 pmole | 50:1 | 0.5 ml | 0.5 hr | 15 ml | Filter | 20 μl RT 200 μl PCR | 80 ng 40% | 20 μl 40 μg |
| 7'*** | 30 pmole 1 μg | 4 pmole | 15:2 | 0.02 ml | 0.75 hr | — | — | 20 μl RT 100 μl PCR | 100 ng 75% | 20 μl 80 μg |
| 8'*** | 30 pmole 1 μg | 4 pmole | 15:2 | 0.02 ml | 0.75 hr | — | — | 20 μl RT 200 μl PCR | 16 12% | |

*There was no pre-neg selection, and no RNase In was used in the positive selections.
**A negative selection was followed by an RNase H treatment using antiFBS1 and antiFBS2 as marking oligos, as in Example 1.
***Both cycle 7 and 8 were gel selections.

Cycle = cycle number; RNA = amount of pool RNA; hERα = protein target used, purchased from Invitrogen, 2.6 μM; R:P = pool RNA to target protein ratio; Vol. = volume of the binding reaction in ml; Time = incubation time for the binding reaction in hour (hr); Washing = volume of the washing buffer used; RT-PCR = volume of RT-PCR; Rec. ratio = amount of RNA retrieved at the end of each cycle and the fraction of bound protein; Trscpt = volume of RNA transcription reaction and estimated yield. Post-neg selection = methods of a negative selection after a positive selection was indicated, either "Filter" or "Hybridase treatment". The method of "Filter" was the typical negative selection using filter papers to attract filter-binding RNAs, as described in the Materials and Methods. The 1x binding buffer used contains 150 mM NaCl, 10 mM MgCl$_2$ and 12 mM HEPES/pH 7.6. The method of "Hybridase treatment" was described in the Materials and Methods.

Example 2—In Vitro Selection for Aptamers Targeting Human Estrogen Receptor Alpha (ER-α) Structural Domains When a small organic molecule, or an aptamer, or an antibody acts as a binding partner or ligand to a protein, the entire target molecule is often referred to as a target or a receptor of the ligand. However, to efficienctly direct aptamers against a particular structure domain, that structural domain, instead of the whole protein, can be used as the protein target. Therefore, selections were also performed using the DNA binding domain (DBD) and ligand binding domain (LBD) of hERα as targets.

ganded, agonist-liganded and SERM-liganded LBD have shown that the conformation of LBD, especially the helix 12, is rearranged dramatically upon ligand-binding. Thus, LBD is potentially a point of intervention to study the mechanisms of hERα signaling pathways. It was believed that there existed at least one target site or a set of overlapping target sites on the surface of hERα-LBD around helix 12 in a particular functional state, in which case each state is considered as a target for in vitro selection.

An in vitro selection was started with an RNA pool that was estimated to contain $1.8 \times 10^{15}$ individuals, which was the same as the RNA library used in Example 1. This process was carried through 7 cycles of selection and amplification with the E2-liganded human ERα-LBD (Invitrogen) (FIGS. 4A, 6B). A typical cycle was described in the Materials and Methods. Several parameters were changed in the seven rounds of selection, as described in Table 5. E2-liganded human ERα-LBD was prepared by incubating GST/hERα-LBD with 2 µM E2 in 500 µl (cycle #1) or 250 µl (other cycles) binding buffer for 10 min at 37° C. before the addition of the candidate RNA pool. One or two negative selection steps against the filter (i.e., collecting candidates unbound to the filter) was included in every cycle since the third cycle. To remove filter-binding species, the fourth cycle involved two negative selection steps using two different binding buffers (12 mM HEPES/pH 7.6, 150 mM NaCl, 10 mM $MgCl_2$ and 12 mM HEPES/pH 7.6, 150 mM KC, 10 mM $MgCl_2$) and no positive selection.

After 9 cycles of selection and amplification, EMSA of four pools, Generation 3, 5, 7 and 9, was carried out to monitor the progress of selection. The binding reactions were set up with 260 nM E2-liganded full-length hERα in the presence of 1 µM E2, and electrophoresed in 2% agarose gel in ¼×TBE buffer at 135V for 2.5 hours at 4° C. As shown in FIG. 6A, all four pools exhibited shifted bands, which suggested that some aptamers had been selected and enriched. The signal of shifted bands gradually intensified and peaked at Generation 7 (G7) pool, and became weaker at G9, suggesting that after cycle 7, filter-binding sequence might have competed out aptamers. Thus, G7 pool was the best point to switch to a second selection method with a different partitioning matrix, such as a gel selection. A gel selection was carried out as described in the Materials and Methods, using E2-liganded full-length hERα as the protein target, and a small sampling of the selected pool G7A was cloned and sequenced. The filter-binding sequence FBS accounted for 50% of the pool, while none of other 9 sequences had multiple copy or binding affinity to E2-liganded full-length hERα.

As E2-liganded full-length hERα, instead of LBD, was the protein target in the gel-selection mentioned above, selection might be diverted against domains other than LBD. Thus, G7, instead of the RNA pool generated after the gel selection, was chosen for an RNase restriction treatment to remove the filter binding sequence. A hybridase restriction treatment using antiFBS1 and antiFBS2 as the guiding oligos was performed. Semi-quantification using RT-PCR showed that 60-70% of RNAs in G7 pool was digested in the hybridase treatment. The resulting pool, G7B, will be used for in vitro selection for aptamers against E2-LBD.

In the classic genomic signaling pathways of hERα, upon activation of ERα by an agonist, the DBD recognizes and binds to the estrogen response element in the promoter of estrogen-targeting genes, followed by the recruitment of cofactors to the targeted promoter by hERα. Thus, the proper interaction between DBD and its DNA element is a key regulatory step for hERα functions. Therefore, a recombinant hERα DBD was used as a target to select aptamers against the DBD.

An in vitro selection was started with an RNA pool (R50 pool) that was estimated to contain $3.4 \times 10^{15}$ individuals, which was the same as the RNA library used Example 1. Eight cycles of selection and amplification were carried out with a $His_6$-tagged DBD of human ERα (FIG. 7A) as the protein target. The expression and purification of the protein was described in the Materials and Methods. The selection involved 5 rounds of the typical cycle, while in three other cycles, an alternative matrix was used to immobilize the target protein in the positive selection to exclude filter-binding species. In cycles 3, 6 and 7, a metal affinity resin for $His_6$ tag, Profinity IMAC resins (Bio-Rad) was used to fix DBD in the positive selection, and a negative selection using both the resin and the filter paper was carried out to remove any matrix-binding RNA species. The procedures of both methods are described in the Materials and Methods. Several parameters were changed in the seven rounds of selection and amplification, as described in Table 6.

After 8 cycles of selection and amplification, radioactive RNA pools of Generation 3 to 8, were examined in a filter-binding assay to monitor the progression of selection. The binding reactions were set up with 200 nM $His_6$-tagged DBD. As shown in FIG. 7B, Generation 3 and 5 exhibited protein-dependent binding activity, which suggested that some aptamers had been selected and enriched. The signal of protein-independent binding showed up in Generations 7 and 8, indicating that some filter-binding sequence might have been enriched and competed out aptamers in the late cycles. Thus, Generation 5 pool will be used for in vitro selection for aptamers against DBD or, alternatively, it will be used for a new $6^{th}$ round of selection to enrich the aptamers further.

TABLE 5

In vitro selection against E2-liganded hERα

| Cycle | RNA | Pre-neg selection | GST/hERα-LBD | R:P | RNaseIn | Vol. | Time | Washing | Post-neg selection | RT-PCR | Rec. ratio | Trscpt |
|---|---|---|---|---|---|---|---|---|---|---|---|---|
| 1 | 3 nmole<br>100 µg | — | 98 pmol<br>1 µM E2 | 30:1 | Y | 1 ml | 2.5 hr | 5 ml | — | 2*20 µl RT<br>400 µl PCR | 20 ng<br>0.6% | 40 µl<br>160 µg |
| 2 | 1.5 nmole<br>50 µg | — | 49 pmole<br>1 µM E2 | 30:1 | Y | 0.5 ml | 1 hr | 10 ml | — | 20 µl RT<br>200 µl PCR | 20 ng<br>1.2% | 20 µl<br>40 µg |
| 3 | 0.6 nmole<br>20 µg | NaCl/<br>$MgCl_2$ | 20 pmole<br>1 µM E2 | 30:1 | Y | 0.5 ml | 0.5 hr | 13 ml | NaCl/$MgCl_2$ | 20 µl RT<br>400 µl PCR | 80 ng<br>24% | 20 µl<br>20 µg |
| 4 | 3 pmole<br>100 ng | NaCl/<br>$MgCl_2$ | — | — | — | — | — | — | KCl/$MgCl_2$ | 20 µl RT<br>200 µl PCR | ~200 ng<br>~200% | 20 µl<br>80 µg |
| 5 | 0.3 nmole<br>10 µg | | 6 pmole<br>1 µM E2 | 50:1 | N | 0.5 ml | 0.5 hr | 14 ml | NaCl/$MgCl_2$;<br>KCl/$MgCl_2$ | 20 µl RT<br>200 µl PCR | 80 ng<br>40% | 20 µl<br>80 µg |
| 6 | 0.3 nmole<br>10 µg | — | 6 pmole<br>1 µM E2 | 50:1 | N | 0.5 ml | 0.5 hr | 16 ml | NaCl/$MgCl_2$;<br>KCl/$MgCl_2$ | 20 µl RT<br>200 µl PCR | 88 ng<br>44% | 20 µl<br>80 µg |
| 7 | 0.3 nmole<br>10 µg | — | 6 pmole<br>1 µM E2 | 50:1 | N | 0.5 ml | 0.5 hr | 16 ml | NaCl/$MgCl_2$;<br>KCl/$MgCl_2$ | 40 µl RT<br>400 µl PCR | 176 ng | 20 µl<br>80 µg |
| 8 | 0.3 nmole<br>10 µg | — | 6 pmole<br>1 µM E2 | 50:1 | N | 0.5 ml | 0.5 hr | 16 ml | NaCl/$MgCl_2$;<br>KCl/$MgCl_2$ | 20 µl RT<br>200 µl PCR | 176 ng<br>80% | 20 µl<br>80 µg |

TABLE 5-continued

In vitro selection against E2-liganded hERα

| | | | Positive selection | | | | | | | | |
|---|---|---|---|---|---|---|---|---|---|---|---|
| Cycle | RNA | Pre-neg selection | GST/hERα-LBD | R:P | RNaseIn | Vol. | Time | Wash-ing | Post-neg selection | RT-PCR | Rec. ratio | Trscpt |
| 9 | 0.3 nmole 10 µg | — | 6 pmole 1 µM E2 | 50:1 | N | 0.5 ml | 1 hr | 16 ml | NaO/MgCl₂; KCl/MgCl₂ | 20 µl RT 200 µl PCR | 20 ng 10% | |

Cycle = cycle number; RNA = amount of pool RNA; GST/hERα-LBD [Invitro.] = protein target used, purchased from Invitrogen, 4.9 mM with 1 µM E2 (17β-estradiol); R:P = pool RNA to target protein ratio; RNaseIn = whether RNase inhibitor was added in the binding reaction, Y = yes, N = no; Vol. = volume of the binding reaction; Time = incubation time for the binding reaction; Washing = volume of the washing buffer (containing 1 µM E2) used; RT-PCR = volume of RT-PCR; Rec. ratio = amount of RNA retrieved at the end of each cycle and the fraction of bound protein; Trscpt = volume of RNA transcription reaction and estimated yield. Pre-neg selection and Post-neg selection = if a negative selection was carried out before or after the positive selection, the ions in binding buffer were indicated, NaCl/MgCl₂ represent 1xbuffer containing 150 mM NaCl, 10 mM MgCl₂ and 12 mM HEPES/pH 7.6; KCl/MgCl₂ represent 1x buffer containing 150 mM KCl, 10 mM MgCl₂ and 12 mM HEPES/pH 7.6. The method was the typical negative selection using filter papers to attract filter-binding RNAs, as described in the Materials and Methods.

TABLE 6

In vitro selection against His₆-tagged hERα-DBD

| | | Positive selection | | | | | | Post-neg | | Rec. | |
|---|---|---|---|---|---|---|---|---|---|---|---|
| Cycle | RNA | 6His/hERα-DBD | R:P | Matrix | Vol. | Time | Washing | selection | ET-PCR | ratio | Trscpt |
| 1 | 5.6 nmole 188 µg | 150 pmol | 37:1 | Filter | 1 ml | 1 hr | 8 ml | — | 2*20 µl RT 400 µl PCR | 800 ng 15.7% | 40 µl 160 µg |
| 2 | 1.5 nmole 50 µg | 75 pmole | 20:1 | Filter | 0.5 ml | 0.5 hr | 15 ml | — | 20 µl RT 200 µl PCR | 150 ng 6% | 20 µl 40 µg |
| 3 | 0.6 nmole 20 µg | 90 pmole | — | Bead | 0.5 ml | 0.5 hr | 0.5 × 5 ml | Bead Filter | 20 µl RT 400 µl PCR | 40 ng | 20 µl 20 µg |
| 4 | 0.3 nmole 10 µg | 15 pmole | 20:1 | Filter | 0.5 ml | 0.5 hr | 15 ml | Filter | 20 µl RT 200 µl PCR | 20 ng 4% | 20 µl 40 µg |
| 5 | 0.3 nmole 10 µg | 15 pmole | 20:1 | Filter | 0.5 ml | 0.5 hr | 16 ml | Filter | 20 µl RT 200 µl PCR | 20 ng 4% | 20 µl 55% |
| 6 | 0.3 nmole 10 µg | 90 pmole | — | Bead | 0.5 ml | 0.5 hr | 0.5 × 5 ml | Bead Filter | 20 µl RT 200 µl PCR | 20 ng | 20 µl 80 µg |
| 7 | 0.3 nmole 10 µg | 90 pmole | — | Bead | 0.5 ml | 0.5 hr | 0.5 × 5 ml | Bead Filter | 20 µl RT 200 µl PCR | 16 ng | 20 µl 80 µg |
| 8 | 0.3 nmole 10 µg | 15 pmole | 20:1 | Filter | 0.5 ml | 0.5 hr | 15 ml | Filter | 20 µl RT 200 µl PCR | 160 ng 32% | |

Cycle = cycle number; RNA = amount of pool RNA; His/hERα-DBD = protein target used, 1 µM; R:P = pool RNA to target protein ratio; Matrix = partitioning matrix used in a positive selection. Vol. = volume of the binding reaction in ml; Time = incubation time for the binding reaction in hour (hr); Washing = volume of the washing buffer used; RT-PCR = volume of RT-PCR; Rec. ratio = amount of RNA retrieved at the end of each cycle and the fraction of bound protein; Trscpt = volume of RNA transcription reaction and estimated yield. Post-neg selection = method of post-neg selection, either "beads & filter" or the "filter" alone. The method of "Filter" was the typical negative selection using filter papers to attract filter-binding RNAs, as described in the Materials and Methods. The 1x binding buffer used contains 150 mM NaCl, 10 mM MgCl₂ and 12 mM HEPES/pH 7.6. The method of "beads & filter" was described in the Materials and Methods.

Example 3—Characterizing Binding Affinity and Specificity of the hERα Aptamers

Figure 8A:
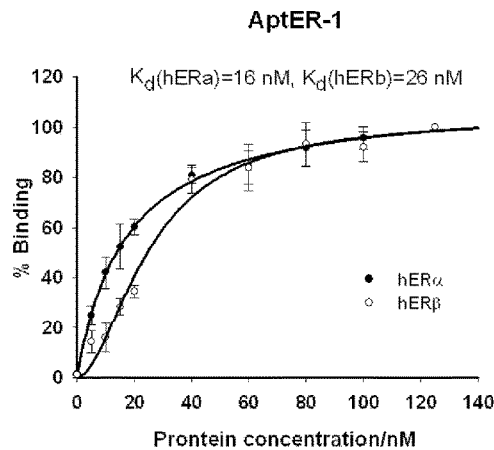
FIGS. 8A-E illustrate the binding affinity of the hERα aptamers.
Figure 8B:
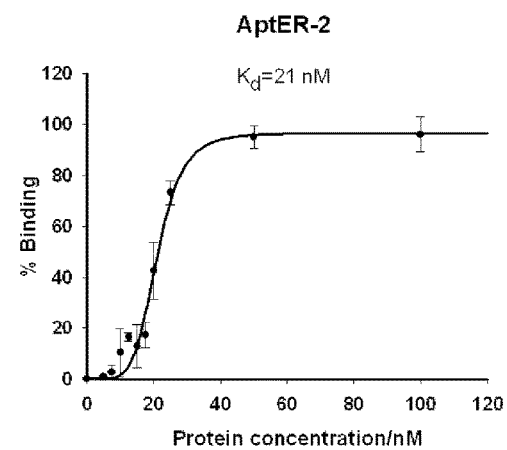
Figure 8C:
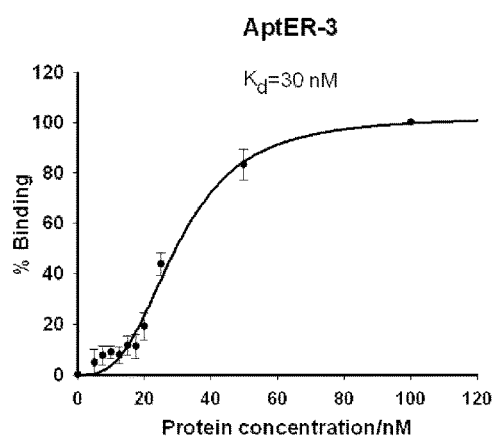
Figure 8D:
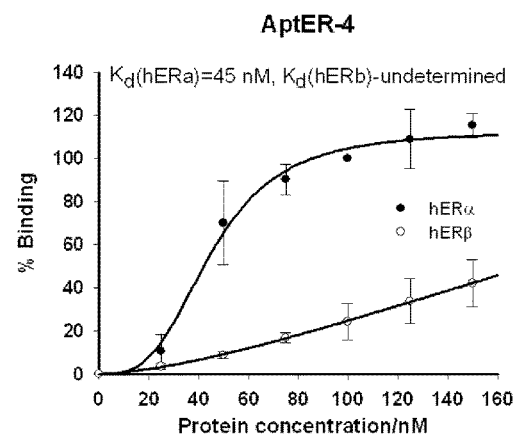

The dissociation constant ($K_d$) of the AptER-1, -2, -3, and -4 were measured using a nitrocellulose filter binding assay. A constant trace amount of [γ-$^{32}$P]-CTP incorporated RNA aptamer (~0.1 nM) was titrated with increasing amounts of the target protein ranging from 5 to 150 nM. The binding activity at each concentration was determined as % binding, by calculating the radioactive signal of the RNA-protein complex retained on the filter as a percentage of the signal at the highest protein concentration (saturated) used. The assays were performed in triplicates for each aptamer. A binding curve was constructed using Sigma Plot 9.0.1, with average binding affinity (% binding) as a function of the protein concentration using a sigmoidal equation (Hill equation, 3 parameters). Apparent $K_d$ was the protein concentration where half of the maximal binding activity was achieved, and were calculated from the data points by using Sigma Plot. AptER-1 showed the highest affinity to hERα, with a $K_d$ at around 16 nM (FIG. 8A); AptER-2 ranked second, with a $K_d$ of 21 nM (FIG. 8B); AptER-3 ranked third, with its $K_d$ at 30 nM (FIG. 8C); AptER-4 appeared to have the lowest affinity, with $K_d$ at around 45 nM (FIG. 8D). The first 3 aptamers were isolated in in vitro selection I, and their affinity rank explains the relative abundance in the final selected library. More specifically, it is believed that AptER-1 dominated the final selected pool because it was the strongest binder. AptER-4 was the weakest binder, and would not have been easily identified in the selection I libraries.

Figure 8E:
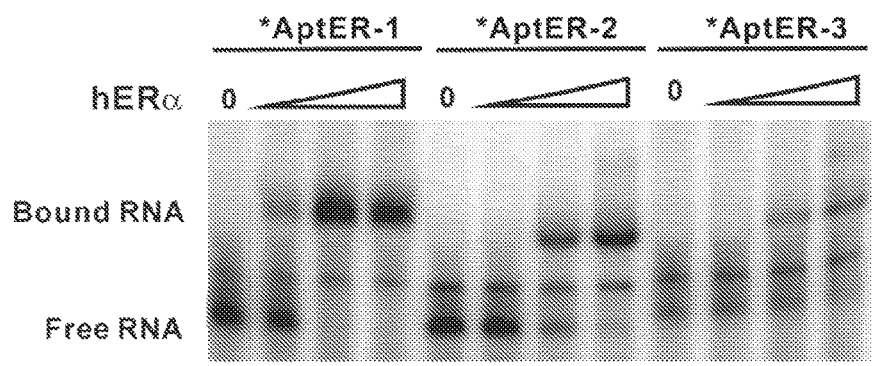

The affinities of AptER-1, -2 and -3 to hERα were also compared in a band shift assay (FIG. 8E). Radioactive RNA aptamers were incubated with 0, 10, 20 or 40 nM of hERα, and the fraction of shifted aptamers at each protein concentration was compared among the three aptamers. At 20 nM, an obvious shifted band by AptER-1 showed up, whereas neither AptER-2 nor AptER-3 were shifted at this concentration, confirming that the affinity of AptER-1 was the highest among the three. The supershifted bands observed in the AptER-2 and AptER-3 binding reactions with the highest protein concentration and the multiple shifted bands in AptER-4 binding reaction suggested more than one RNA bound to the protein. This agreed with their sigmoid binding curves and their calculated Hill coefficients (n>1, positive cooperation). In contrast, AptER-1 has a Hill coefficient approximate to 1 and no supershifted band was observed.

There are two forms of human estrogen receptor, hERα and hERβ. The overall homology between hERα and hERβ is 47%, with the highest homology in the DNA-binding domain (96% identity) and much lower homology in the other domains.

Figure 9A:
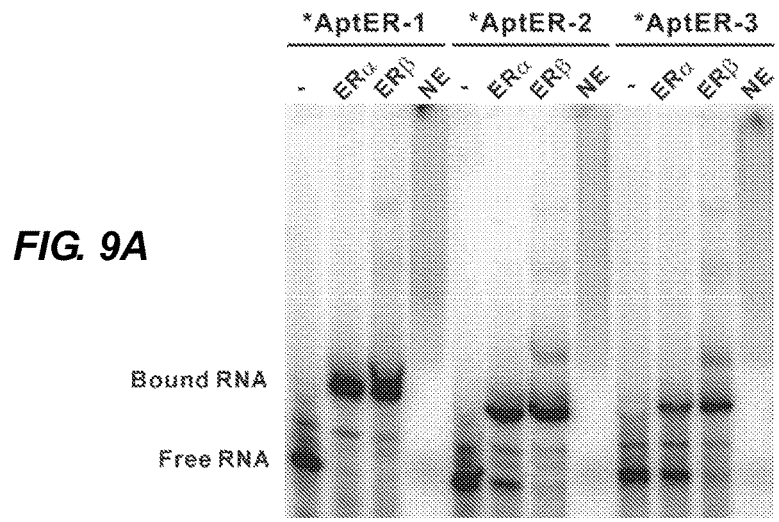
FIGS. 9A-B illustrate the binding specificity of AptER-1, -2 and -3.
Figure 9B:
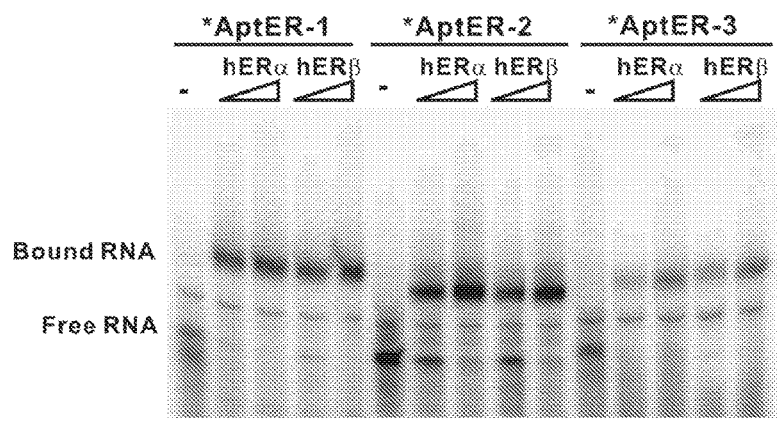

To examine the binding specificity of the first set of isolated aptamers, AptER-1, -2 and -3, proteins were presented at high concentrations in ESMA, including hERβ at 200 nM or HeLa nuclear extract at 200 μg/ml, which should allow detection of weak binding activity. As shown in FIG. 9A, the three aptamers bind specifically to hERβ and showed a very similar pattern to that of hERα. This was confirmed in a second EMSA using the two ER subtypes at the same concentrations (FIG. 9B). Furthermore, the binding affinities to the two forms were very close, as shown in the EMSA, and this was more carefully compared with the binding curves of AptER-1 (FIG. 8A). The $K_d$ of hERβ was determined to be around 26 nM. In the presence of HeLa nuclear extract (FIG. 9A), no specific shifted band could be observed. These data indicate that the three aptamers are specific to human ERs, and do not have detectable affinity to other nuclear proteins in human cells.

Remarkably, when comparing the binding affinities of AptER-4 to the two ERs (FIG. 8A), $K_d$ of hERα was 45 nM, while $K_d$ of hERβ was too low to be undertermined. This indicates that AptER-4 bound to a site of low homology between the two hERs, and was able to distinguish the two forms of ER. Thus, AptER-1 and AptER-4 do not share a common binding site.

Figure 10A:
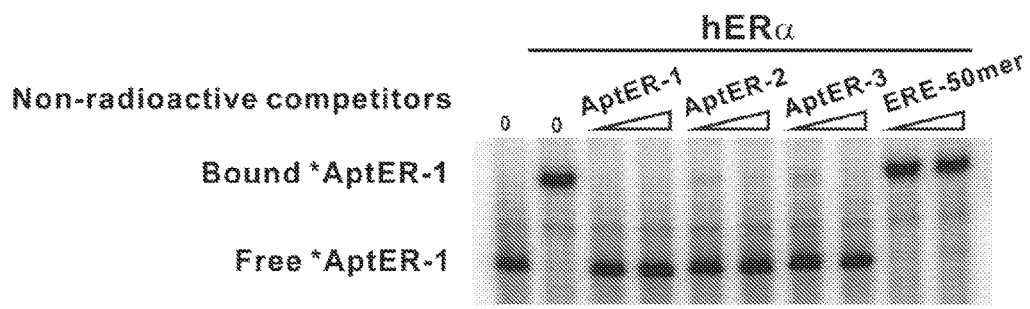
FIGS. 10A-D illustrate the binding sites of the hERα aptamers.

The mobility of a RNA-protein complex is usually determined by a combination of its mass, charge, and shape. In this case, as the aptamers are of similar size and charge, it can be inferred that the shape may be the major contributing factor in determining its mobility. The mobility of the shifted bands by the three Class I aptamers was almost the same (FIG. 8E), indicating that their binding sites on hERα are likely to significantly overlap. To test whether they share a binding site, a cross competition assay was performed between radiolabeled AptER-1 and nonradioactive aptamers AptER-1, -2 and -3. Radiolabeled AptER-1 RNA at 0.1 nM was competed by 2000× or 8000× more concentrated nonradioactive competitors AptER-1, -2 or -3 RNA for binding to hERα presented at 20 nM. As shown in FIG. 10A, AptER-1 was partially outcompeted by 2000× more concentrated AptER-2 or AptER-3 and totally outcompeted by both aptamers at the higher concentration, which indicated that their binding sites significantly overlapped. Furthermore, self-competition between radiolabeled AptER-1 and unlabeled AptER-1 showed that 2000× more concentrated cold AptER-1 is enough to totally compete out the radiolabeled RNAs. Thus, the relative strength in competition among the three cold aptamer competitors seemed to correlate well with their binding affinities. As these three aptamers apparently share a binding site on hERα, they are considered to belong to one single class, designated Class I. The tightest binder, AptER-1, was chosen to represent Class I aptamers in the future assays.

Figure 10B:
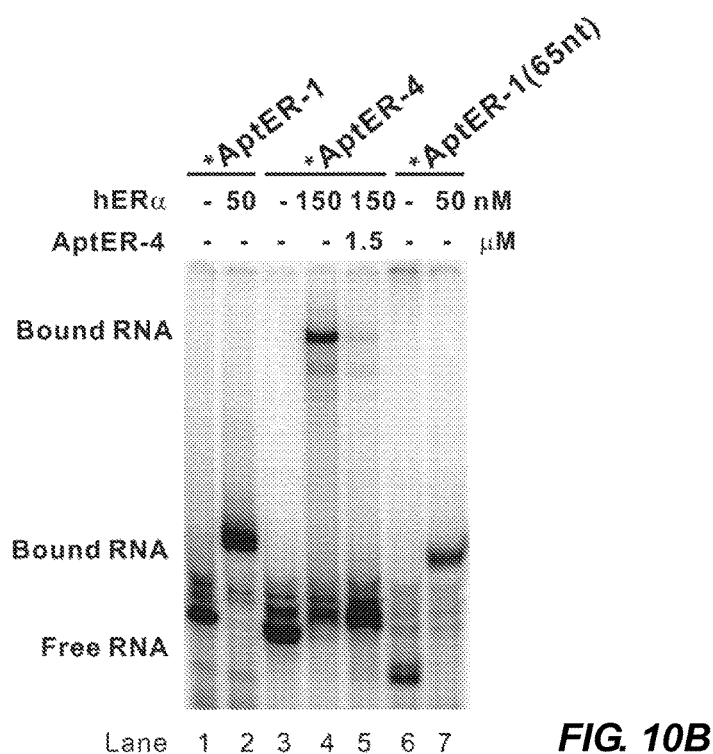

Compared with AptER-1, the shifted band by AptER-4 moved at much lower mobility than that of AptER-1 (FIG. 10B lanes 1-4). This indicated that AptER-4 bound to a different site on hERα from Class I aptamers. This possibility was examined by performing cross competition assays in two ways. First, a nonradiolabeled truncated version of AptER-1, AptER-1(65nt) (SEQ ID NO: 5), was included as a competitor in the binding reaction between radiolabeled AptER-4 RNA and hERα. AptER-1(65nt) is 65nt long and has full activity of AptER-1. Radioactive AptER-4 at around 0.5 nM was competed by 1.51 μM nonradioactive AptER-1(65nt) (3000× more concentrated than AptER-4) for binding to hERα present at 150 nM (FIG. 10B, lanes 3-5). One group of reactions set up with radiolabeled AptER-1(65nt) (FIG. 10B, lanes 6-7) were included to serve as a positive control of binding between AptER-1(65nt) and hERα. RNAs were reconstituted separately and mixed together before being incubated with hERα. The binding reactions were subjected to EMSA (4.8% polyacrylamide gel (acrylamide:bis-acrylamide=37.5:1) in ¼×TBE buffer). As shown in FIG. 10B, in the presence of the nonradioactive competitor AptER-1(65nt) (lane 5), the signal intensity of AptER-4-hERα complex was significantly reduced, while a second band, with slightly lower mobility than free AptER-4 showed up.

Figure 10C:
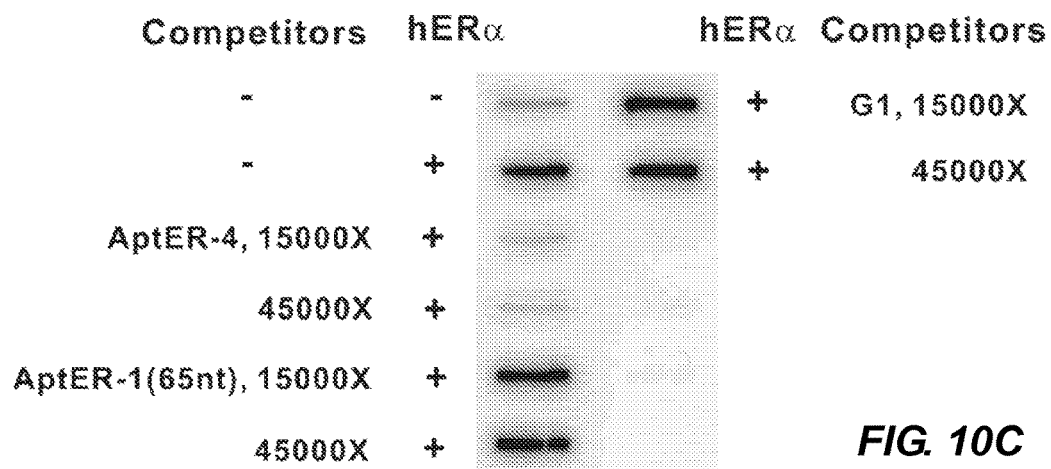

To confirm whether (i) a super complex formed by AptER-4, hERα and AptER-1(65nt) or (ii) free radiolabeled AptER-4 was outcompeted by AptER-1(65nt), a second cross competition assay in the form of a filter-binding assay was performed to distinguish protein-bound RNA from free RNA (FIG. 10C). Radioactive AptER-4 at around 0.1 nM was competed by 1.5 μM or 4.5 μM nonradioactive AptER-1(65nt) for binding to hERα present at 100 nM. Two controls for competition specificity were included using the nonradioactive AptER-4 and Generation I pool of E2-LBD selection (G1) as competitors (see Example 2, supra). The former served as a positive control of self-competition, whereas the latter served as a negative control of competition. RNAs were reconstituted separately and mixed together before incubated with hERα. The binding reactions were subjected to filter-binding analysis. As shown in FIG. 10C, nonradioactive AptER-4 at both concentrations competed out the radioactive ones, while the RNA pool did not affect filter-binding of the AptER-4-hERα complex. AptER-1(65nt) at neither concentration interfered with the binding of AptER-4 to hERα. This indicated that the binding sites of AptER-1 and AptER-4 on hERα did not significantly overlap. It also indicated that AptER-4, AptER-1(65nt) and hERα might form a super complex (FIG. 10B, lane 5).

Figure 10D:
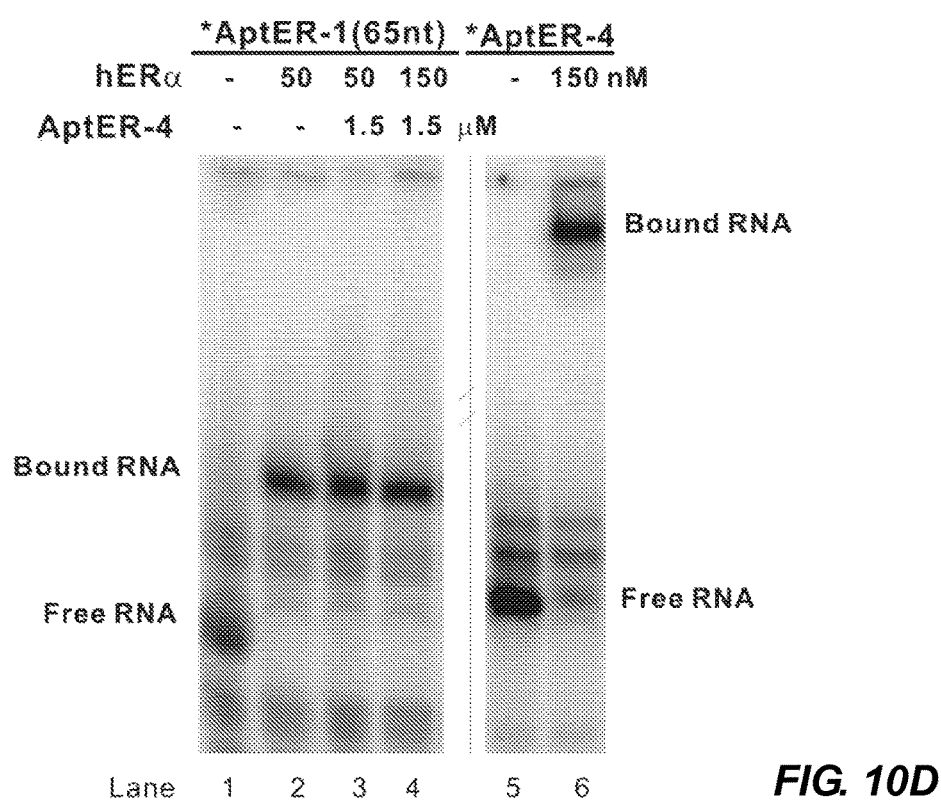

Nonradiolabeled AptER-4 was also used as a competitor in a binding reaction between radiolabeled AptER-1(65nt) and hERα. In the presence of hERα at 150 nM, radioactive AptER-4 (lane 7) at 1 nM bound to hERα (FIG. 10D, lanes 5 & 6). When 1.5 μM nonradioactive AptER-4 were added to compete with 1 nM radioactive AptER-1(65nt) in the presence of 50 or 150 nM hERα (lanes 1-4), it did not disrupt the hERα-AptER-1(65nt) complex, which agreed with the results mentioned above. However, no super complex was formed as FIG. 10B, lane 5, although EMSA was done under the same gel conditions. Considering these data together, AptER-1 and AptER-4 appeared not to share a common binding site on hERα, but whether they could form a stable triple complex with hERα remains unclear.

As AptER-4 apparently recognized a distinct site on hERα from the binding site of AptER-1, it belonged to a second class, designated Class II. This also indicated that the second in vitro selection strategy did divert aptamers against exposed surfaces of the target protein outside the marked site, and enhanced the chance of obtaining aptamers to a distinct binding site.

Example 4—Probing the Aptamer-Binding Sites on hERα

Binding sites on hERα recognized by the two classes of aptamers were examined using binding assays with available well-characterized structural domains of ERα, such as hERα-DBD and hERα-LBD, or cross-competition assays with natural ligands of hERα as competitors. Expression constructs of hERα-DBD and ERα-LBD were obtained from the laboratory of W. L. Kraus (Cornell University), and the recombinant hERα-DBD was overexpressed in E. coli BL21(DE3) and purified as described in the Materials and Methods (see FIGS. 4A, 7A).

Figure 11A:
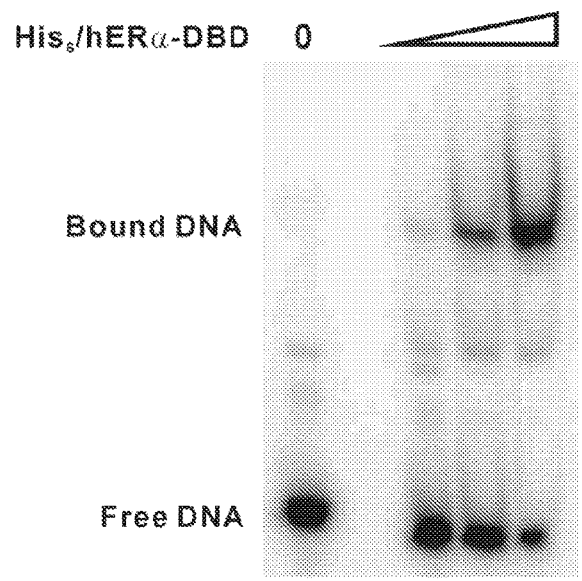
FIGS. 11A-D show that the aptamers did not bind to hERα-DBD.
Figure 11B:
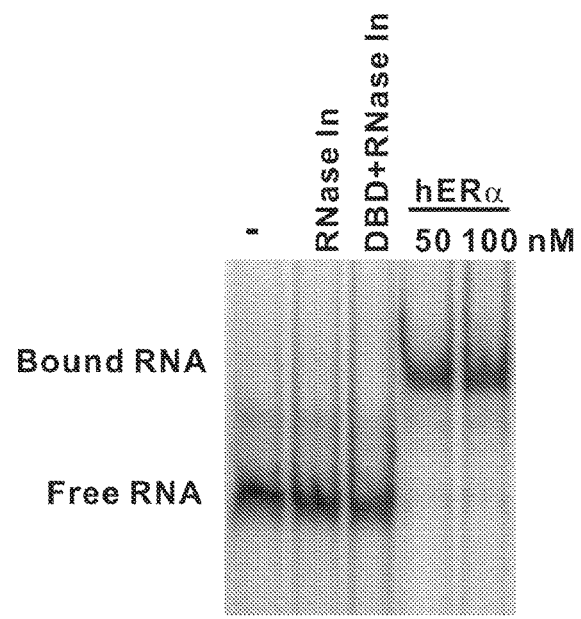

Class I aptamers bound with similar affinities to both subtypes of ER, which share the highest homology (96%) in the DBD. This raised the possibility that the target site of Class I aptamers was located within the DBD. Whether the aptamers bind to the DBD was tested in binding assays using a recombinant hERα-DBD. It was expressed as a $His_6$-tagged fusion protein in *E. coli* BL21 (DE3) and purified as described in the Materials and Methods. To verify its ERE-binding capability, a DNA EMSA was performed. DNA oligo ERE-50mer contains a GAAA tetra loop, which forces the oligo to form a hairpin. A copy of *Xenopus laevis* vitellogenin A2 ERE (5'-GGTCACAGTGACC-3', SEQ ID NO: 73) was presented in the stem of a hairpin. Human ERα-DBD at around 100, 200 or 400 nM was incubated with 5 nM ERE-50mer, and the binding reaction was electrophorised in 4.8% polyacrylamide gel (50:1) in ½×TGB (12.5 mM Tris base, 100 mM glycine). As shown in FIG. 11A, His-tagged DBD bound to 5'-radiolabled ERE-50mer as expected. However, in both EMSA (FIG. 11B) and filter-binding assay, no association was detected between AptER-1 and DBD. AptER-4 was also subjected to DBD binding assay and proven not to bind.

Figure 11C:
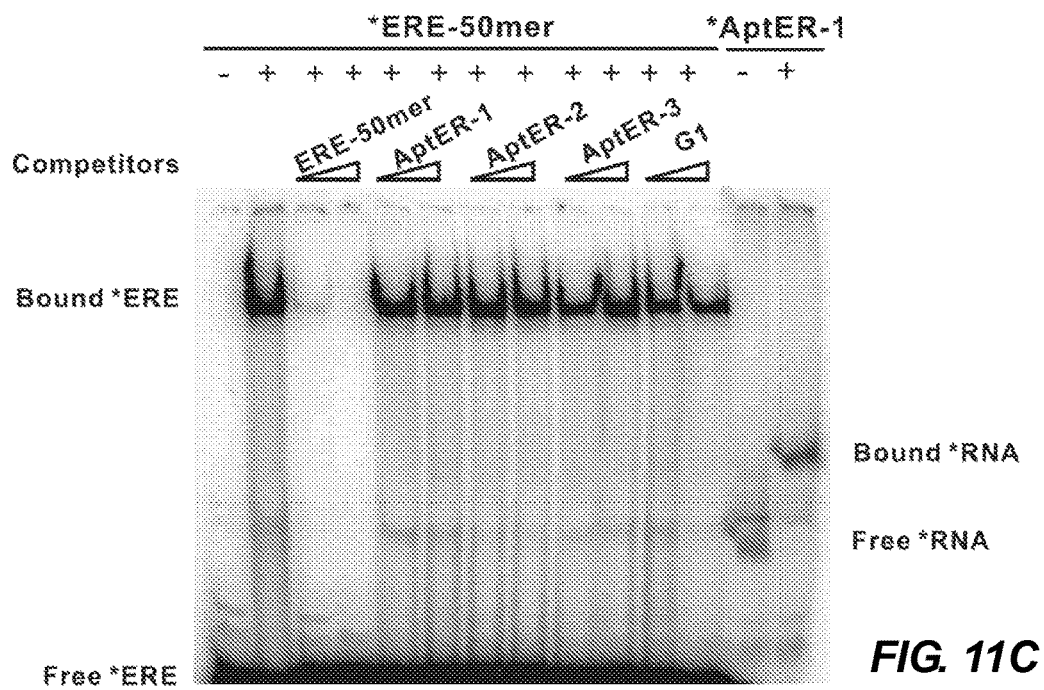

Whether the aptamers bind to the DNA binding site on the full-length hERα was tested in cross-competition assays using ERE-50mer as a specific competitor. Radiolabeled ERE-50mer was competed with 100× or 400× more concentrated nonradioactive competitors ERE-50mer, AptER-1, -2, -3 or Generation 1 pool of hERα selection G1 (see Example 1). Radiolabeled ERE-50mer at 5 nM was mixed with the competitors before the addition of hERα at 50 nM. The binding reaction was set up as described in the Materials and Methods, and electrophorised in a 4.8% polyacrylamide gel (acrylamide:bis-acrylamide=50:1) in ½ ΔTGB. ERE-50mer served as a positive control of competition, whereas the G1 pool was a negative control. A positive control using 0.5 nM radioactive AptER-1 and 50 nM hERα was set up in the same way to demonstrate aptamer binding activity. As shown in FIG. 11C, unlabeled ERE-50mer occluded the binding of radiolabeled ERE-50mer to human ERα, whereas none of the aptamers or the early generation pool G1 could affect ER-ERE complex. This agreed with the result from a second cross-competition assay between radiolabeled AptER-1 and unlabeled ERE-50mer for binding to human ERα (FIG. 9A). Radiolabeled AptER-1 RNA was not interfered by 2000× or 8000× more concentrated cold competitor ERE-50mer in the binding reactions. These results indicated that the Class I aptamers did not bind to the DBD.

Figure 11D:
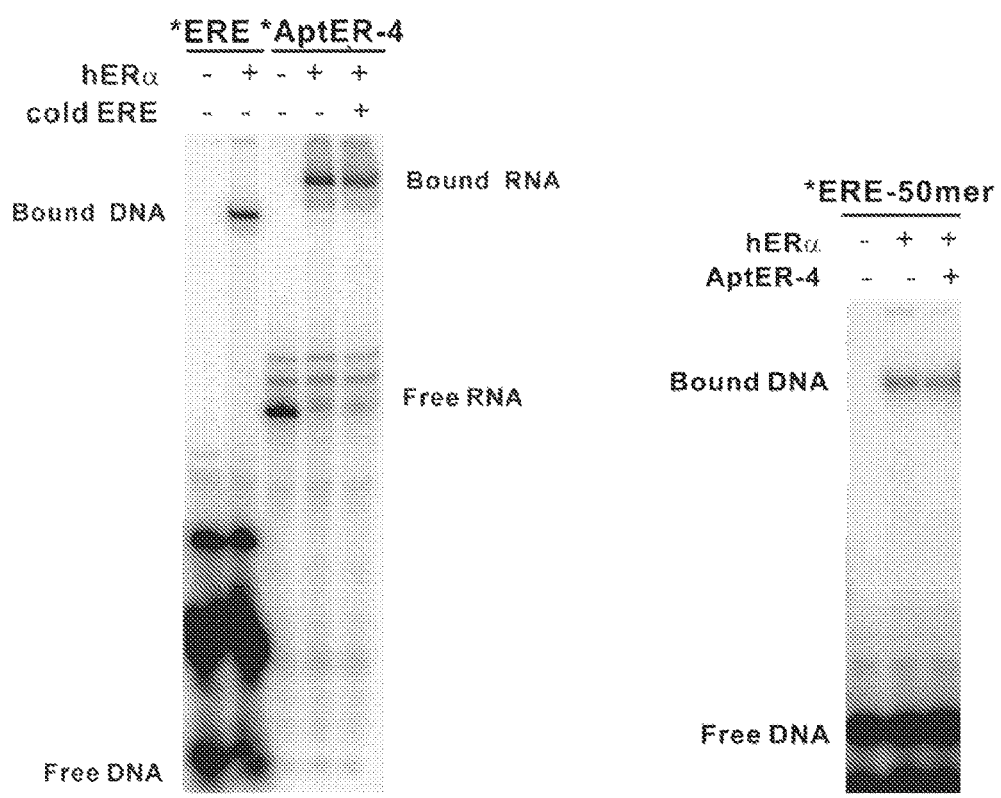

Whether AptER-4 binds to the DNA binding site was also tested in cross-competition assays in these two ways. In the first competition assay, radiolabeled AptER-4 at 0.5 nM was challenged by 3000× more concentrated unlabeled ERE-50mer for binding to hERα present at 150 nM. A positive control of ERE-hERα binding was set up with 5 nM radioactive ERE-50mer and 150 nM hERα. The reaction was resolved on a 4.8% polyacrylamide gel (50:1) in ¼× TBE buffer. As shown in FIG. 11D, left, radiolabeled ERE-50mer bound to hERα, but its unlabeled counterpart did not interfere with AptER-4-hERα binding. In a second competition assay, radiolabeled ERE-50mer at 5 nM was competed by 300× more concentrated competitor AptER-4 in the presence of 50 nM hERα. As shown in FIG. 11D, right panel, AptER-4 did not disrupt the hERα-ERE complex. These results indicated that AptER-4 also did not bind to the DNA binding site.

Figure 12A:
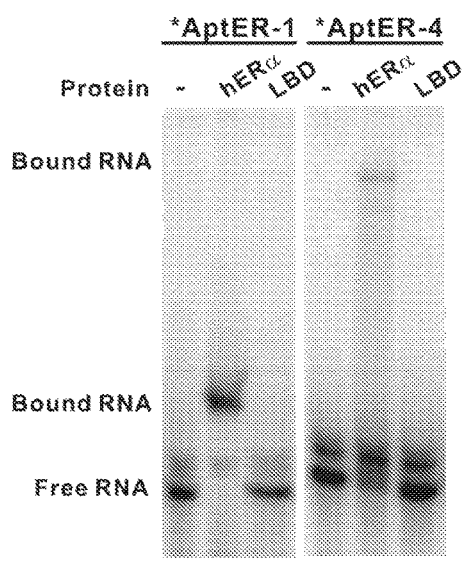
FIGS. 12A-C illustrate that the aptamers did not bind to hERα-LBD.

Whether the aptamers bind to LBD was examined in two ways. One approach was an EMSA to directly examine whether the aptamers bound to the GST/hERα-LBD construct. The recombinant human ERα-LBD purchased from Invitrogen was expressed as a GST-tagged fusion protein in baculovirus-infected insect cells. It contains amino acid 282 to 595 of hERα, with a calculated molecular weight of 62.80 kDa protein. According to the manufacturer's instruction, the concentration of functional receptor was determined by quantification of estrodial, [6, 7-$^3$H9(N)] receptor complexes using a hydroxyapatite (HAP) assay. Binding reactions were set up with 2.5 nM radiolabeled aptamers and 100 nM protein. The binding reactions were electrophoresed on a 4.8% polyacrylamide gel (50:1) in ¼×TBE buffer. Both AptER-1 and AptER-4 exhibited binding activity to hERα in the positive controls. In contrast, neither AptER-1 nor AptER-4 recognized GST/hERα-LBD (FIG. 12A).

Figure 12C:
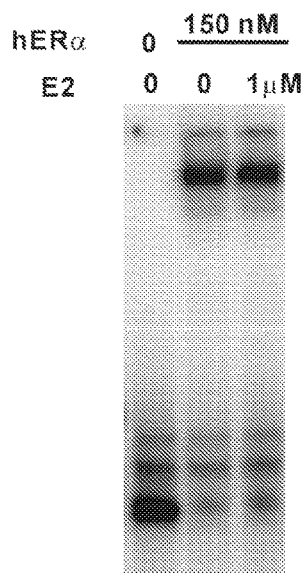
Figure 12B:
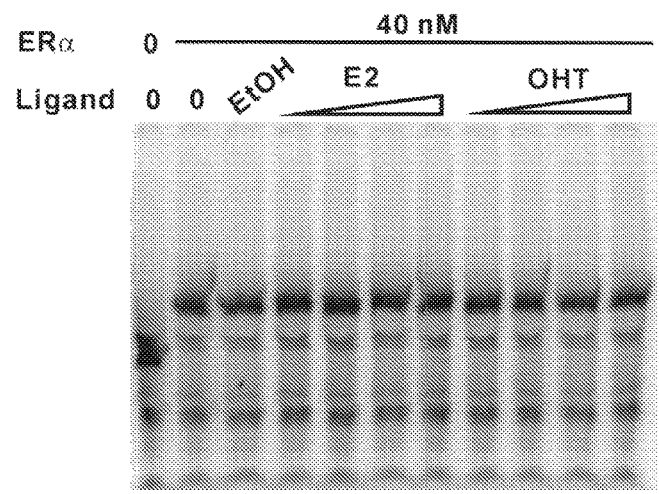

The other approach was a ligand competition assay to investigate whether the interaction between aptamers and hERα was intervened by ligand-binding, using 17β-estradiol (E2) or 4-hydroxytamoxifen (OHT). Human ERα at 40 nM was incubated with ligands or equal volume of vehicle control (EtOH) in 16 µl at 37° C. for 10 min before addition of RNA (final concentration of 2.5 nM) to make a 20 µl binding reaction. As shown in FIG. 12B, in the absence and presence of 40 nM to 5 µM E2 or OHT, hERα formed a complex with AptER-1 in the same way. Similar assays were done for AptER-4. In a binding reaction set up with AptER-4 at 1 nM and hERα at 150 nM, the presence of 1 µM E2 did not interfere with the binding between hERα and AptER-4 (FIG. 12C). Thus, the both classes of aptamers bound to hERα with its LBD in any ligand-bound state, indicating that they do not bind to the LBD of ERα.

From the foregoing, it is believed that both Class I and Class II aptamers bind to sites that are not only distinct of one another, but also distinct of the DBD and LBD.

Example 5—Determination of Minimal Binding Sequences

To determine the minimum RNA sequence required for aptamer function, deletion analysis was performed on AptER-1 and AptER-4. With the help of the predicted secondary structures, the approximate boundaries at 5' and 3' termini of the sequence required for aptamer activity were determined. Oligonucleotides were designed to generate DNA templates of truncated constructs either by PCR with the full-length aptamer template to lift a region or by bi-directional primer extension. It is worth noting that the amount of the full-length template in the PCR based approach should be low (e.g., 1 ng/100 µl reaction) to avoid its presence in the RNA transcription reaction, which may result in contamination of full-length RNA aptamers in the binding assays. These short RNA transcripts were produced using in vitro transcription reactions from the templates, and their affinities to apo-hERα were assayed by filter-binding assay or EMSA.

Based on the predicted secondary structure of AptER-1 (FIG. 5A), the first minimized RNA construct was AptER-1(65nt) (FIG. 13A), containing the central stem loop region and excluding the whole 5' constant region and part of the 3' constant region. As described in the Materials and Methods, a pair of primers was used to lift the coding sequence. Three G residues were added to the 5' end of the predicted RNA transcript to ensure high T7 transcriptase efficiency. Three C residues were added to the RNA 3' end complementary to the triple Gs to stablize the stem. It was predicted to retain the AptER-1 central hairpin loop structure by the energy minimization algorithm of mFold. Its binding affinity was compared to the full length AptER-1 aptamer in a stardard EMSA, using 25 nM hERα. AptER-1(65nt) was shown to have full, or even better binding activity than the full length AptER-1 (FIG. 13C, compare sB63 vs. B63). Next, 6 base pairs were deleted in the stem between the triple GC pairs and the loop to make a smaller construct AptER-1(53nt). In EMSA with 35 nM hERα, AptER-1(53nt) was fully active but its transcription efficiency was much lower than the longer RNA. A further deletion of two GC pair in the stem using primer pair 6B1-B63f and ERApt-1 r-24nt generated a 48nt version, which totally lost its binding activity. Another truncated version of 34nt, generated with a primer pair ERApt-1f and ERApt-1r, did not show any binding activity either. Thus, these data indicated that formation of the central 53nt stem loop structure reinforced by a stable stem formed by base pairing of 5' and 3' end retained the aptamer activity, while the sequence in this endmost stem itself was not required for recognition by ER.

Among the nine individual clones of AptER-1 identified within the 54 individuals, there were three types of different sequence sharing a similarity of 98%. The one chosen to represent the consensus sequence is B63 (AptER-1, SEQ ID NO: 1), with 7 copies out of the nine clones, while the other two clones, B30 and B65 each showed 2 nucleotides substitution, in comparison with B63. B30 (SEQ ID NO: 11) had A51C and C68A substitutions, both within the central loop of AptER-1. As shown in FIG. 13C, the 65nt truncated B30 (sB30, SEQ ID NO: 13) showed lower affinity to hERα than sB63 (AptER-1(65nt), SEQ ID NO: 5). This is at least suggestive that the two regions were essential to the functional activity of AptER-1. The B65 substitutions of G38A and U100A were both outside the central loop regions, and did not cause any difference in binding affinity of the 65nt truncated B65 (sB65, SEQ ID NO: 14) in comparison with AptER-1(65nt). This evidence further supports the belief that the central 53nt stem loop was the minimal moiety of AptER-1, and the two sites corresponding to the substitutions in B30 affect optimal binding.

The secondary structure of the full length AptER-4 (SEQ ID NO: 4) was predicted to contain a three-way junction with 2 long hairpin stem loops and a third short stem formed by the 5' and 3' end (FIG. 5D). The 5' and the 3' constant regions are involved in one of the long stem loops. RNA deletion constructs were generated so as to contain only a single hairpin stem loop, but none retained binding activity. AptER-4 was therefore systematically truncated from both ends by 8 to 30 nucleotides at a time, yielding a total of 17 truncated AptER-4 between 42nt and 92nt in length (FIG. 13D), but all deletions abolished the affinity. These data indicated that the full length AptER-4 was required for efficient recognition by hERα.

Example 6—Construction of RNA Aptamer Dimer

Constructing a single composite molecule containing more than one copy of an aptamer would allow production of a large number of aptamers from a single transcript. Using the sequence of AptER-1(53nt), a divalent version, designated AptER-1×2(138nt), was constructed to emulate the bivalent form of natural antibodies.

Figure 14A:
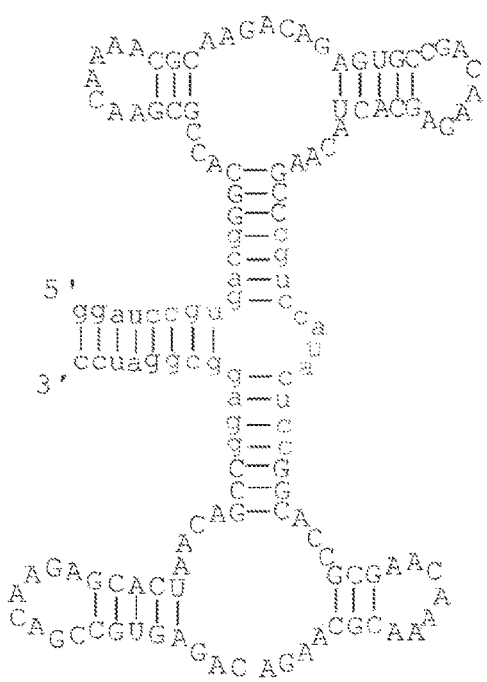

In the hairpin loop structure of AptER-1, sequences in the loop and formation of a stem by its flanking regions were shown to be involved in its binding activity. Thus, correct folding of each individual aptamer in a composite molecule should be maintained. However, repeated sequences in a simple concatemer often lead to misfolded individual aptamers. Thus, instead of simply connecting two copies of AptER-1 coding sequence in a tandem manners, well-characterized three-way junction elements were utilized to connect the two copies (Xu and Shi, "Composite RNA Aptamers as Functional Mimics of Proteins," Nucl Acids Res 37(9): 1-9 (2009), which is hereby incorporated by reference in its entirety). Use of the three-way junctions, with known co-axial stacking arrangements of branching stems, avoided base pairing between the stem sequence of the two units and, instead, promote proper folding. Copies of the minimized AptER-1(53nt) were grafted to two stems of the three-way junction of *Haloarcula marismortui* 5S RNA. The secondary structure of AptER-1×2(138nt) was predicted by free energy minimization algorithms of mFold (FIG. 14A), before the sequence was coded into DNA. The sequence of the gene for expressing AptER-1×2(138nt) contained the aptamer-dimer coding sequence and a T7 promoter. A set of oligonucleotides were designed and used to generate the DNA template by bi-directional primer extension. The products of primer extension yielded multiple bands and the band of expected size (138nt) was cut out and eluted from the polyacrilamide gel.

RNA transcripts of AptER-1×2(138nt) were produced by run-off in vitro transcription from the T7 promoter in the template, and labeled with [α-$^{32}$P]CTP. The overall affinity of AptER-1×2(138nt) to apo-hERα, in comparison to that of the monovalent AptER-1(65nt), was assayed by EMSA. As shown in FIG. 14B, the divalent aptamer bound to hERα more avidly than the monovalent aptamer. The $K_d$ of AptER-1(65nt) was around 30 nM, whereas about half of AptER-1×2(138nt) was shifted at a protein concentration lower than 15 nM. It represented a more than two-fold increase of the binding strength.

Example 7—Design and Construction of hERα Aptamer Expression Vectors for Mammalian Cell-Based Assays To achieve high-level aptamer expression, RNA pol III driven U6 or H1 promoters were used because they have been widely used to express functional RNAs such as ribozymes, siRNA and aptamers (Mi et al., "H1 RNA Polymerase III Promoter-driven Expression of an RNA Aptamer Leads to High-level Inhibition of Intracellular Protein Activity," *Nucleic Acids Res* 34(12): 3577-3584 (2006), which is hereby incorporated by reference in its entirety). In these systems, RNA transcription starts accurately at the initial purine base downstream of the 5' insertion site of coding gene and terminates at a RNA polymerase III terminator (six thymine residues), with addition of two uridine residues at the 3' end of the transcripts (FIG. 15A).

AptER-1 and AptER-4 were chosen to represent the two classes of aptamers in functional assays. Their truncated version, a 61-nt version of AptER-1 (FIG. 15B, SEQ ID NO: 8) and a truncated 97-nt AptER-4 (FIG. 15D, SEQ ID NO: 10) were constructed. AptER-1(61nt) contains the essential hairpin loop and a 6 bp stem from the original full-length AptER-1. An additional GC base pair was added to the distal end of the stem as transcription from a RNA polymerase III promoter initiates with a purine. The modified AptER-4 contained almost the entire sequence of the full length aptamer, except for the deletion of several unpaired nucleotides at the 5' and 3' ends. Sets of primers were designed and used to amplify the coding sequences from the full-length aptamers. To augment the efficacy of an individual RNA aptamer transcript, a divalent AptER-1 transcript—designated AptER-1×2(138nt), SEQ ID NO: 9—was formed, emulating the bivalent form of natural antibodies. The secondary structure of the designed construct was predicted by a free energy minimization algorithm of mFold to ensure the correct folding of each component in the composite structure (FIG. 15C). A pair of oligonucleotides were designed and used to amplify the coding sequence from AptER-1×2(138nt). As a negative control, a coding gene expressing a 48nt long short-hairpin RNA (shRNA) with sequence 5'-ACU ACC GUU GUU AUA GGU GUU CAA GAG ACA CCU AUA ACA ACG GUA GUU-3' (SEQ ID NO: 74) was cloned into each vector. The coding sequence was originally provided in the pSilencer 3.1-H1.puro kit purchased from Applied Biosystems. According to the manufacturer's instruction, it has limited homology to any known sequences in the human, mouse and rat genomes. Six thymidines were added to the 3' end of aptamer coding sequence as a RNA pol III terminator. Thus, all RNA transcripts are devoid at the 3' end of any additional flanking sequences from the vector that might alter the functional conformation of the expressed aptamer. As described in the Materials and Methods, oligonucleotides and DNA fragments were synthesized according to the sequences and pieced together to form the DNA template, which was then cloned into vectors at a site between the promoter and the terminator. Based on RNA structure predictions, the additional two uridines should have minimal effect on aptamer folding (FIGS. 15B-D).

Three RNA expression vectors, pSHAG-MAGIC (Paddison et al., "A Resource for Large-scale RNA-interference-based Screens in Mammals," Nature 428(6981):427-431 (2004), which is hereby incorporated by reference in its entirety), pSUPER.retro.puro (OligoEngine) and pSilencer 3.1-H1.puro were adapted for RNA aptamer expression, and compared their performance. Each was originally used for short hairpin RNA expression in mammalian systems. pSUPER and pSilencer vectors carry a RNA polymerase III H1-RNA gene promoter, whereas pSHAG-MAGIC contains a U6-RNA gene promoter. The construction strategy of RNA aptamer expression cassette was described in detail in the Materials and Methods. Individual plasmids used in the following assays were sequenced to ensure the fidelity of coding genes.

Aptamer expression vectors were introduced into mammalian cell lines by transient transfection. To determine whether the aptamer expression vectors could produce the RNA aptamers, total RNA from expression vector-transfected cell lines were subjected to real time RT-PCR to evaluate the accumulation level of the expressed aptamers in living cells in a time course.

Expression and accumulation of AptER-1×2 from pSUPER were examined in two cell lines, HEK293FT and hERα-positive breast cancer cell line MCF7. Twenty-four hours before the transfection, cells were seeded at proper densities into 35 mm dishes, allowing the cells to reach a similar density (no confluency) when harvested. A transfection reaction for a 35 mm dish consisted of 0.4 μg aptamer expression construct, 0.1 μg MSCV-Puro/EGFP vector expressing green fluorescent protein (EGFP) and 1.5 μl of FuGene HD (Roche), and was set up as recommended by the manufacturer. Co-transfection of the EGFP expression vector allowed monitoring the transfection efficiency.

pSUPER/AptER-1×2 expression vector-transfected cells were harvested in TRIzol (Invitrogen) at several time points post-transfection, and total RNA was extracted using RNeasy Plus Mini Kit (QIAgen) following the manufactory's instruction. For MCF7, six sampling time points were included in the assay, i.e., 12 h, 24 h, 36 h, 48 h, 72 h and 96 h post-transfection. From each sample, 1 μg of total RNA was used to make first strand cDNA, using oligo dT (15mer) and AptER-1×2 specific reverse primer as primers. A small fraction (1/20) of the first strand cDNA was used as the template for real time PCR, which were run using standard conditions, as described in the Materials and Methods. Aptamer levels were normalized against beta-actin control and expressed as folds of beta-actin levels. The aptamer level was plotted as a function of time. For HEK293FT, four sampling time points were included, i.e., 24 h, 48 h, 72 h and 96 h post-transfection.

Figure 16:
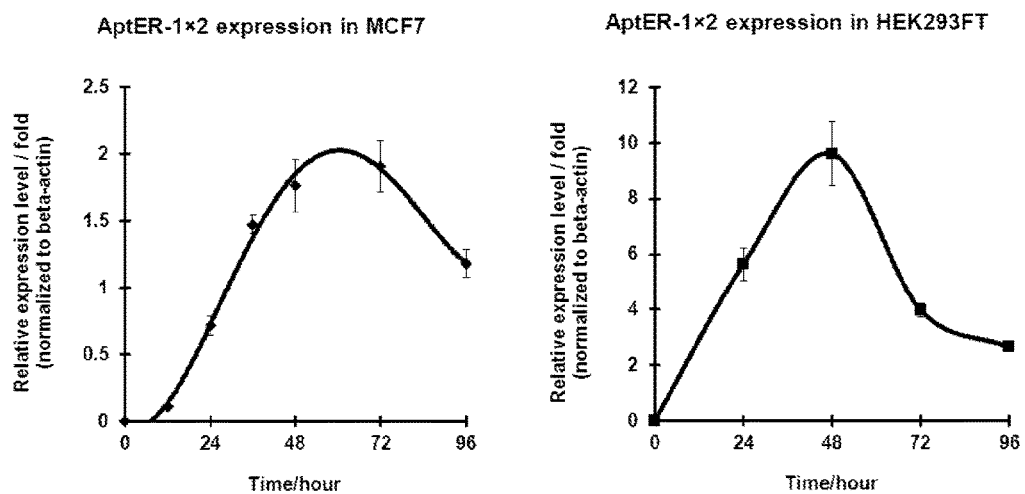
FIG. 16 illustrates the expression pattern of AptER-1×2 in mammalian cells from pSUPER vector. pSUPER/AptER-1×2 plasmid DNA was transiently transfected into MCF7 (left panel) and HEK293FT (right panel). Cells were harvested at several time points within 96 hours post-transfection. The level of AptER-1×2 was quantified using real time RT-PCR and expressed as relative expression level (fold) of beta-actin.

The relative level of aptamer in MCF7 (FIG. 16, left panel) examined over a period of 96 hours peaked between 48 h to 72 h post-transfection, whereas it formed a peak at 48 h post-transfection in HEK293FT (FIG. 16, right panel). The difference in time for aptamer accumulation to peak in the two cell lines may be explained by higher proliferation rate in HEK293FT than MCF7. As the cell divides faster, the expression vectors were diluted faster in HEK293FT in comparison to MCF7. Furthermore, the relative level of aptamer at the peak in HEK293FT was 4.5-fold higher than MCF7, although whether the beta-actin level in the two cell lines are similar remains unknown. Regardless of these differences, the accumulation pattern indicates the best time to test the effects of expressed aptamers was around 48 to 72 h post-transfection.

To test the effects of these constructs on hERα activity in vivo, a luciferase transcription system regulated by hERα was prepared to assess whether the aptamers will inhibit hERα-dependent transcription activation. A dual-luciferase assay was carried out with MCF7 cells to test the effects of RNA aptamers on transcription activation mediated by hERα, as described in the Materials and Methods. Two luciferase reporter vectors and an aptamer or control RNA expression vector were co-transfected into the cells. A firefly luciferase reporter vector 3×ERE TATA luc carries three copies of Xenopus Vitellogenin A2 ERE in the luciferase promoter region, which allows the transcriptional regulation by the endogenous hERα. The amount of firefly luciferase enzyme assayed is proportional to the activity of the receptor, whereas Renilla luciferase constitutively expressed from the other reporter vector served as an internal control to normalize transfection efficiency among different transfection reactions. Both luciferase levels were measured in one dual-luciferase assay sequentially using Dual-Luciferase Reporter Assay kit (Promega). The ratio of firefly luciferase activity to Renilla luciferase activity was determined, and the value in the control was considered to be 100%, which represents full transcriptional activation. The ratios of firefly luciferase activity to Renilla luciferase activity in all aptamer-expressing samples were then normalized against that of the control and expressed as normalized firefly luciferase activity (%) of the control. Whether the expressed aptamers affect ERα functions was determined by comparing the normalized firefly luciferase activity of aptamer-expressing samples with that of the control RNA-expression sample.

Figure 17:
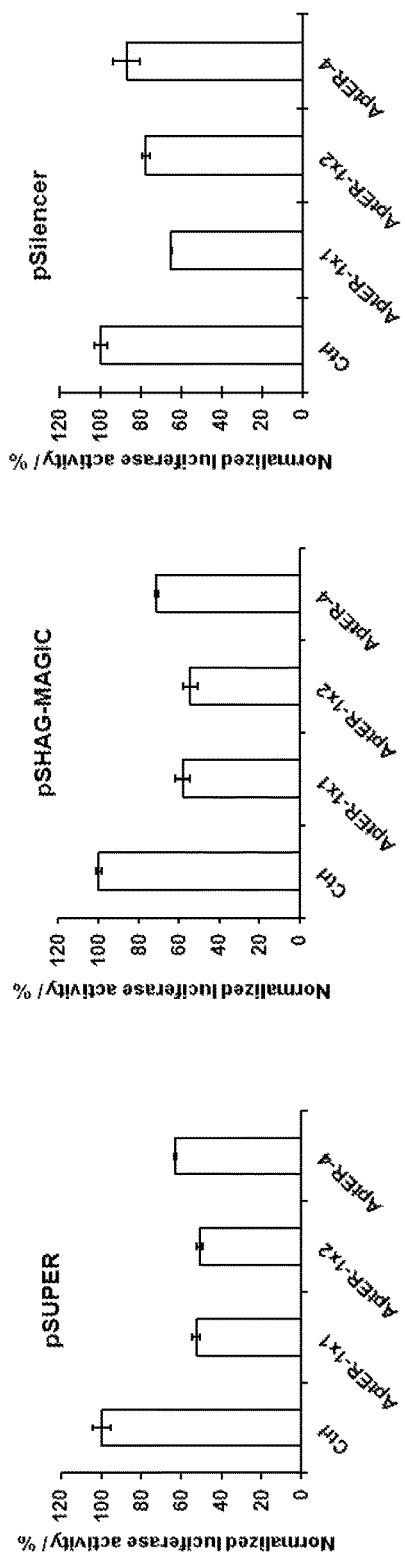
FIG. 17 is an image of a Dual-luciferase assay showing that the expressed aptamers inhibit hERα-dependent transcriptional activation in MCF7 cells. MCF7 cells were transfected with firefly luciferase vector (3×ERE TATA luc), Renilla luciferase vector and aptamer expression vetors. In the control, a scramble RNA expression vector was used in the place of the aptamer expression vectors. Seventy-two hours post-transfection, both luciferase levels were measured in one dual-luciferase assay sequentially using Dual-Luciferase Reporter Assay kit (Promega). The ratio of firefly luciferase activity to Renilla luciferase activity was determined, and the value was normalized against that of the control and expressed as normalized firefly activity (%) of the control. All experiments were carried out in triplicates and the average of used to plot the figures.

Expression of the three aptamers from pSHAG-MAGIC and pSUPER resulted in 30-50% reduction in endogenous hERα-mediated firefly luciferase activity (FIG. 17). Notably, among the three aptamer constructs, AptER-1×2 was the most competent inhibitor of transcriptional activation, followed by the AptER-1×1 and then AptER-4. This ranking of efficacy agreed well with their relative binding affinities to the recombinant ERα in vitro, which demonstrated the specificity of the inhibition. It also indicated that expressed aptamers probably inhibited transcriptional activation mediated by hERα through specific binding, and thus abolished certain interaction between hERα and its target DNA or coactivators. The magnitude of inhibition by an aptamer expressed from a pSUPER vector was slightly better than its counterpart expressed from a pSHAG-MAGIC vector. Whether it was caused by a higher expression level of aptamer driven by a HI promoter in the pSUPER vector in comparison to a U6 promoter in the pSHAG-MAGIC vector or other factors remains undetermined.

Expression of the three aptamers from pSilencer resulted in 20-40% reduction in endogenous hERα-mediated firefly luciferase activity (FIG. 17). However, AptER-1×1 is more competent than AptER-1×2, which neither agreed with their relative affinity to hERα nor followed the pattern observed with the aptamers expressed from the other two vectors.

As a whole, it was indicated that the set of pSUPER aptamer expression vectors was the best among the three sets of vectors, and thus it was chosen for future functional assays.

Example 8—Validation of Aptamer-hERα Interaction In Vivo by RNA Pull-Down Assay and Co-Immunoprecipitation Assay The intracellular interaction between ERα and expressed aptamers was validated using an RNA-coimmunoprecipitation assay and a pull-down assay. As the binding sites of aptamers on ER are undetermined, a tag coupled to hERα was used as an epitope instead of hERα itself to avoid antibodies interfering with aptamer-hERα interactions. An N-terminus SNAP-tag hERα was constructed for this purpose. The SNAP-tag is a 20 kDa protein based on a human DNA repair protein, $O^6$-alkylguanine-DNA-alkyltransferase (hAGT). The SNAP-tag recognizes a benzylguanine group on the SNAP substrates, such as SNAP-Cell TMR Star and SNAP-Capture Pull down Resin, and forms a covalent bond with the benzyl group. The dyes or beads in the substrates coupled to the benzyl group are then attached to the SNAP-tag. Anti-SNAP polyclonal antibody is also available for immunoprecipitation of SNAP-tag proteins. Thus, SNAP-hERα can be labeled in situ with fluorescent dyes, pulled down from cell lysate using benzylguanine conjugated resins, or immunoprecipitated using the anti-SNAP antibody.

HeLa cells were chosen for two reasons: first, ERα was absent in this cell line, and thus only SNAP-hERα captured expressed AptER-1×2 inside the cells; second, the unique high-spreading cell morphology of HeLa allows excellent fluorescent microscopic detection of SNAP-hERα expression. Human ERα coding gene was inserted into pSNAP-tag (m) vector between the Sbf I and Xho I sites downstream of the SNAP coding sequence. The expression vector was introduced into HeLa cells by transient transfection using FuGENE6 as described in the Materials and Methods.

The expression of the recombinant SNAP-hERα was confirmed by both fluorescent microscopy and western blotting. 24 h post-transfection, live cells were labeled with SNAP-Cell TMR-Star (New England Biolabs) and Hoechst 33342 (Invitrogen). During the labeling reaction, SNAP recognized a benzylguanine group in the SNAP-Cell TMR Star and formed a covalent bond with a fluorophore-coupled benzyl group, permitting the visualization of the fusion protein in living or fixed cells. As shown in FIG. 18A, the SNAP fusion protein was shown to localized in both cytoplasm and nucleus, but mainly in the nucleus. This distribution pattern agreed with the described mechanism of action of ER. To examine whether the fusion protein was of correct size, a western blotting was performed. Twenty-four hours post-transfection, cells were harvested in SDS loading buffer. Samples were prepared and analyzed as described in the Materials and Methods. Rabbit anti-SNAP polyclonal antibody was used to detect SNAP fusion protein. As shown in FIG. 18B, in vector transfected cells, a SNAP-tagged protein of around 80 kDa was expressed, while the protein was absent in non-transfected cells. The calculated molecular weight of SNAP-hERα is 86 kDa, so the protein band should be SNAP-hERα.

To verify the intracellular interaction between expressed RNA aptamers and SNAP-hERα in the HeLa cells, a pull-down assay and an RNA co-immunoprecipitation (RNA co-IP) assay were performed, followed by quantification of the RNA aptamer. The pull-down assay and RNA co-immunoprecipitation assay were done in parallel using the same batch of cell samples. The SNAP-hERα and the aptamer (AptER-1×2) were co-expressed in HeLa cells, and the SNAP-hERα was pulled down or immunoprecipitated from the cell lysate. The RNA aptamers in association with the SNAP-hERα was quantified using RT-PCR. As a control, the SNAP-tag itself was used in the place of the SNAP-hERα in the co-transfection of a second dish of HeLa cells, RNA in association with the SNAP-tag was used to cancel out the background of nonspecific interaction between the SNAP-tag and the RNA aptamer.

HeLa cells were co-transfected with SNAP-hERα expression vector and pSUPEP/AptER-1×2 expression vector. AptER-1×2 was chosen as a representative because of its best performance among the three aptamer constructs. A SNAP expression vector replaced SNAP-hERα in the control. 48 h post-transfection, transfected cells were treated with formaldehyde as described in the Materials and Methods section, thus the aptamer-ER complex was crosslinked inside the cells. Comparable expression levels of the SNAP and SNAP-hERα was confirmed by Western blot (FIG. 18C, middle panel). Cells were lyzed by sonication, and the soluble cell lysate was aliquoted and incubated with two kinds of beads. The one used for a pull-down assay carried a benzylguanine group that can be recognized by the SNAP-tag, and a covalent bond between the benzyl group on the beads and the SNAP-tag fusion protein was formed. The other beads used for RNA co-IP was protein-G beads coated with rabbit anti-SNAP polyclonal primary antibody. Two sets of buffers of different stringency were employed. Considering the forces of bonding formed between the SNAP-tag and the beads, the more stringent one was used in the pull-down assay. RNA recovered from the beads was quantified with real time RT-PCR. As shown in FIG. 18C, SNAP-hERα pull-downed 292-fold more aptamers than the SNAP control; SNAP-hERα immunoprecipitated 67-fold more aptamer than the SNAP tag. These results demonstrated that hERα and AptER-1×2 interacted specifically inside HeLa cells. The difference in folds of change (SNAP-hERα vs. SNAP) from these two assays might be caused by the higher stringency of buffers used in the pull-down assay, resulting in less nonspecific interaction in the SNAP control.

Discussion of Examples 1-8

Although the precise domain to which Class I and Class II aptamers was not defined, indicating that the two classes of aptamers may bind to distinct surfaces on hERα other than the DBD and the LBD, the preceding Examples demonstrate the ability to express versions of these aptamer classes in mammalian cells and disrupt hERα activity. One advantage of the pSUPER vector employed is that it can be transfected into retrovirus packing cell line Phoenix™ Ampho Cells (Orbigen) to generate retrovirus capable of infecting cells for long-term, continuous aptamer expression. Similarly, if adenoviral infection-mediated delivery of aptamer expression constructs is desired, the aptamer coding gene including the U6 promoter from the pSHAG-MAGIC can be transferred to adenoviral vector pAd/BLOCK-iT-DEST (Invitrogen) using Gateway technology (Invitrogen). High-titer adenoviruses can be generated in the packing cell line HEK293A, and used to infect cell lines of interest.

If the inhibiting effects of aptamers on hERα are comparable to E2-deprival, then these aptamers should be available at a fairly high amount for several days. Even at the peak (72 h post-transfection), aptamers inhibited hERα-mediated transactivation by up to 50%. Further enhancement in aptamer expression should be available by using RNA polymerase II promoters and transgenes encoding a multimeric construct containing cis-acting ribozymes to afford multiple functional aptamer constructs per transcriptional event. If the expression of such aptamers is driven by such a promoter, and the whole cassette is transferred into a retroviral or lentiviral vector to make viruses for infection, then stable cell lines for inducible aptamer expression may be generated.

Example 9—Identification of Additional Class I Aptamers

To study the evolutionary dynamics of RNA sequences in the SELEX pools of Example 1, a few pools, namely ERL0, ERL3, ERL5 and FLER5 (as shown in FIG. 4B) were sequenced using next generation illumina sequencing. The top ten sequences among these pools were tested for binding to ERα. Among them four new RNA aptamers were identified in the pool ERL5. The sequences of the new aptamers, namely ERL5-1, 4, 5 and 6 are shown above of SEQ ID NOS: 15-18, respectively. 22 residues at the 5' and 3' ends constitute conserved regions, with the variable regions positioned in between. Their binding behavior indicates that they belong to class I as defined in preceding Examples.

Figure 19:
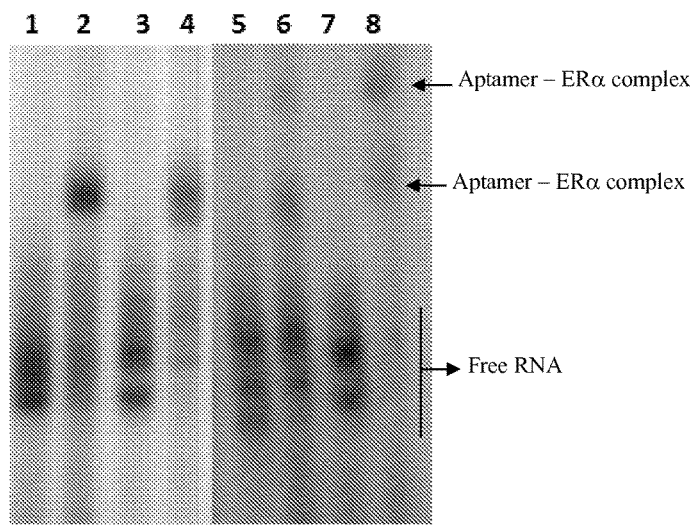
FIG. 19 illustrates an electrophoretic mobility shift assay showing aptamer-ERα interaction. Lanes 1, 2 have labeled aptamer ERL5-1 (SEQ ID NO: 15); lanes 3, 4 have ERL-4 (SEQ ID NO: 16); lanes 5, 6 have ERL5-5 (SEQ ID NO: 17) while lanes 7, 8 have ERL5-6 (SEQ ID NO: 18). Lanes 1, 3, 5 and 7 contain labeled RNA aptamer alone, while lanes 2, 4, 6 and 8 have labeled aptamer and 200 nM ERα. All the lanes had 1 mM BSA and 1 µg yeast RNA as non-specific competitors. Gel used to separate RNA protein complex was PAGE (6%-acrylamide:bisacrylamide is 37.5:1) run in 0.5× Tris-borate-EDTA buffer.

As shown in FIG. 19, these new sequences bind to ERα (200 nM) in the electrophoretic mobility shift assay (EMSA) studies. ERL5-1 (SEQ ID NO: 15) showed one RNA protein complex, while ERL5-4, 5 and 6 (SEQ ID NOS: 16-18, respectively) showed two shifted bands.

Example 10—Augmenting Expression Levels of RNA Aptamer by Using a Pol II-Driven System A critical factor in the design of the expression system is the rapid production of saturating amounts of high affinity aptamers. Intracellular expression of aptamer from a RNA pol III promoter-driven expression construct delivered by transient transfection can achieve transcriptional inhibition by 50% in dual-luciferase assay. However, the degree of inhibition was not high enough to affect hERα-dependent cell proliferation. To achieve a higher expression level, a stronger promoter (e.g., RNA pol II) along with the design and construction of a polyvalent aptamer encoded by polymeric aptamer coding regions in a RNA transcript will be used (see FIG. 20). Previous work by Shi et al. demonstrated that high levels of aptamers (10% of mRNA) can be produced with half-life reaching 6 hours, when a single dodecamer of an aptamer pentamer is transcribed from a strong inducible promoter (see Shi et al., "A Specific RNA Hairpin Loop Structure Binds the RNA Recognition Motifs of the *Drosophila* SR Protein B52," *Mol Cell Biol* 17(5): 2649-2657 (1997); U.S. Pat. No. 6,458,559 to Shi et al., which is hereby incorporated by reference in its entirety).

As full inhibition of hERα functions is lethal to hERα-dependent breast cancer cell lines, it is desirable to express AptER-1×2 in an inducible manner. For this purpose, the aptamer gene can be placed under the control of the RNA pol II driven promoter of human cytomegalovirus immediate early (CMV IE) gene, which can be made regulatable over several orders of magnitude by tetracycline (Yao et al., "Tetracycline Repressor, tetR, Rather than the tetR-Mammalian Cell Transcription Factor Fusion Derivatives, Regulates Inducible Gene Expression in Mammalian Cells," *Hum Gene Ther* 9(13): 1939-1950 (1998), which is hereby incorporated by reference in its entirety). Commercial vectors implementing this system are available (e.g. Gateway® pT-Rex™-DEST30 Vector from Invitrogen).

Figure 20:
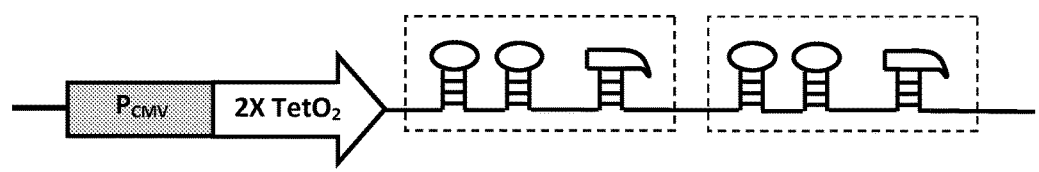
FIG. 20 illustrates a transgene expressing dimeric divalent hERα RNA aptamers. The transcriptional template contains two dimeric units driven by a tetracycline-inducible RNA pol II promoter (CMV). Each dimeric unit is indicated as a box with the RNA secondary structure of its transcript symbolically depicted. A cis-acting ribozyme allows for self-cleaving of the transcript into functional aptamer dimers.

Unlike RNA pol III, whose transcripts are limited to 400 nucleotides or less in length, RNA pol II can produce much longer transcripts, which will allow for the expression of polymeric aptamer coding regions to increase ER aptamer production and accumulation. The long transcript is encoded by a polymeric synthetic gene consisting of repetitive head-to-tail aptamer coding units (FIG. 20). A cis-acting hammerhead ribozyme can be introduced on either side of the aptamer coding unit, and upon transcription of the polymeric aptamer RNA, the hammerhead ribozymes undergo self-cleavage, which results in the release of multiple free functional aptamers. This self-cleavage of ribozymes will ensure that the aptamer RNAs neither lose their activity due to flanking sequences, nor are polyadenylated for nuclear export and thus remain localized within the nucleus. Furthermore, the released form has its 5' and 3' ends in a stem, which is thought to stabilize and protect the RNA aptamer from degradation (Shi et al., "RNA Aptamers as Effective Protein Antagonists in a Multicellular Organism," *Proc Natl Acad Sci USA* 96(18): 10033-10038 (1999), which is hereby incorporated by reference in its entirety). Thus, the expression system will allow high expression level of stable aptamer RNAs from every transcription cycle. Aptamer dosage can be controlled through the length of the block polymer.

This strategy will be implemented using the previously constructed divalent AptER-1 (i.e., AptER-1×2) and a stepwise polymerization strategy to make an octomeric AptER-1×2 gene. This will be achieved by subcloning a single AptER-1×2 coding unit upstream of a hammerhead ribozyme coding unit. The AptER-1×2 coding unit (AptER-1×2-hammerhead ribozyme), flanked by Xho I and Sal I restriction sites at the 5' and 3' ends, respectively, will be lifted using a pair of primers containing the attB Gateway cloning sequences (Invitrogen) and restriction sites, and sub-cloned to a Gateway donor vector (such as pDONR™221). As each AptER-1×2 unit will be flanked by the complementary asymmetric Xho I and Sal I sites, the general Gateway cloning strategy can be used to select for correctly ligated tandem AptER-1×2 repeats. In this method, a single AptER-1×2 unit will be lifted from pDONR221 using the pair of primers described above, subjected to either Sal I or Xho I restriction, and then the two digestion products will be combined and ligated. Among the three possible types of ligation products, only the one in proper head-to-tail orientation contains the required Gateway AttB sites in the 5' and 3' ends (AttB1.AptER-1×2 unit, AttB2) needed for creation of a Gateway compatible expression vector. Using the polymer of two as a template and repeating the polymerization strategy creates a polymer of four. Overall, geometric progression of polymeric length will be achieved in each subsequent round of polymerization. An LR recombination reaction between the resulting entry clone and a destination vector (pT-Rex™-DEST30) will be performed to generate a mammalian cell expression vector (pT-Rex™-DEST30/Aptamer).

This multimeric AptER-1×2 construct will be used to transform a mammalian cell line of interest (e.g., several ER-positive breast cancer cell lines), followed by a drug selection to obtain transfected cells. Clones that express the highest levels of Tet repressor will be the best host strains, as they should exhibit the most complete repression of basal transcription of aptamer expression. To establish a stable cell line that constitutively expresses the Tet repressor and inducibly expresses aptamers, a stable TetR-expressing cell line will be transfected with linearized pT-Rex™-DEST30/Aptamer plasmids and then screened for stable transfectants using Geneticin-containing media. Control over aptamer expression will be examined by evaluating the level of aptamer in total RNA from growing foci using real time PCR. Clones that exhibit the lowest levels of basal transcription and the highest levels of aptamer expression upon tetracycline addition will be maintained and used to examine the effects of aptamer on cellular and molecular phenotypes related to tumorigenesis. Xenograft studies will be performed to assess tumorigenesis in animals in the absence and presence of aptamer-induced inhibition of estrogen receptor activity in the breast cancer cells.

Example 11—Construction and Use of Aptamer Conjugate for Targeting Delivery to Cancer Cells An aptamer conjugate will be prepared using a 3' biotinylated HER-2 specific 2'-fluoro-RNA aptamer of SEQ ID NO: 20 (Kim et al., "In vitro Selection of RNA Aptamer and Specific Targeting of ErbB2 in Breast Cancer Cells," Nucleic Acid Ther 21(3): 173-178 (2011), which is hereby incorporated by reference in its entirety) and a 3' biotinylated aptamer AptER-1×2(138nt) (SEQ ID NO: 9). The AptER-1×2(138nt) may optionally be formed using modified nucleotides (e.g., 2'-fluoro RNA) to enhance the aptamer half life. Biotinylation of these aptamers at their 3' ends is known not to interfere with the activity of RNA aptamers (see Chu et al., "Aptamer Mediated siRNA Delivery," Nucl Acids Res. 34(10):e73 (2006), which is hereby incorporated by reference in its entirety).

The aptamers will be synthesized by in vitro transcription from a double-stranded DNA template bearing a T7 RNA polymerase promoter. The aptamers will be purified using polyacrylamide gel electrophoresis, followed by overnight elution in water and ethanol precipitation.

Biotinylation of the purified aptamers will we carried out using the procedures of Chu et al., "Aptamer Mediated siRNA Delivery," Nucl Acids Res. 34(10):e73 (2006), which is hereby incorporated by reference in its entirety. Briefly, purified aptamer (150 nM) will be oxidized in 100 mM NaOAc (pH 5.0), 100 mM NaIO$_4$ (90 min, RT, dark), and the oxidized aptamers will be recovered via ethanol precipitation. The oxidized RNA will be reacted with 200 pmol of freshly prepared biotin-hydrazide in 500 μL 100 mM NaOAc (pH 5.0) (3 h, RT), and the hydrazide removed. The biotinylated RNA will be gel-purified.

Using 100 mM KOAc, 30 mM HEPES-KOH (pH 7.4) and 2 mM MgOAc buffer, 200 pmol of each biotinylated aptamer (1:1 ratio) will be introduced with 100 pmol of streptavidin. The complex will be allowed to equilibrate for a minimum of 10 min and then be stored on ice until its use.

ERa-aptamer:streptavidin:HER2-aptamer conjugates will be added directly to cell culture media (500 μl) at a final concentration of either 10 nM, 50 nM, or 100 nM conjugate. HER-2 positive breast cancer cell lines MDA-MB-361 and BT-474, and ovarian carcinoma cell line SKOV-3 will be introduced at cell densities of $10^4$-$10^6$, and cells will be assessed at 24, 48, and 72 h after the addition of the conjugate for cell survival.

With positive in vitro results, these same cell lines and conjugates will be used in a xenograft model of breast cancer and ovarian cancer. Athymic nude mice bearing intraperitoneal SKOV-3 human ovarian cancer xenografts or MDA-MB-361 breast cancer carcinoma xenografts grown in the mammary fat pad will be used. Seven days following implantation animals in several test groups will be administered 1 mg/kg or 10 mg/kg of the conjugate via i.p. injection every three days. Animals will be maintained for 20 weeks following start of treatment. Tumor weights will be assessed every three days beginning the day treatment is started. Assessment of treatment versus control will be measured by percent test/control (% T/C) tumor weights calculated on each day that tumors are measured, tumor growth delay, and/or tumor regression.

Example 12—Construction and Use of Conjugate for Targeting Expression Vector Delivery to Cancer Cells The plasmid vector prepared in accordance with Example 10 will be used to prepare a polycation conjugated vector. This will be carried out using the procedure of Moffatt et al., "Successful in vivo Tumor Targeting of Prostate-specific Membrane Antigen with a Highly Efficient J591/PEI/DNA Molecular Conjugate,"Gene Therapy 13:761-772 (2006), which is hereby incorporated by reference in its entirety, except that the plasmid vector from Example 10 will replace the β-gal plasmid of Moffatt and the prostate-specific mAb J591 will be replaced by Trastuzumab, a HER2-specific mAb.

The addition of polyethylene glycol (PEG) (Sigma, Mr=3000) as a spacer between phenyl(di)boronic acid (PDBA) and Trastuzumab will be carried out in a stepwise manner by first generating PDBA-PEG. About 300 mg of ω-amino-α-carboxyl PEG will be suspended in 0.1 M NaHCO$_3$ to a final concentration of 2 mg/ml. A 10 mM stock of PDBA-x-N-hydroxysuccinimide (NHS) will be made in N,N-dimethylformyl amine. A molar ratio of 5:1 of PDBA to PEG will be produced by adding 4.4 ml of PDBA-x-NHS solution to the PEG solution. The sample will be dialyzed using a 1000-Mw membrane for 48 h at 41 C against 20 mM HEPES buffer in the cold to yield PDBA-PEG. For PDBA-PEG-Trastuzumab formation, Trastuzumab will be warmed in 37 C for 5 min to activate the antibody, and then 300 mg of the antibody will be reacted with 0.1 M NaHCO$_3$ in a final volume of 250 ml. Following this, 1.3 ml of 0.1 M DTT solution will be added for 10 min in a 37 C water bath to reduce disulfide bond formation. The DTT will be removed with Ultrafree-MC filter unit. In all, 300 mg of the 5:1 PDBA:PEG ratio will be introduced in a solution of 0.1M 2-[N-morpholino]ethane-sulfonic acid, pH 6.0, and 0.5 M NaCl, and the final volume will be brought up to 300 ml with distilled water. To activate the PEG for coupling to Trastuzumab, 1-ethyl-3-(3-dimethyl-aminopropyl) carbodiimide and NHS will be added to final concentrations of 2 and 5 mM, respectively, allowed to react at room temperature for 15 min, and the reaction terminated with β-mercaptoethanol at a final concentration of 20 mM. Finally, 150 mg of Trastuzumab solution (1 mg/ml) will be combined with the PDBA-PEG solution and allowed to proceed for 2 h at room temperature, after which dialysis will be performed for 48 h with 6000-8000 Mw cutoff membrane.

A working solution of 10 mM salicylhydroxamic acid-polyethylenimine (SHA-PEI) (pH 7.4) will be prepared in endotoxin-free water (BioWhittaker) and stored at 41 C. 4.5 ml of SHA-PEI will be added to 5.5 ml of 20 mM HEPES buffer, and then plasmid (6 mg) will be pipetted into polystyrene tubes and the solution brought up to 60 ml with HEPES buffer. Following this, 10 ml of the SHA-PEI solution will be added directly to the plasmid DNA solution and the solution allowed to incubate at room temperature for 5 min. After this, appropriate amounts of PDBA-PEG-Trastuzumab will be added and the incubation continued for an additional 5 min, which will result in the formation of the Trastuzumab/PEG/PEI/DNA(ER-aptamer) vector.

This conjugate will be screened in vitro using the cell lines described in the Example 11, and also screened for in vivo activity using the xenograft mouse models described in Example 11. Tetracycline will be administered to induce expression of the aptamer construct.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. All of the features described herein (including any accompanying claims, abstract and drawings), and/or all of the steps of any method or process so disclosed, may be combined with any of the above aspects in any combination, except combinations where at least some of such features and/or steps are mutually exclusive. Additionally, the recited order of processing elements or sequences, or the use of numbers, letters, or other designations therefore, is not intended to limit the claimed processes to any order except as may be specified in the claims. These alterations, improvements, and modifications are intended to be suggested hereby, and are within the spirit and scope of the invention. Accordingly, the invention is limited only by the following claims and equivalents thereto.

---

What is claimed:

1. A nucleic acid aptamer molecule comprising a domain that binds to an estrogen receptor, wherein the nucleic acid aptamer molecule comprises a nucleotide sequence according to one of SEQ ID NOS: 1-4, 11, 12, 15-18, or minimal effective ER-binding fragments thereof.

2. The nucleic acid aptamer molecule according to claim 1, wherein the nucleic acid aptamer molecule comprises a nucleotide sequence according to SEQ ID NO: 1, SEQ ID NO: 11, SEQ ID NO: 12, or minimal effective ER-binding fragments thereof.

3. The nucleic acid aptamer molecule according to claim 1, wherein the nucleic acid aptamer molecule comprises a nucleotide sequence according to one of SEQ ID NOS: 15-18, or minimal effective ER-binding fragments thereof.

4. A molecular complex comprising the nucleic acid aptamer molecule according to claim 1 and an estrogen receptor.

5. A constructed DNA molecule comprising a first region encoding a nucleic acid aptamer molecule according to claim 1, wherein the nucleic acid aptamer molecule comprises RNA.

6. An expression system comprising an expression vector into which is inserted a DNA molecule according to claim 5.

7. An isolated host cell containing the expression system of claim 6.

8. A method of inhibiting estrogen receptor activity in a cell, the method comprising:
   contacting an estrogen receptor in a cell with a nucleic acid aptamer molecule according to claim 1, whereby said nucleic acid aptamer molecule binds to said estrogen receptor and inhibits activity thereof.

9. The method according to claim 8, where the estrogen receptor activity comprises nuclear signaling or transcriptional activation.

10. The method according to claim 9, wherein the transcriptional activation level of the estrogen receptor is reduced by about 30 to about 50 percent in the cell.

11. The method according to claim 8, wherein said contacting is carried out with an agent comprising the nucleic acid aptamer molecule, whereby the agent is taken up by the cell and the nucleic acid aptamer molecule is released internally into the cell.

12. The method according to claim 11, wherein the agent comprises a cationic polymer, modified cationic polymer, peptide molecular transporter, lipid, liposome, non-cationic polymer, or a second nucleic acid aptamer molecule that binds specifically to a cancer cell surface receptor, which second nucleic acid aptamer is covalently or non-covalently linked to the nucleic acid aptamer molecule that binds to the hER.

13. The method according to claim 8, further comprising:
   introducing an expression system encoding the nucleic acid aptamer molecule into the cell; and expressing the nucleic acid aptamer molecule in the cell.

14. The method according to claim 8, wherein the cell is a breast cancer cell, ovarian cancer cell, uterine cancer cell, or endometrial cancer.

15. A method of treating a patient for an estrogen dependent cancer comprising:
   administering to the patient an agent comprising or encoding a nucleic acid aptamer molecule according to claim 1, whereby the agent is taken up by an estrogen dependent-cancer cell and the nucleic acid aptamer molecule inhibits activity of the estrogen receptor in the cancer cell and thereby inhibits cancer cell growth.

* * * * *

SEQUENCE LISTING

```
<160> NUMBER OF SEQ ID NOS: 74

<210> SEQ ID NO 1
<211> LENGTH: 100
<212> TYPE: RNA
<213> ORGANISM: Artificial
<220> FEATURE:
<223> OTHER INFORMATION: Aptamer AptER-1

<400> SEQUENCE: 1
gggagaauuc aacugccauc uaggcccaca guucagaggc accgcgaaca aaacgcaaga        60
cagagugccg acaagagcac uacaagcuuc uggacucggu                            100

<210> SEQ ID NO 2
<211> LENGTH: 98
<212> TYPE: RNA
<213> ORGANISM: Artificial
<220> FEATURE:
<223> OTHER INFORMATION: Aptamer AptER-2

<400> SEQUENCE: 2
gggagaauuc aacugccauc uaggcacacg cgagauagag cgaggccucc aaaaauggcc        60
acgccaggaa gcaaguacua caagcuucug gacucggu                               98

<210> SEQ ID NO 3
<211> LENGTH: 101
<212> TYPE: RNA
<213> ORGANISM: Artificial
<220> FEATURE:
<223> OTHER INFORMATION: Aptamer AptER-3

<400> SEQUENCE: 3
gggagaauuc aacugccauc uaggcgaccc agggccggga cgcaaagcag ccaaaacaga        60 cggcccagu cagggaguua cuacaagcuu cuggacucgg u                           101

<210> SEQ ID NO 4
<211> LENGTH: 100
<212> TYPE: RNA
<213> ORGANISM: Artificial
<220> FEATURE:
<223> OTHER INFORMATION: Aptamer AptER-4
```

```
<400> SEQUENCE: 4
gggagaauuc aacugccauc uaggccacag ccggcggucg aacaccagag ggcgacuuug    60
gguagucgag uauuaaguac uacaagcuuc uggacucggu                         100

<210> SEQ ID NO 5
<211> LENGTH: 65
<212> TYPE: RNA
<213> ORGANISM: Artificial
<220> FEATURE:
<223> OTHER INFORMATION: Aptamer AptER-1(65nt)

<400> SEQUENCE: 5
gggcagaggc accgcgaaca aaacgcaaga cagagugccg acaagagcac uacaagcuuc    60
ugccc                                                                65

<210> SEQ ID NO 6
<211> LENGTH: 53
<212> TYPE: RNA
<213> ORGANISM: Artificial
<220> FEATURE:
<223> OTHER INFORMATION: Aptamer AptER-1(53nt)

<400> SEQUENCE: 6
gggcaccgcg aacaaaacgc aagacagagu gccgacaaga gcacuacaag ccc           53

<210> SEQ ID NO 7
<211> LENGTH: 138
<212> TYPE: RNA
<213> ORGANISM: Artificial
<220> FEATURE:
<223> OTHER INFORMATION: Aptamer AptER-1x2(138nt)

<400> SEQUENCE: 7
ggauccguga cgggcaccgc gaacaaaacg caagacagag ugccgacaag agcacuacaa    60
gcccguccau acuccggcac cgcgaacaaa acgcaagaca gagugccgac aagagcacua   120
acagccggag gcggaucc                                                 138

<210> SEQ ID NO 8
<211> LENGTH: 61
<212> TYPE: RNA
<213> ORGANISM: Artificial
<220> FEATURE:
<223> OTHER INFORMATION: Aptamer AptER-1x1

<400> SEQUENCE: 8
gagaggcacc gcgaacaaaa cgcaagacag agugccgaca agagcacuac aagccucucu    60
u                                                                    61

<210> SEQ ID NO 9
<211> LENGTH: 132
<212> TYPE: RNA
<213> ORGANISM: Artificial
<220> FEATURE:
<223> OTHER INFORMATION: Aptamer AptER-1x2

<400> SEQUENCE: 9
gcgugacggg caccgcgaac aaaacgcaag acagagugcc gacaagagca cuacaagccc    60
guccauacuc cggcaccgcg aacaaaacgc aagacagagu gccgacaaga gcacuaacag   120
ccggaggcgc uu                                                       132
```

```
<210> SEQ ID NO 10
<211> LENGTH: 97
<212> TYPE: RNA
<213> ORGANISM: Artificial
<220> FEATURE:
<223> OTHER INFORMATION: Aptamer AptER-4

<400> SEQUENCE: 10
gagaauucaa cugccaucua ggccacagcc ggcggucgaa caccagaggg cgacuuuggg      60
uagucgagua uuaaguacua caagcuucug gacucuu                              97

<210> SEQ ID NO 11
<211> LENGTH: 100
<212> TYPE: RNA
<213> ORGANISM: Artificial
<220> FEATURE:
<223> OTHER INFORMATION: Aptamer Clone B30

<400> SEQUENCE: 11
gggagaauuc aacugccauc uaggcccaca guucagaggc accgcgaaca caacgcaaga      60
cagagugacg acaagagcac uacaagcuuc uggacucggu                           100

<210> SEQ ID NO 12
<211> LENGTH: 100
<212> TYPE: RNA
<213> ORGANISM: Artificial
<220> FEATURE:
<223> OTHER INFORMATION: Apatmer Clone B65

<400> SEQUENCE: 12
gggagaauuc aacugccauc uaggcccaca guucagaagc accgcgaaca aaacgcaaga      60
cagagugccg acaagagcac uacaagcuuc uggacucgga                           100

<210> SEQ ID NO 13
<211> LENGTH: 65
<212> TYPE: RNA
<213> ORGANISM: Artificial
<220> FEATURE:
<223> OTHER INFORMATION: Apatmer Clone sB30

<400> SEQUENCE: 13
gggcagaggc accgcgaaca caacgcaaga cagagugacg acaagagcac uacaagcuuc      60
ugccc                                                                 65

<210> SEQ ID NO 14
<211> LENGTH: 65
<212> TYPE: RNA
<213> ORGANISM: Artificial
<220> FEATURE:
<223> OTHER INFORMATION: Apatmer Clone sB65

<400> SEQUENCE: 14
gggcagaagc accgcgaaca aaacgcaaga cagagugccg acaagagcac uacaagcuuc      60
ugccc                                                                 65

<210> SEQ ID NO 15
<211> LENGTH: 93
<212> TYPE: RNA
<213> ORGANISM: Artificial
<220> FEATURE:
<223> OTHER INFORMATION: ApatmerERL5-1

<400> SEQUENCE: 15
```

```
gggagaauuc aacugccauc uacaagccaa gcaagcgagc aaaaaacgcg agcauccgag      60
cuccaagacg uacuacaagc uucuggacuc ggu                                  93
```

<210> SEQ ID NO 16
<211> LENGTH: 94
<212> TYPE: RNA
<213> ORGANISM: Artificial
<220> FEATURE:
<223> OTHER INFORMATION: Aptamer ERL5-4

<400> SEQUENCE: 16

```
gggagaauuc aacugccauc uaacagccaa guaagcgaca acgacaauca augacgcgaa      60
caauccgaaa gaacuacaag cuucuggacu cggu                                 94
```

<210> SEQ ID NO 17
<211> LENGTH: 94
<212> TYPE: RNA
<213> ORGANISM: Artificial
<220> FEATURE:
<223> OTHER INFORMATION: Aptamer ERL5-5

<400> SEQUENCE: 17

```
gggagaauuc aacugccauc uacagaagga ccgcgagggu aaaaaccacg cacgacagag      60
uauaacaaaa caacuacaag cuucuggacu cggu                                 94
```

<210> SEQ ID NO 18
<211> LENGTH: 94
<212> TYPE: RNA
<213> ORGANISM: Artificial
<220> FEATURE:
<223> OTHER INFORMATION: Aptamer ERL5-6

<400> SEQUENCE: 18

```
gggagaauuc aacugccauc uaaaugaaag gacgcacacu acguguccua caaacacaga      60
aacaaaaacc gaacuacaag cuucuggacu cggu                                 94
```

<210> SEQ ID NO 19
<211> LENGTH: 100
<212> TYPE: RNA
<213> ORGANISM: Artificial
<220> FEATURE:
<223> OTHER INFORMATION: Aptamer A30

<400> SEQUENCE: 19

```
uaauacgacu cacuauaggg aauuccgcgu gugccagcga aaguugcgua uggguacauu      60
cgcaggcaca ugucaucugg gcgguccguu cgggauccuc                          100
```

<210> SEQ ID NO 20
<211> LENGTH: 34
<212> TYPE: RNA
<213> ORGANISM: Artificial
<220> FEATURE:
<223> OTHER INFORMATION: Aptamer to Her-2

<400> SEQUENCE: 20

```
agccgcgagg ggagggauag gguagggcgc ggcu                                 34
```

<210> SEQ ID NO 21
<211> LENGTH: 98
<212> TYPE: RNA
<213> ORGANISM: Artificial
<220> FEATURE:
<223> OTHER INFORMATION: Aptamer S6

-continued

<400> SEQUENCE: 21
gggagauacc agcuuauuca auuuggaugg ggagauccgu ugaguaagcg ggcgugucuc    60
ucugccgccu ugcuaugggg agauaguaag ugcaaucu                           98

<210> SEQ ID NO 22
<211> LENGTH: 78
<212> TYPE: RNA
<213> ORGANISM: Artificial
<220> FEATURE:
<223> OTHER INFORMATION: Aptamer aptTOV1

<400> SEQUENCE: 22
uccagaguga cgcagcagau cuguguagga ucgcagugua guggacauuu gauacgacug    60
gcucgacacg guggcuua                                                 78

<210> SEQ ID NO 23
<211> LENGTH: 36
<212> TYPE: DNA
<213> ORGANISM: Artificial
<220> FEATURE:
<223> OTHER INFORMATION: forward primer

<400> SEQUENCE: 23
ggcggacctg caggatgacc atgaccctcc acacca                             36

<210> SEQ ID NO 24
<211> LENGTH: 33
<212> TYPE: DNA
<213> ORGANISM: Artificial
<220> FEATURE:
<223> OTHER INFORMATION: reverse primer

<400> SEQUENCE: 24
ggcggactcg agtcagaccg tggcagggaa acc                                33

<210> SEQ ID NO 25
<211> LENGTH: 20
<212> TYPE: DNA
<213> ORGANISM: Artificial
<220> FEATURE:
<223> OTHER INFORMATION: marking oligo anti-FBS1

<400> SEQUENCE: 25
ggcctcacgc ctcctaactc                                               20

<210> SEQ ID NO 26
<211> LENGTH: 20
<212> TYPE: DNA
<213> ORGANISM: Artificial
<220> FEATURE:
<223> OTHER INFORMATION: marking oligo anti-FBS2

<400> SEQUENCE: 26
gaccggaggc gctaagtttc                                               20

<210> SEQ ID NO 27
<211> LENGTH: 40
<212> TYPE: DNA
<213> ORGANISM: Artificial
<220> FEATURE:
<223> OTHER INFORMATION: forward primer P40

<400> SEQUENCE: 27
gtaatacgac tcactatagg gagaattcaa ctgccatcta    40

<210> SEQ ID NO 28
<211> LENGTH: 22
<212> TYPE: DNA
<213> ORGANISM: Artificial
<220> FEATURE:
<223> OTHER INFORMATION: reverse primer P22

<400> SEQUENCE: 28
accgagtcca gaagcttgta gt    22

<210> SEQ ID NO 29
<211> LENGTH: 50
<212> TYPE: DNA
<213> ORGANISM: Artificial
<220> FEATURE:
<223> OTHER INFORMATION: estrogen response element probe

<400> SEQUENCE: 29
agtcaggtca cagtgacctg atcgaaagat caggtcactg tgacctgact    50

<210> SEQ ID NO 30
<211> LENGTH: 13
<212> TYPE: DNA
<213> ORGANISM: Xenopus laevis

<400> SEQUENCE: 30
ggtcacagtg acc    13

<210> SEQ ID NO 31
<211> LENGTH: 31
<212> TYPE: DNA
<213> ORGANISM: Artificial
<220> FEATURE:
<223> OTHER INFORMATION: forward primer for AptER-1-53nt

<400> SEQUENCE: 31
gtaatacgac tcactatagg gcaccgcgaa c    31

<210> SEQ ID NO 32
<211> LENGTH: 22
<212> TYPE: DNA
<213> ORGANISM: Artificial
<220> FEATURE:
<223> OTHER INFORMATION: reverse primer for AptER-1-53nt

<400> SEQUENCE: 32
gggcttgtag tgctcttgtc gg    22

<210> SEQ ID NO 33
<211> LENGTH: 37
<212> TYPE: DNA
<213> ORGANISM: Artificial
<220> FEATURE:
<223> OTHER INFORMATION: forward primer for AptEr-1-65nt

<400> SEQUENCE: 33
gtaatacgac tcactatagg gcagaggcac cgcgaac    37

<210> SEQ ID NO 34
<211> LENGTH: 19
<212> TYPE: DNA
<213> ORGANISM: Artificial
<220> FEATURE:
<223> OTHER INFORMATION: reverse primer for AptER-1-65nt

<400> SEQUENCE: 34
gggcagaagc ttgtagtgc                                         19

<210> SEQ ID NO 35
<211> LENGTH: 90
<212> TYPE: DNA
<213> ORGANISM: Artificial
<220> FEATURE:
<223> OTHER INFORMATION: forward primer for AptER-1x2(138nt)

<400> SEQUENCE: 35
gtaatacgac tcactatagg atccgtgacg ggcaccgcga acaaaacgca agacagagtg    60
ccgacaagag cactacaagc ccgtccatac                                    90

<210> SEQ ID NO 36
<211> LENGTH: 89
<212> TYPE: DNA
<213> ORGANISM: Artificial
<220> FEATURE:
<223> OTHER INFORMATION: reverse primer for AptER-1x2(138nt)

<400> SEQUENCE: 36
ggatccgcct ccggctgtag tgctcttgtc ggcactctgt cttgcgtttt gttcgcggtg    60
ccggagtatg gacgggcttg tagtgctct                                     89

<210> SEQ ID NO 37
<211> LENGTH: 38
<212> TYPE: DNA
<213> ORGANISM: Artificial
<220> FEATURE:
<223> OTHER INFORMATION: forward primer for ERApt-1

<400> SEQUENCE: 37
gtaatacgac tcactatagg gcaccgcgaa caaaacgc                           38

<210> SEQ ID NO 38
<211> LENGTH: 17
<212> TYPE: DNA
<213> ORGANISM: Artificial
<220> FEATURE:
<223> OTHER INFORMATION: reverse primer for ERApt-1

<400> SEQUENCE: 38
gggcactctg tcttgcg                                                  17

<210> SEQ ID NO 39
<211> LENGTH: 42
<212> TYPE: DNA
<213> ORGANISM: Artificial
<220> FEATURE:
<223> OTHER INFORMATION: forward primer for ERApt-1r-24nt

<400> SEQUENCE: 39
caagacagag tgccgacaag agcactacaa gcccgtccat ac                      42

<210> SEQ ID NO 40
<211> LENGTH: 35
<212> TYPE: DNA
<213> ORGANISM: Artificial
<220> FEATURE:
<223> OTHER INFORMATION: forward primer for AptER-1x1

<400> SEQUENCE: 40
agatatcgga tccgagaggc accgcgaaca aaacg                       35

<210> SEQ ID NO 41
<211> LENGTH: 41
<212> TYPE: DNA
<213> ORGANISM: Artificial
<220> FEATURE:
<223> OTHER INFORMATION: reverse primer for AptER-1x1

<400> SEQUENCE: 41
agatatcaag cttttccaaa aaagagaggc ttgtagtgct c                 41

<210> SEQ ID NO 42
<211> LENGTH: 30
<212> TYPE: DNA
<213> ORGANISM: Artificial
<220> FEATURE:
<223> OTHER INFORMATION: forward primer for AptER-1x2

<400> SEQUENCE: 42
agatatcgga tccgcgtgac gggcaccgcg                             30

<210> SEQ ID NO 43
<211> LENGTH: 40
<212> TYPE: DNA
<213> ORGANISM: Artificial
<220> FEATURE:
<223> OTHER INFORMATION: reverse primer for AptER-1x1

<400> SEQUENCE: 43
agatatcaag cttttccaaa aaagcgcctc cggcttgtag                   40

<210> SEQ ID NO 44
<211> LENGTH: 31
<212> TYPE: DNA
<213> ORGANISM: Artificial
<220> FEATURE:
<223> OTHER INFORMATION: forward primer for AptER-4

<400> SEQUENCE: 44
agatatcgga tccgagaatt caactgccat c                           31

<210> SEQ ID NO 45
<211> LENGTH: 41
<212> TYPE: DNA
<213> ORGANISM: Artificial
<220> FEATURE:
<223> OTHER INFORMATION: reverse primer for AptER-4

<400> SEQUENCE: 45
agatatcaag cttttccaaa aaagagtcca gaagcttgta g                 41

<210> SEQ ID NO 46
<211> LENGTH: 24
<212> TYPE: DNA
<213> ORGANISM: Artificial
<220> FEATURE:
<223> OTHER INFORMATION: forward primer for AptER-4

<400> SEQUENCE: 46
agcttctgga ctctttttg gaaa                                    24

<210> SEQ ID NO 47
<211> LENGTH: 24
<212> TYPE: DNA
<213> ORGANISM: Artificial

```
<220> FEATURE:
<223> OTHER INFORMATION: reverse primer for AptER-4

<400> SEQUENCE: 47
agcttttcca aaaagagtc caga                                           24

<210> SEQ ID NO 48
<211> LENGTH: 62
<212> TYPE: DNA
<213> ORGANISM: Artificial
<220> FEATURE:
<223> OTHER INFORMATION: negative control forward primer

<400> SEQUENCE: 48
gatccactac cgttgttata ggtgttcaag agacacctat aacaacggta gtttttttgga   60 aa                                                                  62

<210> SEQ ID NO 49
<211> LENGTH: 62
<212> TYPE: DNA
<213> ORGANISM: Artificial
<220> FEATURE:
<223> OTHER INFORMATION: negative control reverse primer

<400> SEQUENCE: 49
cactaccgtt gttataggtg ttcaagagac acctataaca acggtagttt tttggaaaag   60
ct                                                                  62

<210> SEQ ID NO 50
<211> LENGTH: 35
<212> TYPE: DNA
<213> ORGANISM: Artificial
<220> FEATURE:
<223> OTHER INFORMATION: forward primer for AptER-1x1

<400> SEQUENCE: 50
agatatcgga tgcgagaggc accgcgaaca aaacg                              35

<210> SEQ ID NO 51
<211> LENGTH: 37
<212> TYPE: DNA
<213> ORGANISM: Artificial
<220> FEATURE:
<223> OTHER INFORMATION: reverse primer for AptER-1x1

<400> SEQUENCE: 51
agatatcgga tccaaaaaag agaggcttgt agtgctc                            37

<210> SEQ ID NO 52
<211> LENGTH: 30
<212> TYPE: DNA
<213> ORGANISM: Artificial
<220> FEATURE:
<223> OTHER INFORMATION: forward primer for AptER-1x2

<400> SEQUENCE: 52
agatatcgga tgcgcgtgac gggcaccgcg                                    30

<210> SEQ ID NO 53
<211> LENGTH: 36
<212> TYPE: DNA
<213> ORGANISM: Artificial
<220> FEATURE:
<223> OTHER INFORMATION: reverse primer for AptER-1x2
```

-continued

<400> SEQUENCE: 53
agatatcgga tccaaaaaag cgcctccggc ttgtag    36

<210> SEQ ID NO 54
<211> LENGTH: 31
<212> TYPE: DNA
<213> ORGANISM: Artificial
<220> FEATURE:
<223> OTHER INFORMATION: forward primer for AptER-4

<400> SEQUENCE: 54
agatatcgga tgcgagaatt caactgccat c    31

<210> SEQ ID NO 55
<211> LENGTH: 37
<212> TYPE: DNA
<213> ORGANISM: Artificial
<220> FEATURE:
<223> OTHER INFORMATION: reverse primer for AptER-4

<400> SEQUENCE: 55
agatatcgga tccaaaaaag agtccagaag cttgtag    37

<210> SEQ ID NO 56
<211> LENGTH: 53
<212> TYPE: DNA
<213> ORGANISM: Artificial
<220> FEATURE:
<223> OTHER INFORMATION: negative control forward primer

<400> SEQUENCE: 56
actaccgttg ttataggtgt tcaagagaca cctataacaa cggtagtttt ttg    53

<210> SEQ ID NO 57
<211> LENGTH: 59
<212> TYPE: DNA
<213> ORGANISM: Artificial
<220> FEATURE:
<223> OTHER INFORMATION: negative control reverse primer

<400> SEQUENCE: 57
cgactaccgt tgttataggt gttcaagaga cacctataac aacggtagtt ttttggatc    59

<210> SEQ ID NO 58
<211> LENGTH: 17
<212> TYPE: DNA
<213> ORGANISM: Artificial
<220> FEATURE:
<223> OTHER INFORMATION: M13 forward primer

<400> SEQUENCE: 58
gttttcccag tcacgac    17

<210> SEQ ID NO 59
<211> LENGTH: 21
<212> TYPE: DNA
<213> ORGANISM: Artificial
<220> FEATURE:
<223> OTHER INFORMATION: 3.0 reverse primer

<400> SEQUENCE: 59
gagttagctc actcattagg c    21

<210> SEQ ID NO 60
<211> LENGTH: 17

```
<212> TYPE: DNA
<213> ORGANISM: Artificial
<220> FEATURE:
<223> OTHER INFORMATION: pSUPER:Sequencing primer 1

<400> SEQUENCE: 60
ggaagccttg gcttttg                                                17

<210> SEQ ID NO 61
<211> LENGTH: 17
<212> TYPE: DNA
<213> ORGANISM: Artificial
<220> FEATURE:
<223> OTHER INFORMATION: pSUPER:Sequencing primer 2

<400> SEQUENCE: 61
gatgacgtca gcgttcg                                                17

<210> SEQ ID NO 62
<211> LENGTH: 17
<212> TYPE: DNA
<213> ORGANISM: Artificial
<220> FEATURE:
<223> OTHER INFORMATION: pSHAG-MAGIC M13 forward primer

<400> SEQUENCE: 62
gttttcccag tcacgac                                                17

<210> SEQ ID NO 63
<211> LENGTH: 17
<212> TYPE: DNA
<213> ORGANISM: Artificial
<220> FEATURE:
<223> OTHER INFORMATION: pSHAG-MAGIC M13 reverse primer

<400> SEQUENCE: 63
caggaaacag ctatgac                                                17

<210> SEQ ID NO 64
<211> LENGTH: 21
<212> TYPE: DNA
<213> ORGANISM: Artificial
<220> FEATURE:
<223> OTHER INFORMATION: AptER-1x1 qPCR forward primer

<400> SEQUENCE: 64
gagaggcacc gcgaacaaaa c                                           21

<210> SEQ ID NO 65
<211> LENGTH: 26
<212> TYPE: DNA
<213> ORGANISM: Artificial
<220> FEATURE:
<223> OTHER INFORMATION: AptER-1x1 qPCR reverse primer

<400> SEQUENCE: 65
aagagaggct tgtagtgctc ttgtcg                                      26

<210> SEQ ID NO 66
<211> LENGTH: 16
<212> TYPE: DNA
<213> ORGANISM: Artificial
<220> FEATURE:
<223> OTHER INFORMATION: AptER-1x2 qPCR forward primer

<400> SEQUENCE: 66
```

```
gcgtgacggg caccgc                                                          16

<210> SEQ ID NO 67
<211> LENGTH: 21
<212> TYPE: DNA
<213> ORGANISM: Artificial
<220> FEATURE:
<223> OTHER INFORMATION: AptER-1x2 qPCR reverse primer

<400> SEQUENCE: 67
aagcgcctcc ggcttgtagt g                                                    21

<210> SEQ ID NO 68
<211> LENGTH: 26
<212> TYPE: DNA
<213> ORGANISM: Artificial
<220> FEATURE:
<223> OTHER INFORMATION: AptER-4 qPCR forward primer

<400> SEQUENCE: 68
gagaattcaa ctgccatcta ggccac                                               26

<210> SEQ ID NO 69
<211> LENGTH: 32
<212> TYPE: DNA
<213> ORGANISM: Artificial
<220> FEATURE:
<223> OTHER INFORMATION: AptER-4 qPCR reverse primer

<400> SEQUENCE: 69
aagagtccag aagcttgtag tacttaatac tc                                        32

<210> SEQ ID NO 70
<211> LENGTH: 22
<212> TYPE: DNA
<213> ORGANISM: Artificial
<220> FEATURE:
<223> OTHER INFORMATION: beta actin qPCR forward primer

<400> SEQUENCE: 70
ctgtccacct tccagcagat gt                                                   22

<210> SEQ ID NO 71
<211> LENGTH: 22
<212> TYPE: DNA
<213> ORGANISM: Artificial
<220> FEATURE:
<223> OTHER INFORMATION: beta actin qPCR reverse primer

<400> SEQUENCE: 71
cgcaactaag tcatagtccg cc                                                   22

<210> SEQ ID NO 72
<211> LENGTH: 98
<212> TYPE: RNA
<213> ORGANISM: Artificial
<220> FEATURE:
<223> OTHER INFORMATION: Filter Binding Sequence aptamer

<400> SEQUENCE: 72
gggagaauuc aacugccauc uaggcuugaa acuuagcgcc uccggucacg uggaguuagg          60
aggcgugagg ccaaguacua caagcuucug gacucggu                                  98

<210> SEQ ID NO 73
<211> LENGTH: 13
```

```
<212> TYPE: DNA
<213> ORGANISM: Xenopus laevis

<400> SEQUENCE: 73
ggtcacagtg acc                                                          13

<210> SEQ ID NO 74
<211> LENGTH: 48
<212> TYPE: RNA
<213> ORGANISM: Artificial
<220> FEATURE:
<223> OTHER INFORMATION: negative control shRNA

<400> SEQUENCE: 74
acuaccguug uuauaggugu ucaagagaca ccuauaacaa cgguaguu                    48
```